US011462296B2

(12) United States Patent
Modiano et al.

(10) Patent No.: US 11,462,296 B2
(45) Date of Patent: Oct. 4, 2022

(54) IDENTIFYING PRESENCE AND COMPOSITION OF CELL-FREE NUCLEIC ACIDS

(71) Applicant: Regents of the University of Minnesota, Minneapolis, MN (US)

(72) Inventors: Jaime F. Modiano, Roseville, MN (US); Milcah C. Scott, Minneapolis, MN (US); John R. Garbe, Woodbury, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 1299 days.

(21) Appl. No.: 15/783,776

(22) Filed: Oct. 13, 2017

(65) Prior Publication Data

US 2018/0105866 A1  Apr. 19, 2018

Related U.S. Application Data

(60) Provisional application No. 62/407,987, filed on Oct. 13, 2016.

(51) Int. Cl.
| | |
|---|---|
| *G16B 5/00* | (2019.01) |
| *G01N 33/92* | (2006.01) |
| *C12Q 1/6869* | (2018.01) |
| *G16B 20/00* | (2019.01) |
| *G16B 30/00* | (2019.01) |
| *G16B 30/10* | (2019.01) |
| *G16B 30/20* | (2019.01) |
| *G16B 20/20* | (2019.01) |
| *C12Q 1/6806* | (2018.01) |
| *C40B 40/08* | (2006.01) |

(52) U.S. Cl.
CPC ............. *G16B 5/00* (2019.02); *C12Q 1/6869* (2013.01); *G01N 33/92* (2013.01); *G16B 20/00* (2019.02); *G16B 20/20* (2019.02); *G16B 30/00* (2019.02); *G16B 30/10* (2019.02); *G16B 30/20* (2019.02); *C12Q 1/6806* (2013.01); *C40B 40/08* (2013.01)

(58) Field of Classification Search
None
See application file for complete search history.

(56) References Cited

PUBLICATIONS

Milane et al. in (Journal of Controlled Release (2015) vol. 219:278-294).*
Schageman et al. (BioMed Research International (2013) Article ID 253957:15 pages).*
Hannafon et al. (Breast Cancer Research (2016) 18:14 pages).*
Callari et al. BMC Genomics vol. 19:12 pages (Year: 2018).*

Angstadt et al., "Characterization of Canine Osteosarcoma by Array Comparative Genomic Hybridization and RT-qPCR: Signatures of Genomic Imbalance in Canine Osteosarcoma Parallel the Human Counterpart," Genes, Chromosomes & Cancer, Wiley Online Library, Aug. 11, 2011, 16 pp.
Arras et al., "Assessment of post-laparotomy pain in laboratory mice by telemetric recording of heart rate and heart rate variability," BMC Veterinary Research, Aug. 2, 2007, 10 pp.
Azevedo et al., "Circulating Microparticles as Therapeutic Targets in Cardiovascular Diseases," Bentham Science Publishers Ltd., Feb. 2007, 12 pp.
Banerjee et al., "CD133+ tumor initiating cells (TIC) in a syngenic murine model of pancreatic cancer respond to Minnelide," Clinical Cancer Research, May 1, 2014, 22 pp.
Bolger et al., "Trimmomatic: a flexible trimmer for Illumina sequence data," Bioinformatics, vol. 30, Apr. 1, 2014, 7 pp.
Brune et al., "Mesenchymal stromal cells from primary osteosarcoma are non-malignant and strikingly similar to their bone marrow counterparts," UICC, International Journal of Cancer, Sep. 28, 2010, 13 pp.
Caswell et al., "Obligate Progression Precedes Lung Adenocarcinoma Dissemination," Cancer Discovery, Research Brief, Apr. 16, 2014, 10 pp.
Chaffee et al., "A Clinically Relevant Mouse Model of Canine Osterosarcoma with Spontaneous Metastasis," In Vivo, Sep. 2013, 5 pp.
Chuen Choi et al., "Lessons from patient-derived xenografts for better in vitro modeling of human cancer," Advanced Drug Delivery Reviews, Elsevier, Oct. 2014, 17 pp.
Creighton et al., "Profiling of pathway-specific changes in gene expression following growth of human cancer cell lines transplanted into mice," Genome Biology, Jun. 23, 2003, 12 pp.
Daniel et al., "A Primary Xenograft Model of Small-Cell Lung Cancer Reveals Irreversible Changes in Gene Expression Imposed by Culture In vitro," American Association for Cancer Research, Apr. 15, 2009, 11 pp.
Delitto et al., "Patient-Derived Xenograft Models for Pancreatic Adenocarcinoma Demonstrate Retention of Tumor Morphology through Incorporation of Murine Stromal Elements," The American Journal of Pathology, vol. 185, No. 5, May 2015, 7 pp.
Fan et al., "Comparative Aspects of Osteosarcoma Pathogenesis in Humans and Dogs," Veterinary Sciences, Aug. 17, 2015, 21 pp.

(Continued)

*Primary Examiner* — Lori A. Clow
(74) *Attorney, Agent, or Firm* — Shumaker & Sieffert, P.A.

(57) ABSTRACT

This disclosure describes example techniques and systems for identifying the presence and/or composition of nucleic acids in the blood of a host organism of a model species harboring tissue of a donor organism of another species. For example, the technique may involve identifying the presence and composition of nucleic acids in the blood of a mouse harboring tissue of a human or another companion animal. These cell-free nucleic acids that are identified can be used as biomarkers to determine the presence of a disease, its biological behavior, its rate of progression, and/or the response of the disease to one or more unique therapies. In other examples, the cell-free nucleic acids may be used as biomarkers to determine a response of the host species to the tissue of the donor organism or a response of tissue derived from the second organism to transplantation within the first organism of the first species.

30 Claims, 37 Drawing Sheets

(56) References Cited

PUBLICATIONS

Fritz et al., "A phase I clinical study to evaluate safety of orally administered, genetically engineered *Salmonella enterica* serovar Typhimurium for canine osteosarcoma," Veterinary Medicine and Science, Wiley & Sons Ltd., Jun. 6, 2016, 12 pp.

Garimella et al., "Biological characterization of preclinical Bioluminescent Osteosarcoma Orthotopic Mouse (BOOM) model: A multi-modality approach," Journal of Bone Oncology, Elsevier, Dec. 31, 2012, 11 pp.

Gordon et al., "Identification of Three Molecular and Functional Subtypes in Canine Hemangiosarcoma through Gene Expression Profiling and Progenitor Cell Characterization," The American Journal of Pathology, Elsevier, Dec. 16, 2013, 11 pp.

He et al., "Progressive epithelial to mesenchymal transitions in ARCaPE prostate cancer cells during xenograft tumor formation and metastasis," NIH Public Access, Apr. 1, 2010, 17 pp.

Hollingshead et al., "Gene expression profiling of 49 human tumor xenografts from in vitro culture through multiple in vivo passages—strategies for data mining in support of therapeutic studies," BMC Genomics, May 22, 2014, 16 pp.

Johann et al., "Tumour stromal cells derived from paediatric malignancies display MSC-like properties and impair NK cell cytotoxicity," BioMed Central, Sep. 21, 2010, 10 pp.

Kanaya et al., "Anti-Tumor Effect of Adenoviral Vector-Mediated p53 Gene Transfer on the Growth of Canine Osteosarcoma Xenografts in Nude Mice," Internal Medicine, J. Vet. Med. Sci, published online, Feb. 22, 2011, 7 pp.

Kang et al., "Dissecting Tumor-Stromal Interactions in Breast Cancer Bone Metastasis," Endocrinology and Metabolism, Korean Endocrine Society, May 13, 2016, 7 pp.

Kim et al., "HISAT: a fast spliced aligner with low memory requirements," Nat Methods, Apr. 2015, 17 pp.

Zhou et al., "Robustly detecting differential expression in RNA sequencing data using observation weights," Nucleic Acids Research, vol. 42, Issue 11, Mar. 31, 2014, 10 pp.

Kim et al., "Interleukin-8 Promotes Canine Hemangiosarcoma Growth by Regulating the Tumor Microenvironment," Exp. Cell Research, Apr. 15, 2014, 19 pp.

Kuijjer et al., "mRNA expression profiles of primary high-grade central osteosarcoma are preserved in cell lines and xenografts," BMC Medical Genomics, Sep. 20, 2011, 12 pp.

Laszlo et al., "High expression of myocyte enhancer factor 2C (MEF2C) is associated with adverse-risk features and poor outcome in pediatric acute myeloid leukemia: a report from the Children's Oncology Group," Journal of Hematology & Oncology, Oct. 20, 2015, 10 pp.

Lauvrak et al., "Functional characterisation of osteosarcoma cell lines and identification of mRNAs and miRNAs associated with aggressive cancer phenotypes," British Journal of Cancer, published online Sep. 24, 2013, 9 pp.

Li et al., "The Sequence Alignment/Map format and SAMtools," Bioinformatics Applications Note, vol. 25, May 30, 2009, 2 pp.

Liao et al., "featurecounts: an efficient general purpose program for assigning sequence reads to genomic features," Bioinformatics, vol. 30, Nov. 7, 2013, 8 pp.

Martin et al., "The Genetics of Osteosarcoma," Review Article, Hindawi Publishing Corporation, vol. 2012, accepted Jan. 31, 2012, 12 pp.

McIntyre et al., "Mouse models of colorectal cancer as preclinical models," Prospects & Overviews, Jun. 26, 2015, 12 pp.

Mintz et al., "An Expression Signature Classifies Chemotherapy-Resistant Pediatric Osteosarcoma," Cancer Research Article, Mar. 1, 2005, 8 pp.

Mirabello et al., "Osteosarcoma incidence and survival rates from 1973 to 2004: Data from the Surveillance, Epidemiology, and End Results Program," Cancer, National Institute of Health, Apr. 1, 2009, 18 pp.

Modiano et al., "Inflammation, Apoptosis, and Necrosis Induced by Neoadjuvant Fas Ligand Gene Therapy Improves Survival of Dogs With Spontaneous Bone Cancer," The American Society of Gene & Cell Therapy, Jun. 30, 2012, 10 pp.

Mohseny et al., "Functional characterization of osteosarcoma cell lines provides representative models to study the human disease," Laboratory Investigation, Apr. 25, 2011, 11 pp.

Mohseny et al., "Osteosarcoma Models: From Cell Lines to Zebrafish," Review Article, Hindawi Publishing Corporation, Nov. 24, 2011, 12 pp.

Moriarity et al., "A Sleeping Beauty forward genetic screen identifies new genes and pathways driving osteosarcoma development and metastasis," Nat Genet, Jun. 2015, 30 pp.

O'Donoghue et al., "Expression profiling in canine osteosarcoma: identification of biomarkers and pathways associated with outcome," BioMed Central, Sep. 22, 2010, 16 pp.

Record, "Exosomes as intercellular signalosomes and pharmacological effectors," HAL, Apr. 22, 2012, 20 pp.

Robinson et al., "edgeR: a Bioconductor package for differential expression analysis of digital gene expression data," Bioinformatics, vol. 26, No. 1, Nov. 11, 2009, 2 pp.

Sampson et al., "Xenograft and genetically engineered mouse model systems of osteosarcoma and Ewing's sarcoma: tumor models for cancer drug discovery," Expert Opinion Drug Discovery, Oct. 2013, 16 pp.

Sarver et al., "MicroRNAs at the human 14q32 locus have prognostic significance in osteosarcoma," Orphanet Journal of Rare Diseases, Jan. 11, 2013, 11 pp.

Scott et al., "Heterotypic mouse models of canine osteosarcoma recapitulate tumor heterogeneity and biological behavior," Disease Models & Mechanisms, The Company of Biologists, Sep. 23, 2016, 10 pp.

Scott et al., "Molecular subtypes of osteosarcoma identified by reducing tumor heterogeneity through an interspecies comparative approach," Bone, Sep. 2011, 26 pp.

Wolfe et al., "Effect of zoledronic acid and amputation on bone invasion and lung metastasis of canine osteosarcoma in nude mice," Clin Exp Metastasis, Apr. 2011, 27 pp.

Scott et al., Unbiased Discovery of Exosome-Associated Biomarkers Using Xenograft Models, Poster 817 presented Jun. 21, 2016, University of Minnesota, 1 pp.

Sleeman, "The metastatic niche and stromal progression," Cancer Metastasis Review, published online Jun. 15, 2012, Springer Link, 12 pp.

Talmadge et al., "Murine Models to Evaluate Novel and Conventional Therapeutic Strategies for Cancer," The American Journal of Pathology, vol. 70, No. 3, Mar. 2007, 12 pp.

Tamburini et al., "Gene Expression Profiles of Sporadic Canine Hemangiosarcoma Are Uniquely Associated with Breed," PLoS One, vol. 4, Issue 5, May 20, 2009, 12 pp.

Thayanithy et al., "Perturbation of 14q32 miRNAs-cMYC gene network in osteosarcoma," Bone, Jan. 2012, 25 pp.

Varshney et al., "Understanding the Osteosarcoma Pathobiology: A Comparative Oncology Approach," Veterinary Sciences, MDPI, Jan. 18, 2016, 15 pp.

Wang et al., "Effector T Cells Abrogate Stroma-Mediated Chemoresistance in Ovarian Cancer," Cell, May 19, 2016, 28 pp.

Hood et al., "Exosomes Released by Melanoma Cells Prepare Sentinel Lymph Nodes for Tumor Metastasis," Cancer Research, Jun. 2011, 21 pp.

Scott et al., "Aberrant Retinoblastoma (RB)-E2F Transcriptional Regulation Defines Molecular Phenotypes of Osteosarcoma," The Journal of Biological Chemistry, vol. 290, No. 47, Published Sep. 16, 2015, 14 pp.

Dodd et al., "Myogenic transcription factors regular pro-metastatic miR-182," Oncogene, Apr. 7, 2016, 18 pp.

Egas-Bejar et al., "Theranostic profiling for actionable aberrations in advanced high risk osteosarcoma with aggressive biology reveals high molecular diversity: the human fingerprint hypothesis," Oncoscience, vol. 1, No. 2, Mar. 12, 2014, 13 pp.

Fenger et al., "Canine Osteosarcoma: A Naturally Occurring Disease to Inform Pediatric Oncology," ILAR Journal, vol. 55, No. 1, Apr. 1, 2014, 17 pp.

(56) References Cited

PUBLICATIONS

Jiang et al., "Expression of ERCC1, TYMS, RRM1, TUBB3, and non-muscle myosin II, myoglobin and MyoD1 in lung adenocarcinoma pleural effusions predicts survival in patients receiving platinum-based chemotherapy," Molecular Medicine Reports, Spandidos Publications, Dec. 30, 2014, 12 pp.

Mayordomo et al., "A Tissue Microarray Study of Osteosarcoma: Histopathologic and Immunohistochemical Validation of Xenotransplanted Tumors as Preclinical Models," Research Article, Applied Immununohistochemical Mol. Morphol. Feb. 24, 2010, 9 pp.

Morello et al., "Biology, diagnosis and treatment of canine appendicular osteosarcoma: Similarities and differences with human osteosarcoma," The Veterinary Journal, Aug. 28, 2010, 10 pp.

Pacharinsak et al., "Animal Models of Cancer Pain," Comparative Medicine, vol. 58, No. 3, Jun. 2008, 14 pp.

Tan et al., "Osteosarcoma—conventional treatment vs. gene therapy," Cancer Biology & Therapy, published online, Jan. 15, 2009, 13 pp.

Angstadt et al., "A genome-wide approach to comparative oncology: high-resolution oligonucleotide aCGH of canine and human osteosarcoma pinpoints shared Microaberrations," Cancer Genetics, Elsevier, Sep. 24, 2012, 16 pp.

Bielack et al., "Prognostic Factors in High-Grade Osteosarcoma of the Extremities or Trunk: An Analysis of 1,702 Patients Treated on Neoadjuvant Cooperative Osteosarcoma Study Group Protocols," Journal of Clinical Oncology, vol. 20, No. 3, Feb. 1, 2002, 16 pp.

Coomer et al., "Development of an intramuscular xenograft model of canine osteosarcoma in mice for evaluation of the effects of radiation therapy, American Journal of Veterinary Res., vol. 70, No. 1, Jan. 2009, 7 pp.

Kawada et al., "Small molecules modulating tumor-stromal cell interactions: new candidates for anti-tumor drugs," The Journal of Antibiotics, Mar. 23, 2016, 4 pp.

Withrow et al., "Comparative Aspects of Osteosarcoma," Clinical Orthopaedics and Related Research, Nov. 29, 1990, 10 pp.

Jaffe., "Historical Perspective on the Introduction and Use of Chemotherapy for the Treatment of Osteosarcoma," Current Advances in Osteosarcoma, Advances in Experimental Medicine and Biology, May 2, 2014, 30 pp.

Jareonsong et al., "Effects of transplantation sites on tumour growth, pulmonary metastasis and ezrin expression of canine osteosarcoma cell lines in nude mice," Veterinary and Comparative Oncology, Blackwell Publishing Ltd, Sep. 9, 2011, 9 pp.

Shin et al., "Changes in the biological characteristics of glioma cancer stem cells after serial in vivo subtransplantation," Childs Nerve System, Springer Online, published online Nov. 10, 2012, 10 pp.

Kansara et al., "Molecular Pathogenesis of Osteosarcoma," Review Paper, DNA and Cell Biology, vol. 26, No. 1, Jan. 31, 2007, 18 pp.

Sottnik et al., "Induction of VEGF by tepoxalin does not lead to increased tumour growth in a canine osteosarcoma xenograft," Vet Comparative Oncology, Blackwell Publishing Ltd, Sep. 13, 2010, 13 pp.

U.S. Appl. No. 62/567,606, by Jaime F. Modiano, filed Oct. 3, 2017.

Alonso et al., "FeCo nanowires with enhanced heating powers and controllable dimensions for magnetic hyperthermia," Journal of Applied Physics, vol. 117, No. 17, Jan. 2015, 4 pp.

Altman et al., "Unmet needs: Research helps regulators do their jobs," Science Translational Medicine, vol. 7, No. 315, Nov. 2015, 8 pp.

Anderson et al., "Melanoma cell resistance to phagocytosis is unrelated to expression of conventional "eat me/don't eat-me" signals," Cancer Immunology Research, vol. 4, Abstract A143, Jan. 2016, 2 pp.

Becker et al., "Extracellular Vesicles in Cancer: Cell-to-Cell Mediators of Metastasis," Cancer Cell, vol. 30, No. 6, Dec. 2016, 26 pp.

Beleggia et al., "Demagnetization factors of the general ellipsoid: An alternative to the Maxwell approach," Philosophical Magazine, vol. 86, No. 16, Jun. 2006, 16 pp.

Berganza et al., "Multisegmented Nanowires: A Step towards the Control of the Domain Wall Configuration," Scientific Reports, vol. 7, No. 1, Sep. 2017, 8 pp.

Biehl et al., "Synthesis, Characterization, and Applications of Magnetic Nanoparticles Featuring Polyzwitterionic Coatings," Polymers (Basel), vol. 10, No. 1, Jan. 2018, 28 pp.

Bran et al., "Co/Au multisegmented nanowires: a 3D array of magnetostatically coupled nanopillars," Nanotechnology, vol. 28, No. 9, Mar. 2017, 7 pp.

Buford et al., "A technique for error estimation of linewidth and damping parameters extracted from ferromagnetic resonance measurements," Journal of Applied Physics, vol. 117, No. 17, Feb. 2015, 4 pp.

Chaput et al., "Exosomes immune properties and potential clinical implementations," Seminars in Immunopathology, vol. 33, No. 5, Sep. 2011, 22 pp.

Contreras et al., "Targeted cancer cell death induced by biofunctionalized magnetic nanowires," 2nd Middle East Conference on Biomedical Engineering, Feb. 2014, 4 pp.

Donahue et al., "OOMMF User's Guide, Version 1.0," Interagency Report NISTIR 6376, national Institute of Standards and Technology, Sep. 1999, 92 pp.

Encinas-Oropesa et al., "Dipolar interactions in arrays of nickel nanowires studied by ferromagnetic resonance," Physical Review B, vol. 63, No. 10, Feb. 2001, 6 pp.

Faraji et al., "Magnetic nanoparticles: Synthesis, stabilization, functionalization, characterization, and applications," Journal of the Iranian Chemical Society, vol. 7, No. 1, Mar. 2010, 37 pp.

Hultgren et al., "Optimization of Yield in Magnetic Cell Separations Using Nickel Nanowires of Different Lengths," Biotechnology Process, vol. 21, No. 2, Mar. 2005, 7 pp.

Jain, "Applications of Nanobiotechnology in Clinical Diagnostics," Clinical Chemistry, Vo. 53, No. 11, Aug. 2007, 8 pp.

Javeed et al., "Exosomes and their role in the micro-/macro-environment a comprehensive review," Journal of Biomedical Research, vol. 31, No. 5, Sep. 2017, 9 pp.

Jokerst et al., "Nanoparticle PEGylation for imaging and therapy," Nanomedicine (Lond), vol. 6, No. 4, Jun. 2011, 27 pp.

Kalluri, "The biology and function of exosomes in cancer," Journal of Clinical Investigation, vol. 126, No. 4, Apr. 2016, 8 pp.

Kartopu et al., "Size effects and origin of easy-axis in nickel nanowire arrays," Journal of Applied Physics, vol. 109, No. 3, Feb. 2011, 8 pp.

Landau et al., "On the theory of the dispersion of magnetic permeability in ferromagnetic bodies," Phys. Zeitsch. der Sowjetunion, vol. 8, Jan. 1935, 9 pp.

Mirzael et al., "Diagnostic and Therapeutic Potential of Exosomes in Cancer: The Beginning of a New Tale?" Journal of Cellular Physiology, vol. 232, No. 12, Dec. 2017, 10 pp.

Modiano et al., "Mesenchymal stromal cells inhibit murine syngeneic anti-tumor immune responses by attenuating inflammation and reorganizing the tumor microenvironment," Cancer Immunol Immunother, vol. 64, No. 11, Nov. 2015, 21 pp.

Nemati et al., "Exosome enrichment in Blood Biopsies via Radio-Frequency Identification (RFID) Nanowire Tags," Poster presented at Upper-Midwest Agricultural Safety and Health Center, Oct. 3, 2017, 1 pp.

Piraux et al., "Template-grown NiFe/Cu/NiFe nanowires for spin transfer devices," Nano Letters, vol. 7 No. 9, Aug. 2007, 5 pp.

Pondman et al., "Magnetic drug delivery with FePd nanowires," Journal of Magnetism and Magnetic Materials, vol. 380, Apr. 2015, 8 pp.

Scott et al., "Characterization of RNA in osteosarcoma-derived exosomes," Proceedings of the Keystone Symposia Exosomes/Microvesicles: Novel Mechanisms of Cell-Cell Communication, Abstract, Jun. 2016, 1 pp.

Scott et al., "Role of osteosarcoma-derived exosomes in interactions with stromal environment and metastasis," University of Minnesota—College of Veterinary Medicine, E4, poster 2050, Jun. 2016, 1 pp.

Sharma et al., "Alignment of collagen matrices using magnetic nanowires and magnetic barcode readout using first order reversal curves (FORC) (invited)," Journal of Magnetism and Magnetic Materials, vol. 459, Aug. 2018, 6 pp.

(56) References Cited

PUBLICATIONS

Sharma et al., "FMR Measurements of Magnetic Nanostructures," Ferromagnetic Resonance-Theory and Applications, Chapter 4, Jul. 2013, 18 pp.

Sharma et al., "Inducing cells to disperse nickel nanowires via integrin-mediated responses," Nanotechnology, vol. 26, No. 13, Mar. 2015, 12 pp.

Sharma et al., "Magnetic Barcode Nanowires for Osteosarcoma Cell Control, Detection and Separations," IEEE Transactions on Magnetics, vol. 49, No. 1, Jan. 2013, 4 pp.

Sharma et al., "Tumor exosomes: cellular postmen of cancer diagnosis and personalized therapy," Nanomedicine (Lond ), vol. 11, No. 4, Feb. 2016, 17 pp.

Shore et al., "Electrodeposited Fe and Fe—Au nanowires as MRI Contrast Agents," Chemical Communications, vol. 52, Sep. 2016, 4 pp.

Sievers et al., "Microwave Interferometry for High Sensitivity VNA-FMR Measurements," IEEE Transactions on Magnetics, vol. 53, No. 4, Apr. 2017, 4 pp.

Siravegna et al., "Integrating liquid biopsies into the management of cancer," Nature Reviews Clinical Oncology, vol. 14, Mar. 2017, 18 pp.

Sokolov et al., "Single-Point FMR Linewidth Measurement by TE10 Rectangular Transmission Cavity Perturbation," EEE Transactions on Microwave Theory and Techniques, vol. 64, No. 11, Nov. 2016, 9 pp.

Steinbichler et al., "The Role of Exosomes in Cancer Metastasis," Seminars in Cancer Biology, vol. 44, Jun. 2017, 12 pp.

Syn et al., "Evolving landscape of tumor molecular profiling for personalized cancer therapy: a comprehensive review," Expert Opinion on Drug Metabolism & Toxicology, vol. 12, No. 8, Jun. 2016, 12 pp.

Um et al., "RFID Biomarkers Using Nanowires," MINT Poster, Oct. 2017, 1 pp.

Valenzuela et al., "Magnetoimpedance, ferromagnetic resonance, and low field microwave absorption in amorphous ferromagnets," Journal of Non-Crystalline Solids, vol. 353, Nos. 8-10, Apr. 2007, 5 pp.

Whiteside, "Tumor-Derived Exosomes and Their Role in Cancer Progression," Advances in Clinical Chemistry, vol. 74, Apr. 2016, 35 pp.

Xi et al., "Inter- and intra-nanowire magnetic interaction in Co/Cu multilayer nanowires deposited by electrochemical deposition," Physica B: Condensed Matter, vol. 518, Aug. 2017, 4 pp.

Zhou et al., "Development of a Biolabeling System Using Ferromagnetic nanowires," IEEE Journal of Electromagnetics, RF and Microwaves in Medicine and Biology, vol. 3, No. 2, Dec. 2018, 10 pp.

Zhou et al., "Ferromagnetic Resonance Characterization of Magnetic Nanowires for Biolabel Applications," 2018 IEEE International Microwave Biomedical Conference (IMBioC), Jun. 2018, 3 pp.

Zimmerman et al., "Cellular uptake and dynamics of unlabeled freestanding silicon nanowires," Science Advances, vol. 2, No. 12, Dec. 2016, 12 pp.

Altanerova et al., "Exosomes of human mesenchymal stem/stromal/medicinal signaling cells," MSC Exosomes, Neoplasma, Aug. 16, 2017, 7 pp.

D'Asti et al., "Extracellular Vesicles in Brain Tumor Progression," Cell Mol Neurobiology, Review Paper, Oct. 24, 2015, 25 pp.

Atay et al., "Oncogenic KIT-containing exosomes increase gastrointestinal stromal tumor cell invasion," Cell Biology, PNAS, Dec. 3, 2013, 6 pp.

Baglio et al., "Human bone marrow- and adipose—mesenchymal stem cells secrete exosomes enriched in distinctive miRNA and tRNA species," Stem Cell Research and Therapy, Jul. 1, 2015, 20 pp.

Broner et al., "TSAP6 is a novel candidate marker for poor survival in metastatic high-grade serous carcinoma," Human Pathology, Elsevier, Oct. 10, 2016, 180-187 pp.

Camussi et al., "Tumor-Derived Microvesicles and the Cancer Microenvironment," Current Molecular Medicine, vol. 13, No. 1, Jan. 2013, 10 pp.

Corcoran et al., "miR-34a is an Intracellular and Exosomal Predictive Biomarker for Response to Docetaxel with Clinical Relevance to Prostate Cancer Progression," The Prostate 74, accepted Jun. 5, 2014, 1320-1334 pp.

Corrado et al., "Chronic myelogenous leukemia exosomes modulate bone marrow microenvironmental through activation of epidermal growth factor receptor," J. Cell. Mol. Med. vol. 20, No. 10, Mar. 8, 2016, 1829-1839 pp.

Ekstrom et al., "WNT5A induces release of exosomes containing pro-angiogenic and immunosuppressive factors from malignant melanoma cells," Molecular Cancer, 2014 (Applicant points out, in accordance with MPEP 609.04(a), that the year of publication, 2014, is sufficiently earlier than the effective U.S. filing date, so that the particular month of publication is not in issue.), 15 pp.

El-Saghir et al., "ATL-derived exosomes modulate mesenchymal stem cells; potential role in leukemia progression," Retrovirology, Oct. 19, 2016, 13 pp.

Farahani et al., "CLL Exosomes Modulate the Transcriptome and Behavior of Recipient Stromal Cells and Are Selectively Enriched in miR-202-3p," PLOS One, Oct. 28, 2015, 18 pp.

Fei et al., "B-cell precursor acute lymphoblastic leukemia and stromal cells communicate through Galectin-3," Oncotarget, vol. 6, No. 13, Mar. 30, 2015, 17 pp.

Fujita et al., "Extracellular vesicle transfer of cancer pathogenic components," Cancer Science Article Review, Jan. 18, 2016, 6 pp.

Goldvaser et al., "Characterisation of blood-derived exosomal hTERT mRNA secretion in cancer patients: a potential pan-cancer marker," British Journal of Cancer, May 16, 2017, 5 pp.

Gopal et al., "Extracellular vesicles: their role in cancer biology and epithelial-mesenchymal transition," Biochemical journal, Oct. 10, 2016, 25 pp.

Guo et al., "Exosomes: New players in cancer (Review)," Oncology Reports, May 29, 2017, 11 pp.

Guowei et al., "Research Progress of Mechanism of mesenchymal Stem Celis-Derived Exosomes in Tissue Repair," Chinese Journal of Reparative and Reconstructive Surgery, Translation provided for the Abstract Only, vol. 30, Apr. 2016, 6 pp.

Huang et al., "Downregulation of estrogen receptor and modulation of growth of breast cancer cell lines mediated by paracrine stromal cell signals," Breast Cancer Res. Treat, HHS Public Access, first published Jan. 2017, 25 pp.

Kawamoto et al., "Tumor-Derived Microvesicles Induce Proangiogenic Phenotype in Endothelial Cells via Endocytosis," PLOS One, Mar. 30, 2012, 11 pp.

Kucharzewska et al., "Exosomes reflect the hypoxic status of glioma cells and mediate hypoxia-dependent activation of vascular cells during tumor development," PNAS, vol. 110, No. 18, Apr. 30, 2013, 6 pp.

Lee et al., "Microvesicles as mediators of intercellular communication in cancer—the emerging science of cellular 'debris'," Semin Immunopathology, Jan. 13, 2011, 455-467 pp.

Li et al., "Exosome-mediated transfer of lncRUNX2-AS1 from multiple myeloma cells to MSCs contributes to osteogenesis," Oncogene, May 14, 2018, 12 pp.

Li et al., "Lung tumor exosomes induce a pro-inflammatory phenotype in mesenchymal stem cells via NFkB-TLR signaling pathway," Journal of Hematology & Oncology, Apr. 18, 2016, 12 pp.

Lopatina et al., "Cross Talk between Cancer and Mesenchymal Stem Cells through Extracellular Vesicles Carrying Nucleic Acids," Frontiers in Oncology, vol. 6, Article 125, May 23, 2016, 11 pp.

Lou et al., "Exosomes derived from MiR-122-modified adipose tissue-derived MSCs increase chemosensitivity of hepatocellular carcinoma," Journal of Hematology & Oncology, Oct. 29, 2015, 11 pp.

Lu et al., "Exosomal miR-9 inhibits angiogenesis by targeting MDK and regulating PDK/AKT pathway in nasopharyngeal carcinoma," Journal of Experimental & Clinical Cancer Research, Jun. 26, 2018, 12 pp.

(56) References Cited

PUBLICATIONS

Martins et al., "Tumor-cell-derived microvesicles as carriers of molecular information in cancer," Current Opinion, vol. 25, No. 1, Jan. 2013, 10 pp.
Melzer et al., "Concise Review: Crosstalk of Mesenchymal Stroma/Stem-Like Cells with Cancer Cells Provides Therapeutic Potential," Stem Cells, Mar. 19, 2018, 18 pp.
Xu et al., "Lung adenocarcinoma cell-derived exosomal miR-21 facilitates osteoclastogenesis," Gene, Elsevier, May 2, 2018, 7 pp.
Muller et al., "Exosomes isolated from plasma of glioma patients enrolled in a vaccination trial reflect antitumor immune activity and might predict survival," OncoImmunology, Jan. 2015, 8 pp.
Muntion et al., "Microvesicles from Mesenchymal Stromal Cells Are Involved in HPC-Microenvironment Crosstalk in Myelodysplastic Patients," PLOS One, Feb. 2, 2016, 20 pp.
Tutar, "miRNA and Cancer; Computational and Experimental Approaches," Current Pharmaceutical Biotechnology, vol. 15, No. 5, May 2014, 1 pp.
Nazarenko et al., "Exosomes as Potential Tool for a Specific Delivery of Functional 19 pp. Molecules," Chapter 37, Ovarian Cancer, ISBN: 978-1-62703-546-0, 2013, (Applicant points out, in accordance with MPEP 609.04(a), that the year of publication, 2013, is sufficiently earlier than the effective U.S. filing date, so that the particular month of publication is not in issue.).
Ohyashiki et al., "Exosomes promote bone marrow angiogenesis in hematologic neoplasia: the role of hypoxia," Co-Hematology, vol. 23, No. 3, Wolters Kluwer Health, Inc., May 2016, 6 pp.
Pando et al., "Extracellular vesicles in leukemia," Leukemia Research, Elsevier, Nov. 21, 2017, 9 pp.
Rana et al., "Exosomal Tumor MicroRNA Modulates Premetastatic Organ Cells," NeoPlasia, vol. 15, No. 3, Mar. 2013, 281-295 pp.
Rossi et al., "The Role of Extracellular Vesicles in Bone Metastasis," International Journal of Molecular Sciences, vol. 19, No. 4, Apr. 10, 2018, 13 pp.
Santi et al., "Cancer associated fibroblasts transfer lipids and proteins to cancer cells through cargo vesicles supporting tumor growth," Biochimica et Biophysica Acta, Elsevier, Sep. 11, 2015, 13 pp.
Shao et al., "Chip-based analysis of exosomal mRNA mediating drug resistance in glioblastoma," Nature Communications, May 11, 2015, 9 pp.
Soldevilla et al., "Tumor-derived exosomes are enriched in ΔNp73, which promotes oncogenic potential in acceptor cells and correlates with patient survival," Human Molecular Genetics, vol. 23, No. 2, Sep. 18, 2013, 467-478 pp.
Takeshita et al., "Serum microRNA expression profile: miR-1246 as a novel diagnostic and prognostic biomarker for oesophageal squamous cell carcinoma," British Journal of Cancer, Jan. 29, 2013, 9 pp.
Valcz et al., "Exosomes in colorectal carcinoma formation: ALIX under the magnifying glass," Modern Pathology, published online May 6, 2016, 11 pp.
Van Deun et al., "The impact of disparate isolation methods for extracellular vesicles on downstream RNA profiling," Journal of Extracellular Vesicles, Sep. 18, 2014, 15 pp.
Wang et al., "Lung cancer exosomes initiate global long non-coding RNA changes in mesenchymal stem cells," International Journal of Oncology, Nov. 11, 2015, 681-689 pp.
Whiteside, Exosome and mesenchymal stem cell cross-talk in the tumor microenvironment, Seminars in Immunology, Elsevier, Dec. 8, 2017, 11 pp.
Xu et al., "Serum exosomal hnRNPH1 mRNA as a novel marker for hepatocellular carcinoma," Clin Chem Lab Med, Sep. 11, 2017, 6 pp.
Xu et al., "Serum exosomal long noncoding RNAs ENSG00000258332.1 and LINC00635 for the diagnosis and prognosis of hepatocellular carcinoma," Apr. 12, 2018, 23 pp.
Yang et al., "Role of Exosomal miRNA in Multiple Myeloma Progress and Its Possible Mechanism," Translation of the Abstract Only, J. Exp. Hematol, Feb. 2017, 6 pp.
Zhang et al., "Exosomes in cancer: small particle, big player," Journal of Hematology & Oncology, Jul. 10, 2015, 13 pp.
Zhang et al., "Transfer of microRNAs by extracellular membrane microvesicles: a nascent crosstalk model in tumor pathogenesis, especially tumor cell-microenvironment interactions," Journal of Hematology & Oncology, Feb. 22, 2015, 8 pp.
Zhou et al., "Reprogramming Malignant Cancer Cells toward a Benign Phenotype following Exposure to Human Embryonic Stem Cell Microenvironment," PLOS One, Jan. 9, 2017, 14 pp.
Zoller et al., "Pancreatic cancer diagnosis by free and exosomal miRNA," World Journal of Gastrointestinal Pathophysiology, Nov. 15, 2013, 18 pp.

\* cited by examiner

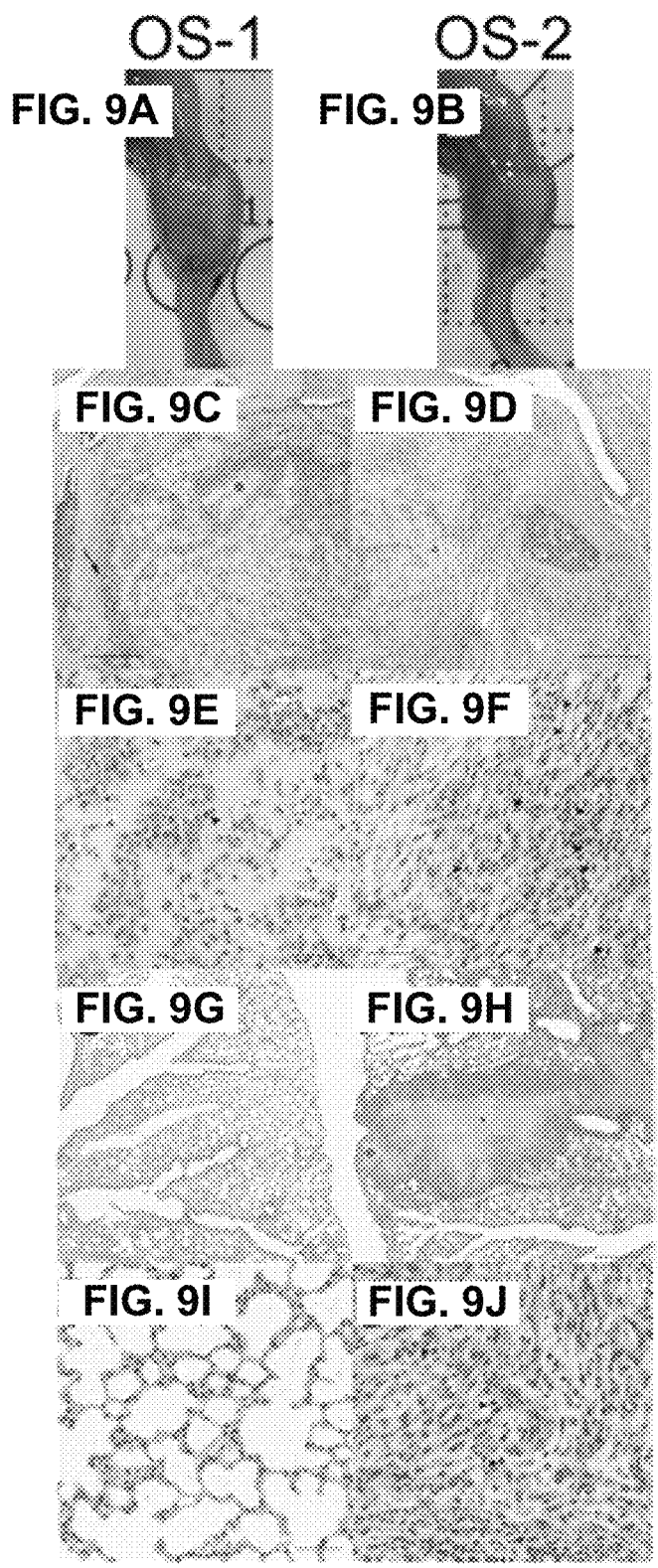

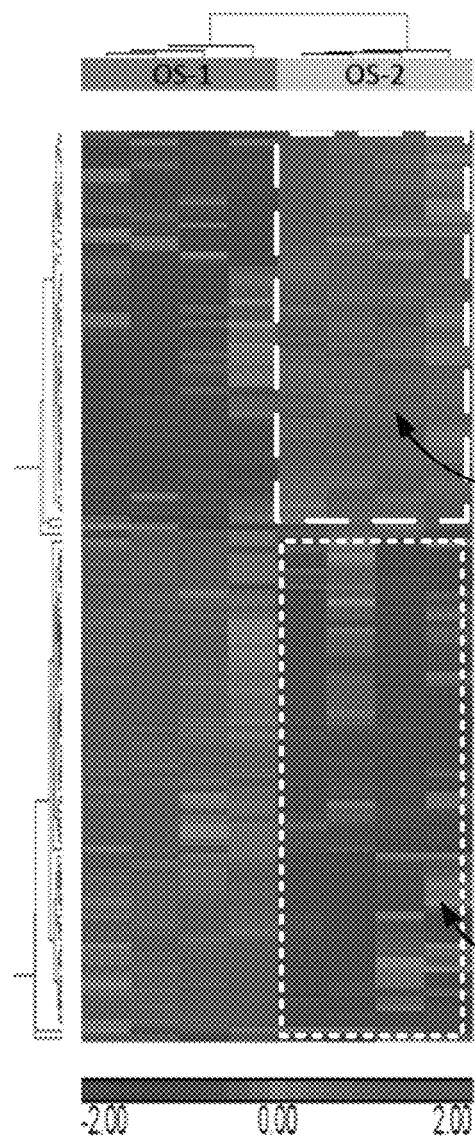
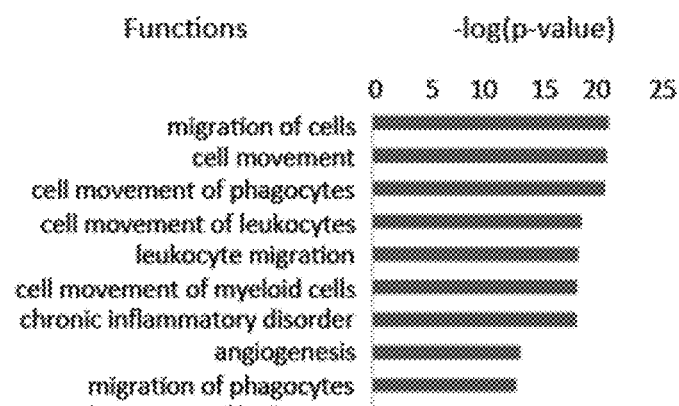
FIG. 21B
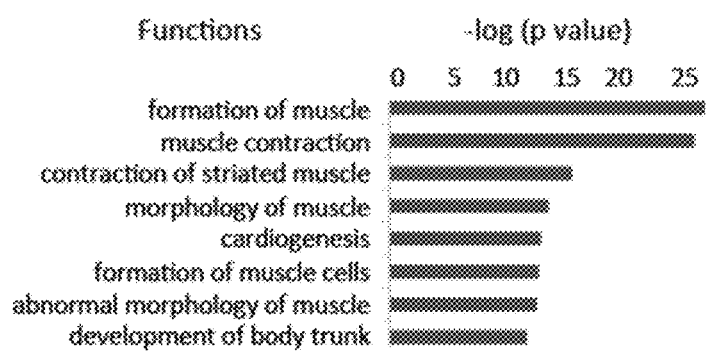
FIG. 21C
FIG. 21A

Metastatic Propensity of OS-1 and OS-2 Orthotopic Xenografts

| | Animals with Metastasis | |
|---|---|---|
| Time | OS-1<br>n=16 | OS-2<br>n=32 |
| Day 15 | | |
|   Number (%) | 0 | 1 (3.13) |
|   Total (%) | 0 | 1 (3.13) |
| Day 22 | | |
|   Number (%) | 0 | 1 (3.13) |
|   Total (%) | 0 | 2 (6.25) |
| Day 29 | | |
|   Number (%) | 0 | 2 (6.25) |
|   Total (%) | 0 | 4 (12.5) |
| Day 36 | | |
|   Number (%) | 1 (6.25) | 1 (6.25) |
|   Total (%) | 1 (6.25) | 5 (15.6) |
| Day 57 (histopathology) | | |
|   Total (%) | 2 (6.25) | 6 (18.8) |

FIG. 22

OS-1 and OS-2 Orthotopic Xenografts Show Differential Rate of Tumor Progression[1]

| Change in Volume (Affected tibia – Unaffected tibia) | | | *p-value* |
|---|---|---|---|
| Time | OS-1 n=16 | OS-2 n=32 | |
| Day 8 Median Mean (SD) | -8.03 -10.47 (18.6) | 8.17 4.61 (18.8) | |
| Day 15 Median Mean (SD) | -15.94 -13.87 (16.4) | -1.02 0.86 (21.8) | |
| Day 22 Median Mean (SD) | 1.45 0.83 (20.0) | 9.36 9.9 (16.2) | |
| Day 29 Median Mean (SD) | 1.54 3.73 (18.0) | 42.25 38.27 (26.0) | $p<0.001$ |
| Day 36 Median Mean (SD) | 12.42 17.60 (33.7) | 61.84 67.37 (38.8) | $p<0.001$ |
| Day 43 Median Mean (SD) | 39.62 35.31 (30.0) | 75.89 86.46 (53.2) | $p<0.01$ |
| Day 50 Median Mean (SD) | 69.41 90.14 (85.7) | 107.79 122.99 (65.74) | |
| Day 57 Median Mean (SD) | 137.22 140.3 (109) | 126.13 136.5 (78.6) | |

FIG. 23

MetaCore Analysis identifies Pathways for Murine Genes that Are Differentially Expressed between OS-1 and OS-2 Xenograft Tumors[1]

| Pathway | p-value |
|---|---|
| Immune response- Classical complement pathway | 5.70E-10 |
| Immune response- Lectin induced complement pathway | 4.23E-09 |
| Immune response- IL-17 signaling pathways | 3.57E-07 |
| Stimulation of TGF-beta signaling in lung cancer | 5.48E-06 |
| Cell Adhesion-ECM Remodeling | 1.02E-05 |
| Immune response- Alternative complement pathway | 1.18E-05 |
| Development- Transcription factors in segregation of hepatocytic lineage | 2.89E-05 |
| Cytoskeleton Remodeling- Regulation of actin cytoskeleton by Rho GTPases | 9.04E-05 |
| Complement Pathway Disruption in Thrombotic Microangiopathy | 1.00E-04 |
| Immune Response- IL-13 signaling via JAK-STAT | 2.70E-04 |

FIG. 24

Upstream regulators of differentially expressed murine genes in OS-2 relative to OS-1 xenograft tumors.[1]

| Upstream Regulator | Molecule Type | Predicted Activation State | Activation z-score | *p-value* of overlap |
|---|---|---|---|---|
| MTF1 | transcription regulator | Activated | 2.391 | 1.01E-08 |
| CEBPA | transcription regulator | Activated | 2.598 | 1.16E-08 |
| ELK1 | transcription regulator | Activated | 2.000 | 1.39E-02 |
| ARNT | transcription regulator | Activated | 2.408 | 1.72E-03 |
| XBP1 | transcription regulator | Activated | 2.155 | 1.88E-01 |
| RELA | transcription regulator | Activated | 2.372 | 2.30E-05 |
| MDM2 | transcription regulator | Activated | 2.000 | 2.32E-02 |
| KDM5A | transcription regulator | Activated | 3.742 | 2.45E-07 |
| NUPR1 | transcription regulator | Activated | 2.887 | 2.75E-01 |
| IRF8 | transcription regulator | Activated | 2.223 | 2.86E-02 |
| NFKB1 | transcription regulator | Activated | 2.201 | 3.94E-09 |
| STAT4 | transcription regulator | Activated | 2.472 | 5.06E-06 |
| CEBPD | transcription regulator | Activated | 2.566 | 5.21E-06 |
| CEBPB | transcription regulator | Activated | 2.360 | 5.54E-10 |
| FOXO1 | transcription regulator | Activated | 2.168 | 6.85E-04 |
| HIF1A | transcription regulator | Activated | 2.777 | 7.85E-13 |
| RBPJ | transcription regulator | Inhibited | -2.942 | 1.23E-03 |
| RB1 | transcription regulator | Inhibited | -2.765 | 1.25E-04 |
| MKL2 | transcription regulator | Inhibited | -2.646 | 2.08E-04 |
| MEF2C | transcription regulator | Inhibited | -3.138 | 2.54E-23 |
| HAND2 | transcription regulator | Inhibited | -2.975 | 2.84E-08 |
| MYOCD | transcription regulator | Inhibited | -2.897 | 3.86E-08 |
| FOXA2 | transcription regulator | Inhibited | -2.578 | 3.88E-07 |
| SPDEF | transcription regulator | Inhibited | -2.000 | 3.92E-02 |
| MYOD1 | transcription regulator | Inhibited | -3.878 | 5.83E-12 |
| SIRT1 | transcription regulator | Inhibited | -2.336 | 6.20E-08 |
| CBX5 | transcription regulator | Inhibited | -2.236 | 7.77E-02 |
| PRDM1 | transcription regulator | Inhibited | -2.015 | 8.43E-09 |
| SRF | transcription regulator | Inhibited | -3.050 | 8.59E-12 |

FIG. 25

Upstream regulators of upregulated murine genes in OS-2.[1]

| Upstream Regulator | Molecule Type | Predicted Activation State | Activation z-score | p-value of overlap |
|---|---|---|---|---|
| TGFB1 | growth factor | Activated | 3.566 | 1.26E-27 |
| IL1B | cytokine | Activated | 4.930 | 9.70E-25 |
| TNF | cytokine | Activated | 5.048 | 8.53E-23 |
| IL6 | cytokine | Activated | 4.559 | 9.03E-22 |
| OSM | cytokine | Activated | 3.974 | 1.76E-19 |
| IL1A | cytokine | Activated | 4.571 | 2.36E-19 |
| IFNG | cytokine | Activated | 3.995 | 5.25E-19 |
| STAT3 | transcription regulator | Activated | 2.037 | 4.47E-18 |
| IL17A | cytokine | Activated | 4.457 | 9.76E-18 |
| EGF | growth factor | Activated | 4.154 | 1.28E-17 |
| IL13 | cytokine |  | 1.939 | 1.17E-15 |
| JUN | transcription regulator | Activated | 3.486 | 1.26E-15 |
| NFKBIA | transcription regulator |  | 1.049 | 3.57E-15 |
| IL4 | cytokine |  | 1.418 | 4.38E-15 |
| IL1 | group | Activated | 4.111 | 5.52E-15 |
| HIF1A | transcription regulator | Activated | 3.672 | 6.04E-15 |
| FOS | transcription regulator | Activated | 2.013 | 9.40E-15 |
| IKBKB | kinase | Activated | 4.465 | 1.87E-14 |
| PDGF BB | complex | Activated | 4.590 | 1.95E-14 |
| S100A8 | other |  | 0.058 | 2.41E-14 |
| TREM1 | transmembrane receptor | Activated | 2.123 | 2.47E-14 |
| IL17RA | transmembrane receptor | Activated | 2.209 | 7.80E-14 |
| S100A9 | other |  | 1.189 | 1.11E-13 |
| Cg | complex | Activated | 2.426 | 1.31E-13 |
| Tgf beta | group |  | 1.086 | 3.75E-13 |
| EGFR | kinase | Activated | 2.610 | 6.01E-13 |
| TMEM173 | other | Activated | 2.611 | 6.30E-13 |
| NFkB (complex) | complex | Activated | 4.286 | 9.89E-13 |
| TGFBR2 | kinase |  | 0.966 | 1.21E-12 |

FIG. 26

Upstream regulators of downregulated murine genes in OS-2 relative to OS-1 xenograft tumors.[1]

| Upstream Regulator | Molecule Type | Predicted Activation State | Activation z-score | p-value of overlap |
|---|---|---|---|---|
| MEF2C | transcription regulator | Inhibited | -3.503 | 1.15E-24 |
| MYOD1 | transcription regulator | Inhibited | -4.158 | 2.16E-15 |
| SMTNL1 | other | Activated | 3.162 | 7.55E-14 |
| MYOCD | transcription regulator | Inhibited | -3.138 | 5.36E-09 |
| PTCH1 | transmembrane receptor | | 1.914 | 5.96E-09 |
| GATA4 | transcription regulator | Inhibited | -2.048 | 6.24E-09 |
| DMD | other | | -1.982 | 1.61E-08 |
| INSR | kinase | | -1.009 | 1.70E-08 |
| HAND2 | transcription regulator | Inhibited | -2.804 | 2.40E-08 |
| NOS2 | enzyme | Activated | 2.030 | 3.84E-08 |
| TRPS1 | transcription regulator | | -1.732 | 7.29E-08 |
| SRF | transcription regulator | Inhibited | -3.323 | 9.39E-08 |
| FGF8 | growth factor | | -1.066 | 2.30E-07 |
| TBX5 | transcription regulator | Inhibited | -2.795 | 2.65E-07 |

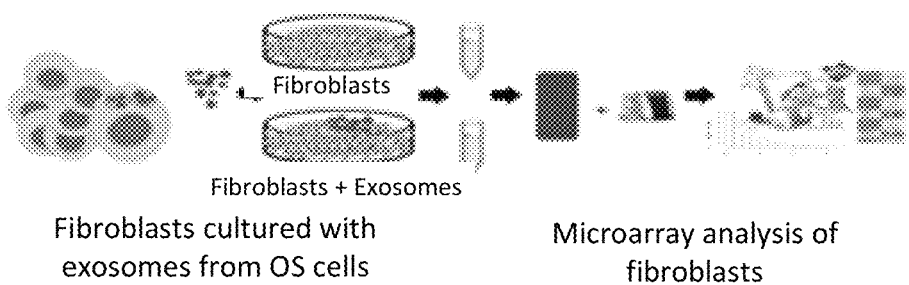

Fibroblasts cultured with exosomes from OS cells

Microarray analysis of fibroblasts

FIG. 29B

| Symbol | Log Fold Change |
|---|---|
| TNFSF18 | -2.7592735 |
| RORC | -2.5619092 |
| FAM118A | -2.499536 |
| SOX8 | -2.14114 |
| DHRS2 | 2.1159463 |
| KIAA0895L | 2.2143965 |
| USMG5 | 2.4831994 |
| ITGB1 | 3.3113837 |
| SYCE1L | 3.5635831 |

*No pathways of statistical significance after B-H correction

FIG. 29C

| Canonical Pathways | B-H p-value |
|---|---|
| Role of IL-17F in Allergic Inflammatory Diseases** | 1.22E-10 |
| Granulocyte Adhesion and Diapedesis | 1.88E-08 |
| Agranulocyte Adhesion and Diapedesis | 2.53E-08 |
| IL-17 Signaling** | 5.77E-08 |
| Differential Regulation of Cytokine Production in Macrophages and T Helper Cells by IL-17A and IL-17F | 6.50E-05 |
| TREM1 Signaling** | 1.25E-04 |
| Communication between Innate and Adaptive Immune Cells | 2.25E-04 |
| HGF Signaling | 3.95E-04 |
| PI3K/AKT Signaling* | 5.87E-04 |

**inactivated 484 differentially expressed mouse genes

Canine orthologs

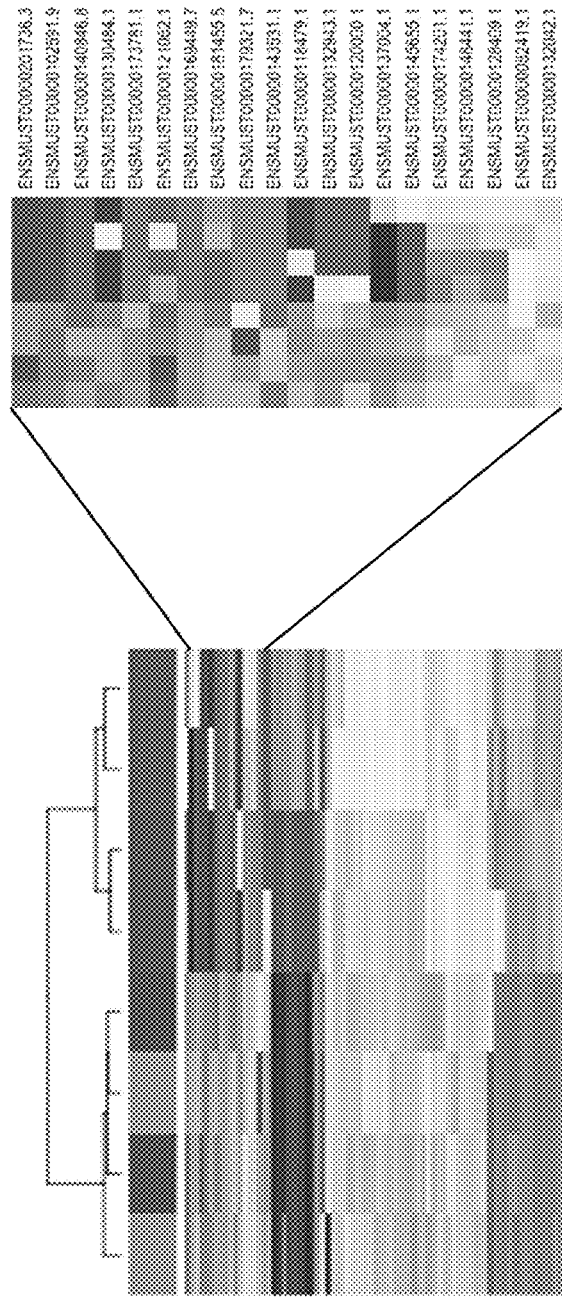
FIG. 33B
FIG. 33A
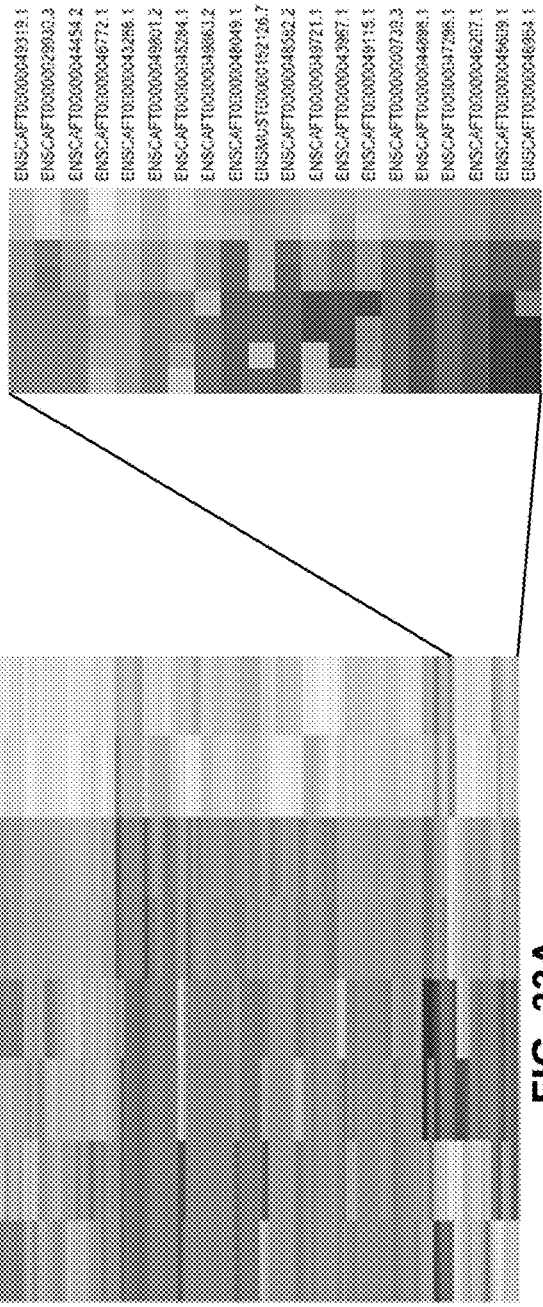
FIG. 33C

IDENTIFYING PRESENCE AND COMPOSITION OF CELL-FREE NUCLEIC ACIDS

This application claims the benefit of U.S. Provisional Patent Application No. 62/407,987, filed Oct. 13, 2016, the entire content of which being incorporated herein by reference.

TECHNICAL FIELD

This disclosure relates generally to methods for identifying and analyzing nucleic acids and, more particularly, methods for identifying and analyzing cell-free nucleic-acid biomarkers.

BACKGROUND

The composition and abundance of an organism's nucleic acids provide biomarkers indicative of various aspects of the organism's genome and transcriptional expression, including the organism's predisposition toward particular biological states, as well as the presence and progression of such biological states. Much of a living, multicellular organism's total nucleic acid complement is located intracellularly: DNA is chiefly located within the nuclei of the cells, whereas RNA of numerous types is abundant within the various organelles and cytoplasm of cells. Thus, nucleic acids may be derived from cells and used as biomarkers to determine a biological state of organism, such as the presence of a disease or the biological behavior of the disease. In applications such as xenografting, tissue from a donor animal may be grafted into a host animal, and then the biological behavior of the donor tissue may be evaluated in the host animal by analyzing nucleic-acid biomarkers derived from cells of the donor tissue.

SUMMARY

This disclosure describes example techniques and systems for determining the composition and abundance of nucleic acids in the blood of a host animal that has received a tissue xenograft and detecting biomarkers of a biological state via identification of the nucleic acids. Such techniques may include creating a combined reference genome that incorporates gene sequences from both the genome of the host animal and the genome of the xenograft donor animal. Cell-free nucleic acid sequences isolated from a blood sample of the host animal may then be aligned with the combined reference genome. In order to distinguish between sequences originating from the donor animal and those originating from the host animal, those sequences that align with a single region of the combined reference genome may be retained for further analysis. The retained sequences may then be analyzed to determine their identity, species of origin, abundance, and association with predetermined gene clusters that represent known biochemical pathways. In some examples, the techniques described herein may enable accurate identification and analysis of biomarkers associated with a biological state of xenograft donor tissue or xenograft host tissue based on a blood sample of the host animal, in part by eliminating from consideration confounding sequences originating from one of the host animal or the donor animal.

In one example, a method comprises obtaining a plurality of exosomes from a sample of bodily fluid derived from a first organism of a first species, wherein the first organism of the first species comprises tissue derived from both the first organism of the first species and tissue derived from a second organism of a second species, and wherein the plurality of exosomes comprises a plurality of molecules of ribonucleic acid (RNA); determining, for substantially each molecule of the plurality of molecules of RNA, a corresponding RNA sequence; determining, for each corresponding RNA sequence, whether the RNA sequence is substantially aligned with exactly one corresponding gene sequence of a combined reference genome; determining one or more characteristics of each RNA sequence substantially aligned with exactly one corresponding gene sequence of the combined reference genome, wherein the one or more characteristics include at least one of: a gene name of the corresponding gene sequence; a species associated with the corresponding gene sequence, wherein the species is one of the first species and the second species; determining an approximate number of times that each RNA sequence substantially aligned with exactly one corresponding gene occurs in the sample of blood; and determining, based on one or more of the one or more characteristics of each RNA sequence substantially aligned with exactly one corresponding gene sequence of the combined reference genome or the approximate number of times each RNA sequence substantially aligned with exactly one corresponding gene occurs in the sample of bodily fluid, whether the tissue derived from the second organism of the second species contains a biomarker indicative of at least one of a disease status, a response of the first organism of the first species to the tissue derived from the second organism of the second species, or a response of tissue derived from the second organism to transplantation within the organism of the first species.

In another example, a method comprises determining a corresponding RNA sequence for substantially each molecule of a plurality of molecules of ribonucleic acid (RNA), wherein a plurality of exosomes from a sample of bodily fluid derived from a first organism of a first species comprises the plurality of molecules of RNA, and wherein the first organism of the first species comprises tissue derived from both the first organism of the first species and tissue derived from a second organism of a second species; determining, for each corresponding RNA sequence, whether the RNA sequence is substantially aligned with exactly one corresponding gene sequence of a combined reference genome; determining one or more characteristics of each RNA sequence substantially aligned with exactly one corresponding gene sequence of the combined reference genome; and determining an approximate number of times that each RNA sequence substantially aligned with exactly one corresponding gene occurs in the sample of bodily fluid; and determining, based on one or more of the one or more characteristics of each RNA sequence substantially aligned with exactly one corresponding gene sequence of the combined reference genome or the approximate number of times each RNA sequence substantially aligned with exactly one corresponding gene occurs in the sample of bodily fluid, whether the tissue derived from the second organism of the second species contains a biomarker indicative of at least one of a disease status, a response of the first organism of the first species to the tissue derived from the second organism of the second species, or a response of tissue derived from the second organism to transplantation within the first organism of the first species.

In another example, a system comprises a reservoir configured to receive a sample of bodily fluid; and processing circuitry configured to: determine a corresponding RNA sequence for substantially each molecule of a plurality of molecules of ribonucleic acid (RNA), wherein a plurality of exosomes from the sample of bodily fluid is derived from a first organism of a first species and comprises the plurality of molecules of RNA, and wherein the first organism of the first species comprises tissue derived from both the first organism of the first species and tissue derived from a second organism of a second species; determine, for each corresponding RNA sequence, whether the RNA sequence is substantially aligned with exactly one corresponding gene sequence of a combined reference genome; determine one or more characteristics of each RNA sequence substantially aligned with exactly one corresponding gene sequence of the combined reference genome; determine an approximate number of times that each RNA sequence substantially aligned with exactly one corresponding gene occurs in the sample of bodily fluid; and determine, based on one or more of the one or more characteristics of each RNA sequence substantially aligned with exactly one corresponding gene sequence of the combined reference genome or the approximate number of times each RNA sequence substantially aligned with exactly one corresponding gene occurs in the sample of bodily fluid, whether the tissue derived from the second organism of the second species contains a biomarker indicative of at least one of a disease status, a response of the first organism of the first species to the tissue derived from the second organism of the second species, or a response of tissue derived from the second organism to transplantation within the first organism of the first species.

The details of one or more example are set forth in the accompanying drawings and the description below. Other features, objects, and advantages will be apparent from the description and drawings, and from the claims.

BRIEF DESCRIPTION OF DRAWINGS

FIGS. 9A-9J are graphical representations of data pertaining to the application of the techniques described herein to the OS-1/OS-2 xenograft example.

FIGS. 21A-21C are graphical representations of data gathering and analysis techniques in accordance with the examples of this disclosure, as applied to the OS-1/OS-2 xenograft example.

FIGS. 22-27 illustrate tables providing additional information pertaining to the application of the techniques described herein to the OS-1/OS-2 xenograft example.

FIGS. 29A-29C are graphical representations of a workflow by which RNA contents of OS-derived exosomes from cultured cells may be defined, and outcomes of example data analyses performed on data derived from the workflow indicating that decreased expression of cytokines may be found in fibroblasts treated with OS-2 derived exosomes.

FIG. 33A-33C are is graphical representations of 198 differentially expressed transcripts.

FIGS. 34A-34D are graphical representations of the detection of biomarkers of disease and host response.

DETAILED DESCRIPTION

Figure 1:
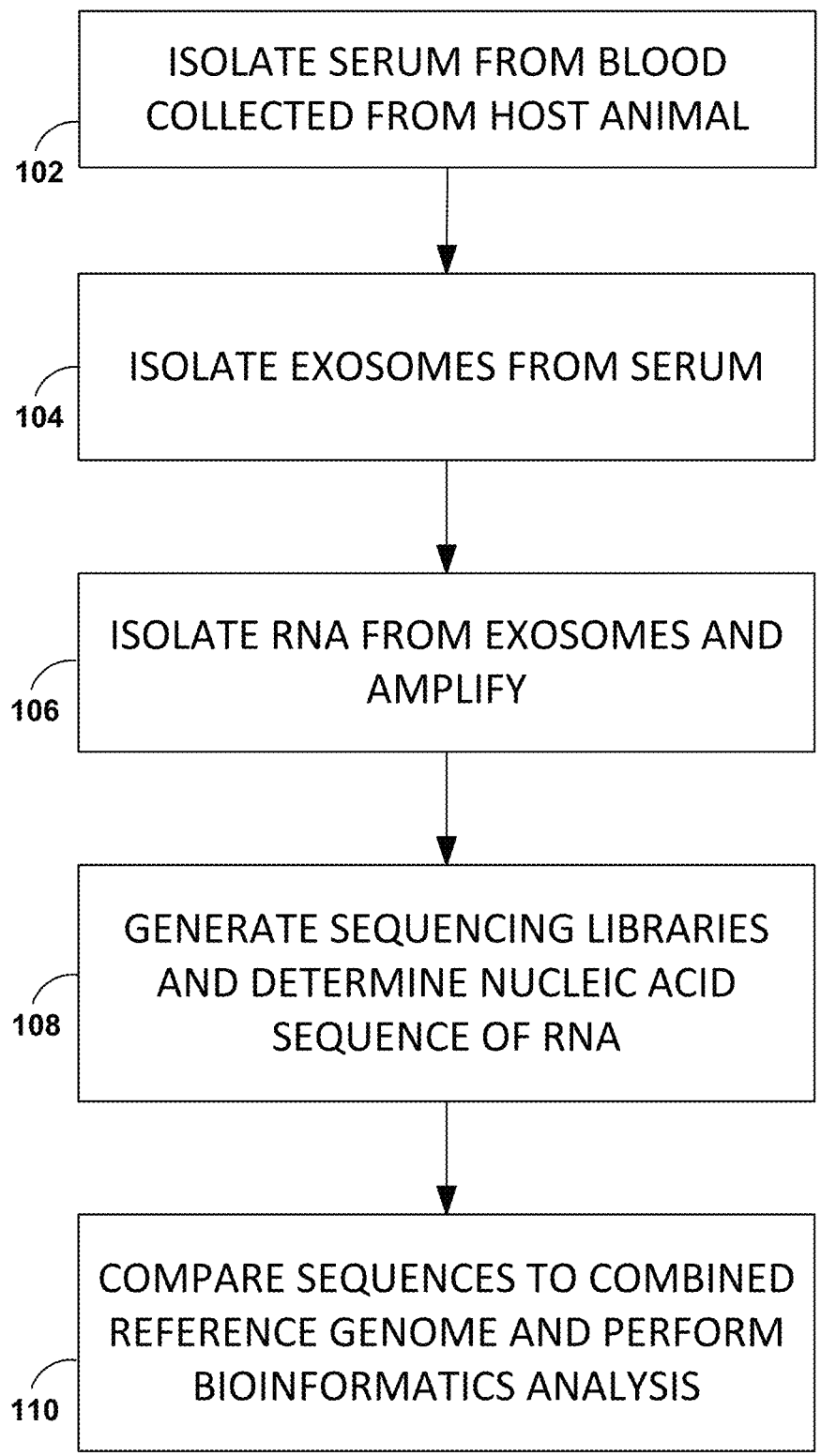
FIG. 1 is a flow diagram illustrating an example technique in accordance with the examples of this disclosure.

Favorable clinical outcomes of many medical conditions depend, to varying degrees, on factors such as the accurate prediction of a patient's risk of a condition or disease, reliable testing for early detection of the condition or disease, accurate prediction of disease progression, or the selection and administration of appropriate therapies. In some cases, the composition and abundance of nucleic acids present in the patient's tissue may be used as one or more biomarkers corresponding to the patient's risk of the condition or disease, or to the presence, progression, or potential response of the condition or disease to a particular therapy. Identification of such biomarkers present in the patient's tissue thus may facilitate one or more interventions associated with a favorable clinical outcome of the patient.

At present, diagnostics and interventions based on nucleic-acid biomarkers largely rely on the identification of single nucleic-acid biomarkers, which may be identified based on cells derived from tissue samples (e.g., tumor biopsies) obtained from multiple patients having a particular disease. Tissue samples from another patient then may be analyzed to determine whether the biomarker is present in the sample. While some such biomarkers pass predetermined statistical thresholds for biomarker identification, the use of single biomarkers in diagnosis and treatment-selection is subject to several drawbacks. For example, in the case of a particular type of cancer, there may be inherent genetic heterogeneity within tumors in individual patients and among different patients with the same type of cancer. Due to such heterogeneity, analysis of a tissue sample from a patient may lead to a false-negative diagnosis that the patient does not have the particular type of cancer because the single biomarker was not detected in the tissue sample.

In addition, methods for identifying and detecting biomarkers based on nucleic acids from cells derived from tissue samples are subject to their own limitations. For example, such methods limit the scope of inquiry to the tissue samples themselves. Although nucleic-acid biomarkers identified in tissue samples (e.g., tumor biopsies) may indicate the presence of a disease or condition, such biomarkers do not reflect aspects of the disease or condition that occur outside of the sampled tissue. For example, while much of a cell's nucleic acids are located within the cell, some nucleic acids, such as RNA, can be transported out of the cell inside vesicles called exosomes. In particular, cell-free RNA may be found in the bloodstream of animals inside exosomes.

The RNA contained within exosomes may be indicative of its parent cell's transcription profile, and may provide biomarkers indicative of a patient's biological state. For example, the RNA contained within exosomes found within a patient's bloodstream may be indicative of one or more of the patient's risk of developing a condition or disease, the presence of the condition or disease, the progress of the condition or disease, or the potential future progress of the condition or disease. Indeed, some species of RNA contained within exosomes may be indicative of a metastatic cancer phenotype (i.e., that a cancerous condition is likely to metastasize), and may indicate that a process of metastasis of a primary tumor has begun. Such species of RNA may be microRNAs, which may be packaged into exosomes, secreted from a tumor cell into the bloodstream of an organism, and disseminated to distant tissue sites. Once such microRNAs have infiltrated a distant tissue site, they may perform a signaling or conditioning function that causes non-cancerous cells at the distant tissue site to undergo changes that make the tissue site more favorable to colonization by tumor cells.

In some examples, monitoring of the composition and abundance of such RNA species present within the bloodstream of a patient may reveal a progressive increase in the abundance of such RNA species, which in turn may serve as a biomarker of progress of a cancerous condition toward metastasis. Such findings may inform a clinician's decision to select a particular type of therapy over another type of therapy, as different types of therapy may be predictable more appropriate at different stages of the condition or disease.

Thus, a complement of multiple cell-free nucleic acid biomarkers derived from blood may provide a better indicator of the presence, progress and future progression of a condition or disease than nucleic acid biomarkers derived from cells taken from a tissue sample. The collection of blood samples for the detection and analysis of cell-free nucleic acid biomarkers may be less invasive, costly, and time consuming than tissue biopsies and/or imaging procedures that may be involved in the detection of nucleic acid biomarkers from tissue samples. Thus, diagnostic and treatment-selection methods based on the detection of cell-free nucleic acid biomarkers derived from exosomes present in a patient's bloodstream may provide numerous clinical benefits over interventions based on the detection of a single nucleic acid biomarker derived from cells.

Described herein are example techniques and system for cell-free nucleic acid biomarker identification that may be used to account for the genetic heterogeneity of many conditions and diseases, as well as example methods for detecting such biomarkers within the blood of a patient. Such methods may be used for virtually any disease or condition for which there are cell lines that grow as xenografts, or patient derived xenografts that reflect the expected variance in a disease or condition. One method involves the use of gene cluster expression summary scores. These scores account for coordinated transcriptional regulation of multiple genes, overcoming deficiencies of single biomarkers. Another method includes the use of reconstructed hybrid genomes (e.g., mouse host and tumor donor species) and bioinformatics approaches to identify mRNAs expressed exclusively in the tumor cells (donor) and mRNAs expressed exclusively in supporting stromal cells (host). Such methods may distinguish mRNAs present in donor-derived exosomes from mRNAs present in host-derived exosomes, enabling a novel means to identify candidate biomarkers. Because the approach is not restricted to identification of donor-derived exosomes, it can also measure biomarkers of host response as well as biomarkers that can define response to therapy. The example methods described herein thus may provide efficient and cost-effective ways to discover biomarkers that can inform the risk of diseases or conditions, their diagnosis and prognosis, may be used to predict response to therapy, and may be rapidly validated in patient samples.

In some methods described herein, identification of cell-free nucleic acid biomarkers may be conducted via xenograft procedures. In such procedures, a tissue sample may be obtained from a donor animal of a first species. Whole tissue or cell lines cultured from the tissue sample may then be grafted into a host animal of another species. In some examples, the tissue sample or cell lines derived from the donor animal may be derived from tissue harboring a disease or condition, such as tissue from a cancerous tumor. In such examples, healthy tissue or cell lines derived from another donor animal may be introduced into another host animal as a control. In other examples, the tissue derived from the donor animal may be healthy organ tissue, and it may be desirable to identify cell-free nucleic acid biomarkers associated with a response of the host tissue and/or the donor organ tissue to a graft procedure. In either example, blood samples subsequently may be obtained from the host animal, from which exosomes containing RNA may be extracted. The RNA then may be sequenced, quantified, and aligned with a hybrid genome prepared by combining the genome of the donor-animal species and the host-animal species. In order to distinguish RNA sequences derived from the donor species from RNA sequences derived from the host species, sequences derived from the respective species may be analyzed separately. In examples in which cell-free nucleic acid biomarkers of a disease or condition are to be determined, donor sequences resulting from control donor animals also may be compared to donor sequences resulting test donor animals. RNA sequences that are differentially expressed in the tissue derived from the control donor animals and the tissue derived from the test donor animals may be identified as biomarker sequences for use in disease diagnosis or analysis of disease behavior. Similarly, RNA sequences that are differentially expressed in instances of organ-tissue acceptance or rejection by the host animals may be identified as biomarker sequences for use in analysis of organ-transplant feasibility.

In other examples, a biological status associated with a particular biomarker may be associated with acceptance or rejection of the tissue of the donor animal by the body of a host animal. Example techniques described herein also may include identifying a predisposition toward a particular biological state of the donor animal based on the presence of a biomarker, such as a predisposition toward acceptance or rejection of donor tissue. In other examples, such techniques may include identifying targeted therapies based on the presence of a biomarker that indicates that the body of the host animal is accepting or rejecting the tissue of the donor animal, such as in the case of organ tissue transplanted into the host animal to assess the long-term feasibility of organ transplant from the donor animal into a different host animal of yet another species.

For the sake of illustration, the example techniques described herein are described within the context of an example in which the host animal is a mouse harboring cells associated with a disease of humans or companion animals, such as cells derived from a canine osteosarcoma tumor. The xenografts described in the example presented herein represent two molecular phenotypes of osteosarcoma (OS-1 and OS-2) with distinct biological behavior that are highly conserved between dogs and humans. However, it should be understood that the example techniques may be used in the identification and detection of biomarkers associated with other diseases or conditions of humans or other animal species.

Osteosarcoma (OS) is a heterogeneous disease with a disproportionate human impact, as it mainly affects children and adolescents, and is the most common malignant pediatric tumor of bone. Standard therapy for OS comprises neoadjuvant chemotherapy, surgery and adjuvant chemotherapy. The 5-year survival rates of OS patients with localized and operable OS is 60-70%, but the outcome of patients with non-resectable or metastatic OS is poor, as more than half of patients with OS succumb to metastatic disease.

OS is also the most common primary malignant tumor of bone in dogs, and it is particularly prevalent in large and giant breeds. OS is an incurable, highly prevalent cancer of large and giant breed dogs that has been identified as a high priority for health research by over 25 AKC Parent breed clubs. In contrast to humans, OS occurs most commonly in older dogs. The number of diagnoses per year has been estimated at >8,000, and possibly as high as 80,000 in the US, with the lifetime risk for OS in some breeds being as high as 1 in 5 to 1 in 7. Similarly to humans, the outcome of canine patients with metastatic OS is poor. Tumors at the primary site may be managed surgically, but most dogs with OS die from metastasis to lungs or to other bones or organs.

These collective statistics illustrate that progress in managing OS has been hindered by its heterogeneity in both humans and in dogs. For example, neither the histological appearance nor the propensity of the tumor cells to elaborate bone, cartilage, or collagen matrices are predictive of behavior, and while recurrent molecular events have been described, these are yet to be adopted as prognostic or predictive biomarkers for this disease. Thus, clarification of the etiology of the disease, development of better strategies to manage disease progression, and methods to guide personalized treatments are among the unmet health needs for both human OS patients and canine patients. These needs may be met by models (e.g., models in species other than humans or canines) that accurately recapitulate the natural heterogeneity of OS in both humans and in dogs. Such models may provide a better understanding of the events that underlie OS tumor heterogeneity and contribute to disease progression may enable the development of effective strategies to manage OS and to improve outcomes. In some cases, a single model may be applicable to both humans and dogs, because spontaneous OS may be a homologous cellular and molecular disease of humans and dogs. For example, prognostically significant gene- and microRNA-expression signatures have been discovered that are evolutionarily conserved in human and canine OS. Such expression signatures may predict both the biological behavior OS and patient survival. While not necessarily linked to metastatic potential, the molecular components of such gene and microRNA expression profiles may reflect tumor growth, invasive potential, time to metastasis, or patient response to therapy.

Techniques for modeling OS to obtain a better understanding of OS disease-events in are within the scope of this disclosure and are described in further detail below. Such techniques also may enable a better understanding of events that occur in other diseases, such as other diseases that may affect dogs, other non-human animals, or humans. In addition, such techniques may enable a better understanding of events that occur in other medical situations, such as in tissue-transplant or other situations.

In the example described below with respect to FIGS. 7A-34D, the techniques may be illustrated with respect to orthotopic xenografts of canine osteosarcoma in nude mice, or with respect to cells cultured with exosomes derived from OS-1 or OS-2 tumors. In this case, potential biomarkers for disease include nucleic acids (genes) indicative of osteosarcoma (canine origin), nucleic acids indicative of biological behavior and/or progression for specific osteosarcomas (canine origin), and nucleic acids indicative of host response to bone invasion, host response to osteosarcoma in general, and response to distinct osteosarcomas with different biological behavior in particular (all of murine origin).

In some examples, cells used for xenografts are called OS-1 (OSCA-32) and OS-2 (OSCA-40). Such cells may be derived from canine tumors with distinct biological behavior and recapitulate this behavior in xenografts. In this example, the cross-species hybrid genome approach may be used to identify separate canine and mouse sequences from tumor xenografts that inform the progression of disease (in the mouse). Thus, it is possible to use tumor samples grown in mice to determine the contribution of dog sequences (derived from the implanted, growing tumor cells) and mouse sequences (derived from infiltrating stroma) to define features of progression for tumors arising from implantation of the different cell lines. In the following description, references are made to illustrative examples. It is understood that other examples may be utilized without departing from the scope of the disclosure.

FIG. 1 is a flow diagram illustrating an example technique according to this disclosure. At block 102, serum may be isolated from blood collected from mice at a "time 0," i.e., prior to any manipulation. In some examples, experimental groups may include: mice injected intra-tibially with PBS (phosphate-buffered saline), with no cells, i.e., control for host response to intratibial injection and possible consequent inflammation; mice injected intra-tibially with OS-1 cells; and mice injected intra-tibially with OS-2 cells. In this example, serum may be isolated from blood collected from mice in each group every two weeks for up to 8 weeks. For each group, there may be two cages of 4 mice each. Each cage may be an experimental replicate (blood pooled from all the mice in the cage to isolate sufficient serum for exosomes; furthermore, blood may be pooled for analysis from weeks 2, 4, 6, and 8 for each cage, although aliquots may be preserved from the pool for each week for validation by qRT-PCR).

Exosomes may first be isolated from the serum (102). In some examples, this may be accomplished by using Exo-Quick kits from System Biosciences, Inc. (SBI), although other suitable techniques may be used.

Next, total RNA may be isolated from the exosomes (104). For example, this may be accomplished by using the Complete SeraMir Exosome RNA Amplification kit from SBI and precipitated with the Dr. GenTLE (Gene Trapping by Liquid Extraction) System from SBI, although other suitable techniques may be used.

Sequencing libraries may be generated (108) from the RNA by using Nextera XT DNA Library Preparation Kit (Clontech) at the University of Minnesota Genomics Center (UMGC), although other suitable techniques and facilities may be used. In some examples, sequencing-library preparation may include RNA purification, reverse-transcriptase PCR production of cDNA from the RNA molecules, PCR amplification of the resulting cDNA molecules, and transcription of the cDNA molecules into RNA. Sequencing may be done at UMGC on a 50 base-pair paired-end (PE) run on a HiSeq 2500 nucleic acid sequencing instrument using Rapid chemistry. In some examples, it may be desirable to use 8 samples per lane and generate >120 M reads, which may be fairly well balanced across projects. Preferably, average quality scores may be above Q30 for all PE reads.

The sequences obtained at block 106 are then compared to a cross-species hybrid genome is performed, followed by bioinformatic analyses (110). A summary of example bioinformatics methods for creation and mapping to cross-species hybrid genome and the workflow of data analysis steps with illustrations is described below.

Figure 2:
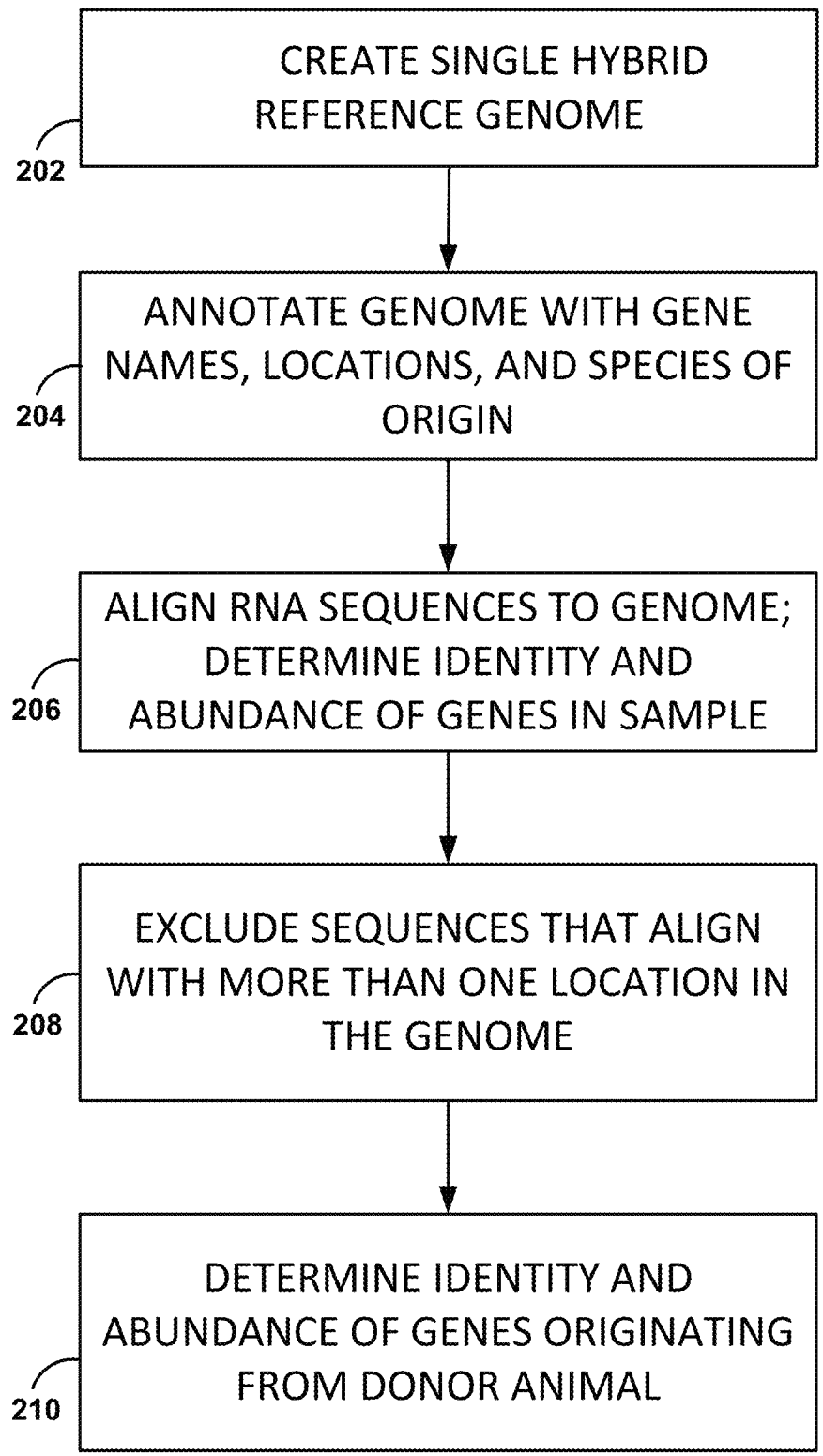
FIG. 2 is a flow diagram illustrating an example technique in accordance with the examples of this disclosure.

FIG. 2 is a flowchart illustrating an example bioinformatics method according to this disclosure. It will be summarized here with respect to FIG. 2 and described in greater detail below. First, a single hybrid reference genome for two species may be created by combining the reference sequences of all chromosomes of each species into one file, with chromosome names modified to indicate the species of origin (202). Next, a single hybrid genome annotation file describing the locations of genes in the genome may be created by combining the annotation of each species into one file, with chromosome and gene names modified to indicate the species of origin (204). A sequence alignment program such as HISAT2 may be used to align RNA-Seq sequence reads to the hybrid genome (206). Most reads will map uniquely to a chromosome of one of the species. Some parts of the genomes will be identical in both species resulting in a small number of multi-mapped reads mapping to two chromosomes, one from each species, although longer sequence reads reduce the number of multi-mapped reads. The presence and abundance levels of genes are determined by comparing the genomic location of each uniquely aligned read with the genomic locations of genes in the hybrid annotation file and summing the number of reads aligning to each gene.

Next, multi-mapped genes are excluded from the analysis (208). Excluding multi-mapped reads from the abundance estimation step may be useful to help avoid incorrectly identifying the presence of graft-derived nucleic acids. Aligning RNA-Seq reads only to the reference genome of the graft species may result in the spurious identification of graft-derived genes in cases where the genes have identical sequences in both species. It may be desirable to compare gene expressions levels from a xenograft sample with a negative control sample way provide further power to reduce false-positives. The identity and abundance of genes originating from the donor animal, which in this example may be a dog, is then determined (210). As described in further detail below, the determined identity and abundance of genes originating from the donor animal may be used to determine the presence of disease and disease progression, and may inform treatment decisions.

Figure 3:
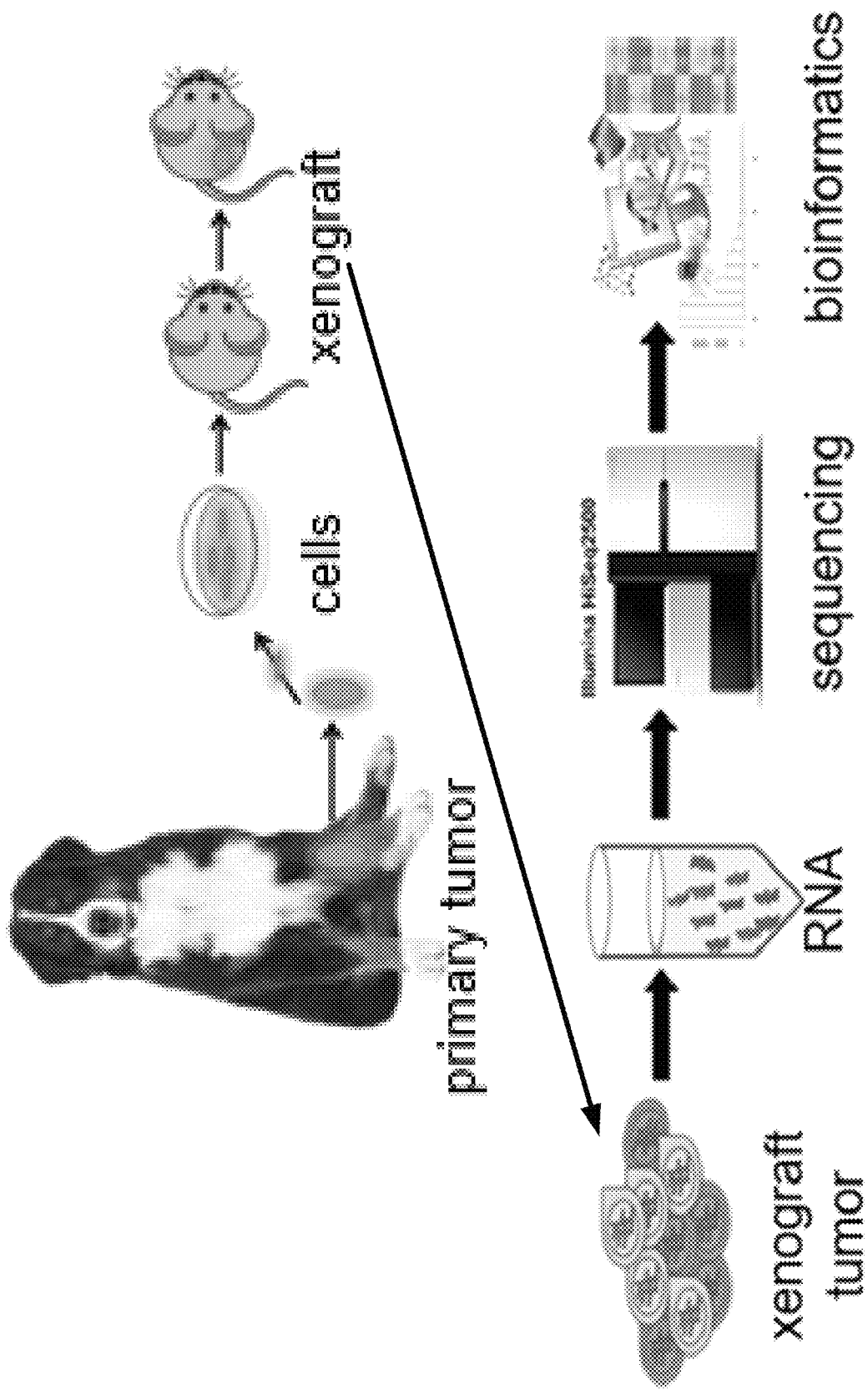
FIG. 3 is flow diagram illustrating an example technique in accordance with the examples of this disclosure.

FIG. 3 is a graphical representation related to the techniques described with respect to the flowcharts of FIGS. 1 and 2. Specifically, FIG. 3 provides an overview of the techniques described with respect to the flowcharts of FIGS. 1 and 2 within the context of a dog-to-mouse xenograft, where the dog harbors a primary tumor. However, FIG. 3 is illustrative in nature, and provides a broad overview of the techniques described herein. Other species may be substituted for the dog and mouse illustrated in FIG. 3, for example, such as other murine species, rodent species, feline, porcine, or non-human primate species. In addition, in some examples, the donor organism may be a human. In the example of FIG. 3, a first organism of a first species (e.g., a dog donor-organism) may harbor diseased tissue such as a primary tumor. A clinician or experimenter may obtain cells from the primary tumor of the dog donor-organism and introduce the cells into a second organism of a second species (e.g., a mouse host-organism) in a xenograft process. Next, the cells from the primary tumor of the dog donor-organism may be allowed to grow and form a xenograft tumor within the mouse host-organism. Thereafter, the clinician or experimenter may obtain a sample of bodily fluid (e.g., blood or blood serum) from the mouse host-organism. Exosomes containing RNA molecules then may be isolated from the sample of bodily fluid, such as by the clinician or experimenter, or by a suitable instrument, and the RNA molecules contained within the exosomes may be sequenced (e.g., by next-generation or other sequencing techniques) to determine a sequence for substantially each molecule of RNA. Bioinformatics analysis then may be performed on the RNA sequences. In some examples, the bioinformatics analysis may be performed by a system that includes processing circuitry (as described below with respect to FIGS. 4 and 5), as well as a suitable receptacle or reservoir configured to receive the sample of bodily fluid.

The bioinformatics analysis illustrated in FIG. 3 may include determining whether each RNA sequence is substantially aligned with exactly one corresponding gene sequence (e.g., a coding or regulatory sequence) of a combined reference genome that includes the genomes of both the dog donor-organism and the mouse host-organism, and determining an approximate number of times that each RNA sequence that aligns with the combined reference genome occurs in the sample of bodily fluid. One or more of the characteristics (e.g., a gene name or a species) of the RNA sequences that align with the combined reference genome or the number of times that such RNA sequences occur in the sample of bodily fluid then may be used to determine whether the sample of bodily fluid contains a biomarker (e.g., a nucleic acid sequence) associated with a disease status of the dog donor-organism.

In some examples, a disease status may be a predisposition to a disease, the presence of a disease, or the progress or potential progression of a disease of the dog donor-animal. In some examples, the disease status may enable a clinician or experimenter to select an appropriate treatment for the dog donor-organism or the mouse host-organism. In other examples, instead of a disease status, the bioinformatics analysis may indicate a response of the mouse host-organism to non-diseased cells or tissue derived from the dog donor-organism, or a response of the non-diseased cells or tissue derived from the dog donor-organism to transplantation within the mouse host-organism. In such examples, the characteristics of the RNA sequences that align with the combined reference genome or the number of times that such RNA sequences occur in the sample of bodily fluid then may be used to determine whether the dog-donor organism is a good candidate to receive a tissue transplant (e.g., an organ transplant).

In some examples, the bioinformatics analysis illustrated in FIG. 3 may include a determination that one or more of the RNA sequences that correspond to exactly one gene sequence are associated with a predetermined cluster of genes. Such clusters of genes may be groups of genes that share one or more functional characteristics. The functional characteristics of the gene clusters may include one or more biological processes or canonical pathways, such as one or more of transcriptional regulation, intracellular signaling, intercellular signaling, cell apoptosis, biomolecule metabolism, biomolecule synthesis, RNA processing, or macromolecule assembly. The example technique broadly illustrated in FIG. 3 will be discussed in greater detail below with respect to FIGS. 7A-34D.

Figure 4:
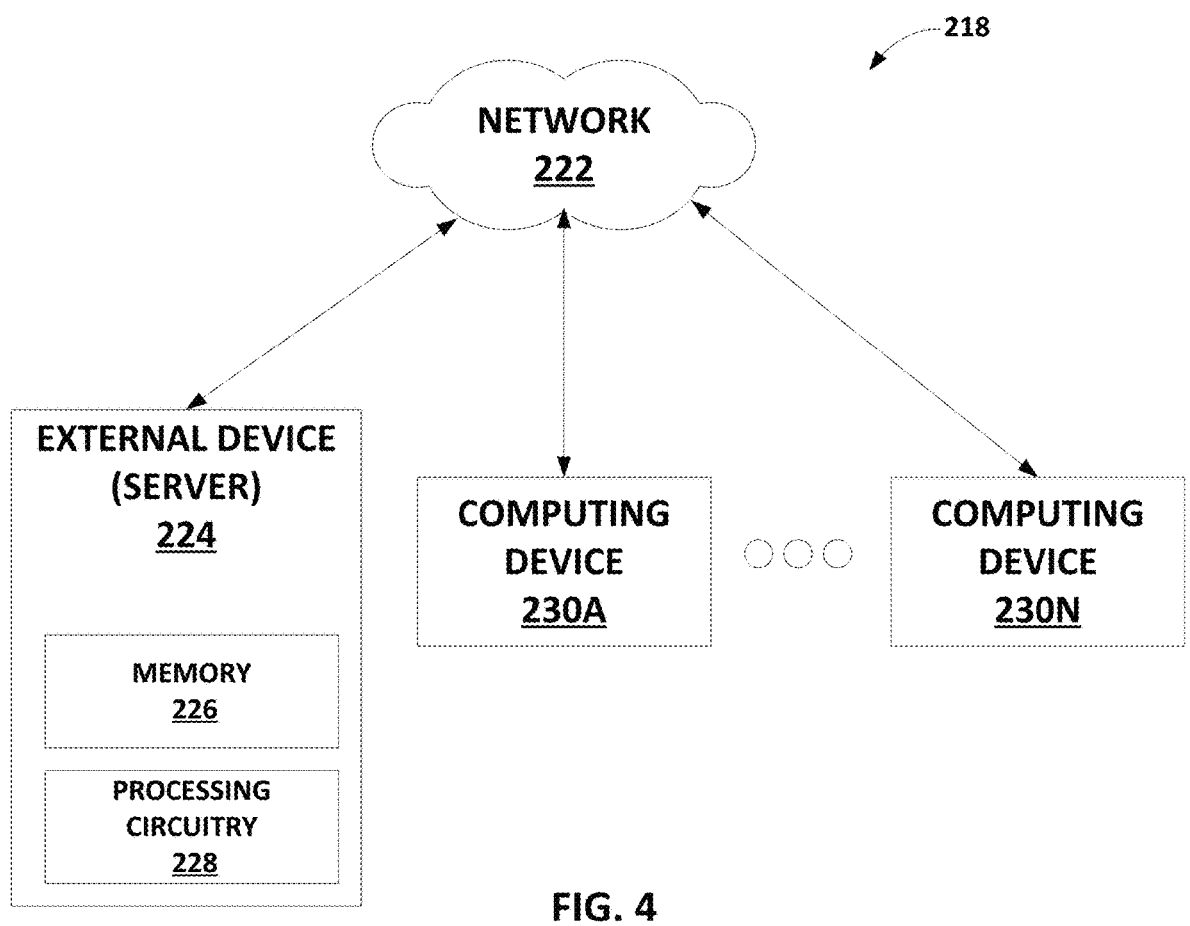
FIG. 4 is functional block diagram illustrating an example system that may be used to implement the techniques described herein, which may include remote computing devices, such as a server and one or more other computing devices, that are connected to one or more external devices via a network.
Figure 5:
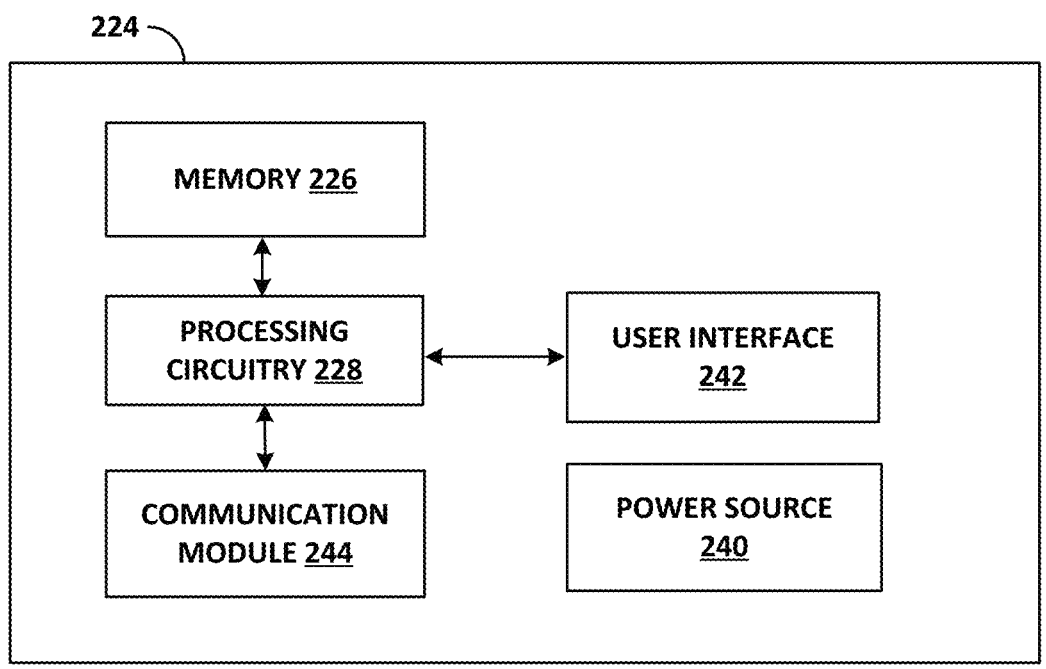
FIG. 5 is a functional block diagram further illustrating the external server in the example system of FIG. 4 that may be used to implement the techniques described herein.

As illustrated in FIGS. 4 and 5, various aspects of the techniques described herein may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

FIGS. 4 and 5 are functional block diagrams of an example system 218 configured to perform the techniques described in accordance with the disclosure. In the example illustrated in FIG. 4, one or more computing devices 230A-230N are connected to network 222. In some examples, an external server device, such as server device 224, may also be connected to network 222. The server device 224 shown in FIGS. 3 and 4 may include processing circuitry 228, memory 226, user interface 242, communication module 244, and power source 240. Processing circuitry 228 may include one or more processors. In one example, processing circuitry 228 is configured to run the software instructions in order to control operation of system 218. Processing circuitry 228 can include one or more processors, including one or more microprocessors, digital signal processors (DSPs), application specific integrated circuits (ASICs), field programmable gate arrays (FPGAs), or any other equivalent integrated or discrete logic circuitry, as well as any suitable combination of such components. The term "processor" or "processing circuitry" may generally refer to any of the foregoing logic circuitry, alone or in combination with other logic circuitry, or any other equivalent circuitry.

Memory 226 may include any volatile or non-volatile media, such as a random access memory (RAM), read only memory (ROM), non-volatile RAM (NVRAM), electrically erasable programmable ROM (EEPROM), flash memory, and the like. As mentioned above, memory 226 may store information including instructions for execution by processing circuitry 228 such as, but not limited to, instructions for performing the techniques described herein. Communication module 244 may provide one or more channels for receiving and/or transmitting information. Communication module 244 may be configured to perform wired and/or wireless communication with other devices, such as radio frequency communications. In other examples, communication module 244 may not be implemented, and instead, memory 226 may be removable (e.g., a removable flash memory).

Power source 240 delivers operating power to various components of computing device 218. Power source 240 may generate operational power from an alternating current source (e.g., residential or commercial electrical power outlet) or direct current source such as a rechargeable or non-rechargeable battery and a power generation circuit to produce the operating power. In other examples, non-rechargeable storage devices may be used for a limited period of time.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Further aspects of the disclosure will now be discussed, including further details of the techniques described herein. The example laboratory techniques described herein for accomplishing routine laboratory tasks, such as the collection of blood and the isolation of serum from blood, as well as others, are not intended to be limiting and may be performed by any suitable laboratory techniques. In addition to the techniques described above, supplementary techniques, as described below, may be employed. The example techniques described herein may be used to identify cell-free transcripts or other nucleic acids in blood that are specifically associated with the particular tumor and the host response, thereby creating sets of biomarkers with distinct diagnostic utility. In some examples, the human or animal disease may be re-created in a mouse (xenograft, xenotransplants), and to recognize that certain components of the response will be absent when immunodeficient mice are used (for example, the host T-cell component in athymic nude mice).

Tumor cells may regularly enter the circulation. Most of these cells die because they fail to adapt to conditions of growth outside the tumor niche. However, rare cells survive at distant sites and re-establish a niche that is suitable for tumor growth. It is known that tumors with different metastatic potential (including OS) display distinct patterns of gene expression, which may be derived from tumor cell-autonomous properties, but may be influenced by the local tumor microenvironment (TME) stratification of OS into prognostically significant groups. Canine and human OS may be stratified into more and less aggressive groups based on their molecular signatures. The differences in behavior among these subtypes of OS are intrinsic—that is, they are not entirely due to therapeutic management. Moreover, while OS generally has high potential to metastasize, somewhere between 30-40% of children and 10%-25% of dogs treated for this disease, respectively, will survive more than 10 years and more than 2 years. Thus, some tumors metastasize more slowly than others, and this may true for tumor xenografts in immunodeficient mice.

The example described herein illustrates that OS-2 xenografts may have a greater propensity to disseminate to the lung than OS-1 xenografts. Highly expressed genes present in stromal cells of OS-2 xenograft tumors are associated with inflammation and immune response. In addition, pulmonary fibroblasts treated with OS-2 exosomes show decreased expression of chemokines that are strongly chemotactic for lymphocytes and that establish an environment favoring polarization to the Th17 phenotype. OS-2 derived exosomes contain genes involved in immune regulation and inflammation. Both OS-1 and OS-2 exosomes may enable the re-programming of the tumor micro-environment and establishing a favorable niche for tumor dissemination and metastases.

Figure 6A:
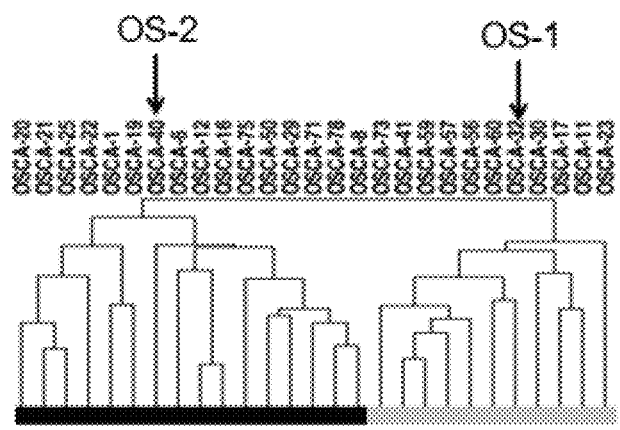
FIGS. 6A and 6B are graphical representations of differences in gene expression and patient survival times between OS-1 and OS-2 phenotypes.
Figure 6B:
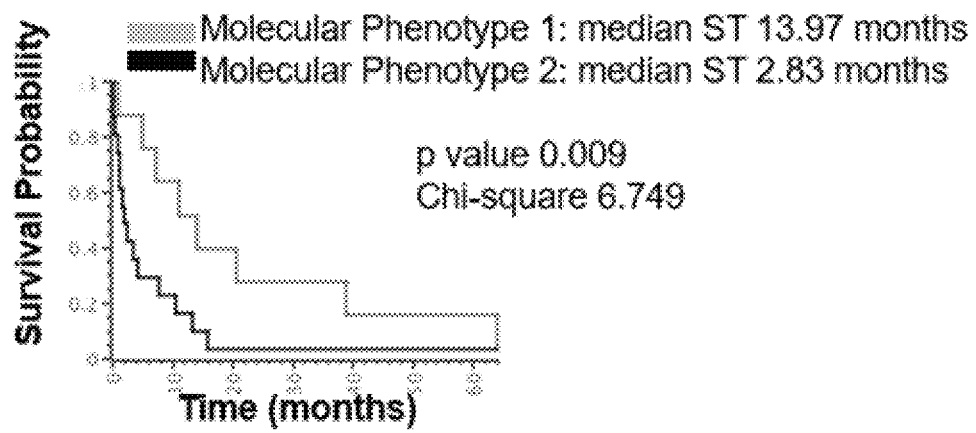

FIGS. 6A and 6B are graphical representations of differences in gene expression and patient survival times between OS-1 and OS-2 phenotypes. FIG. 6A is a sample dendrogram indicating that representative sample canine cell lines OSCA-40 (associated with the OS-2 phenotype) and OSCA-32 (associated with the OS-1 phenotype) were used in the analysis of the example described herein. FIG. 6B is a chart that depicts a Kaplan-Meier analysis of overall survival time (ST) of canine patients according to the sample clustering shown in FIG. 6A. As shown in FIG. 6B, the median survival time of patients with OS-1 is 13.97 months, whereas the median survival time of patients with OS-2 is 2.83 months. The difference in survival times between the OS-1 and OS-2 phenotypes may be at least partially attributable to the greater metastatic potential of OS-2 relative to OS-1. In the example of OS-1 and OS-2, the OSCA-40 cell line may be rapidly metastatic, whereas the OSCA-32 cell line may be poorly or non-metastatic in vivo. Gene expression may vary between different OS cell lines. For example, miR-20a and miR-135b are expressed at higher levels in more aggressive cell lines; this pattern is conserved in human OS. In order to determine or anticipate the biological behavior of OS, OS xenografts can be established in the tibia or tarsus of immunocompromised mice, and the gene expression of the OS xenografts may be analyzed. In addition, such techniques may enable determination of biological interactions between the xenograft tissue (e.g., OS-1 or OS-2 cell lines) and the TME within the host tissue. These experiments may be of relatively short duration and pain associated with tumor growth, and may be managed by using medication and/or amputation as appropriate.

Tumor exosomes package bioactive molecules such mRNAs and microRNAs. Thus, nucleic acids enriched in OS tumors with distinct biological behaviors may be contained in exosomes. Exosomes in canine OS cell lines have been characterized in situ, by flow cytometry, and by biochemical analysis. The data suggest there may be preferential accumulation of mRNA species in cells derived from tumors with different behavior. Thus, at least some the in vivo behavior of OS may be associated with an altered composition of exosomes that enter the circulation and influence distant environments in preparation for tumor dissemination.

For this study, cell lines derived from two spontaneous canine OS with distinctly different biological behavior (OS-1 and OS-2) were used for heterotypic in vivo modeling that recapitulates the heterogeneous biology and behavior of this disease. Both cell lines demonstrated stability of the transcriptome when grown as orthotopic xenografts in athymic nude mice. Consistent with the behavior of the original tumors, OS-2 xenografts grew more rapidly at the primary site and had greater propensity to disseminate to lung and establish microscopic metastasis. Moreover, OS-2 promoted formation of a different tumor-associated stromal environment than OS-1 xenografts. In addition to comprising a larger fraction of the tumors, a robust pro-inflammatory population dominated the stromal cell infiltrates in OS-2 xenografts, while a mesenchymal population with a gene signature reflecting myogenic signaling dominated those in the OS-1 xenografts. The studies described herein show that canine OS cell lines maintain intrinsic features of the tumors from which they were derived and recapitulate the heterogeneous biology and behavior of bone cancer in mouse models. This system provides a resource to understand interactions between tumor cells and the stromal environment that may drive progression and metastatic propensity of OS.

Understanding the heterogeneous biology and behavior of OS may be useful to fully elucidate the pathogenesis of osteosarcoma and other diseases. As described herein, orthotopic canine OS xenografts preserve the biological, molecular, and heterotypic heterogeneity observed in the tumors from which they were derived. Moreover, transcriptome analysis of xenograft tumors revealed a strong OS cell specific stromal response, which may provide evidence that intrinsic genetic tumor characteristics and cross-talk between tumor and stromal cells might underlie heterogeneity of biological behavior in OS patients. These data may provide insight into tumor-host interactions and identify targets that may play a role in treatment strategies for OS patients.

Results

Figure 7A:
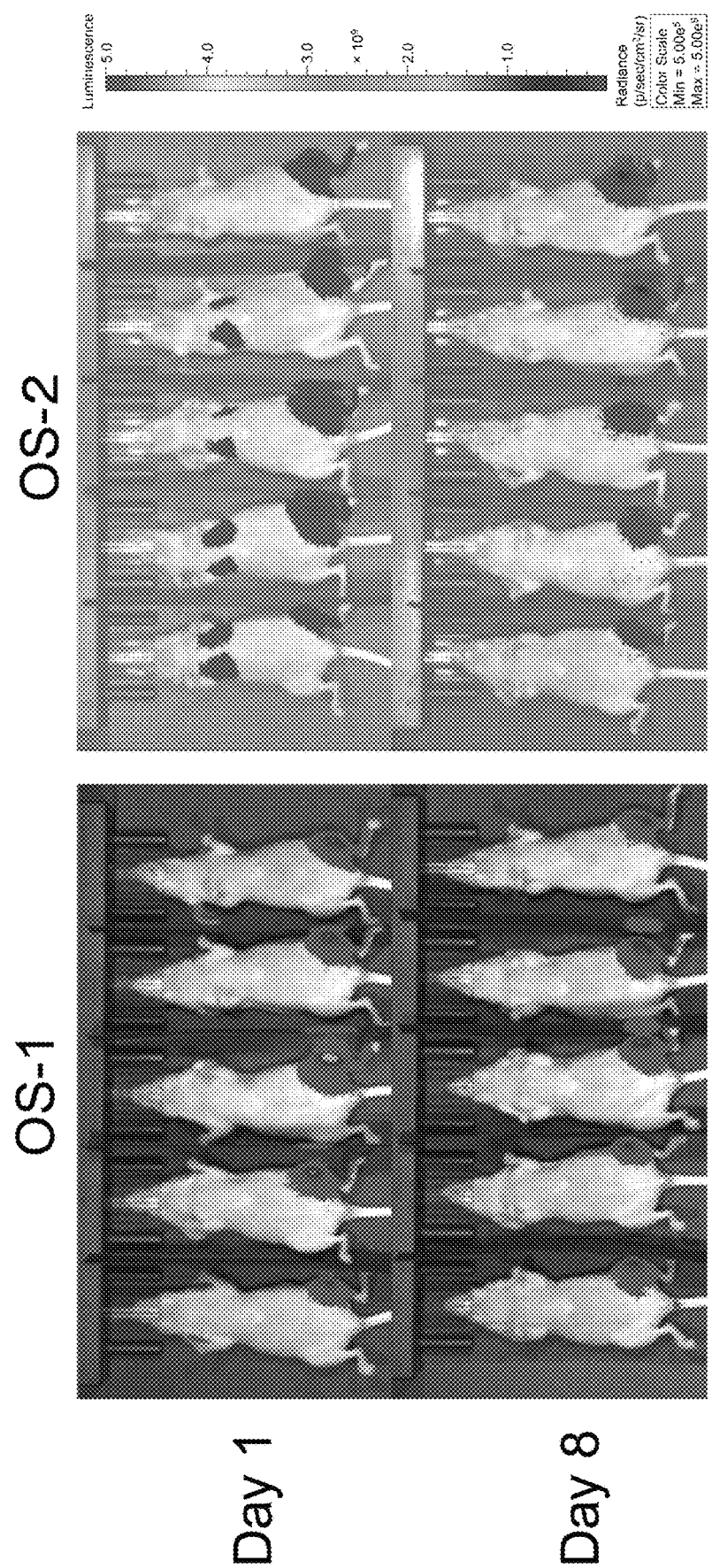
FIGS. 7A and 7B are photographic representations of data pertaining to the application of the techniques described herein to the OS-1/OS-2 xenograft example.
Figure 7B:
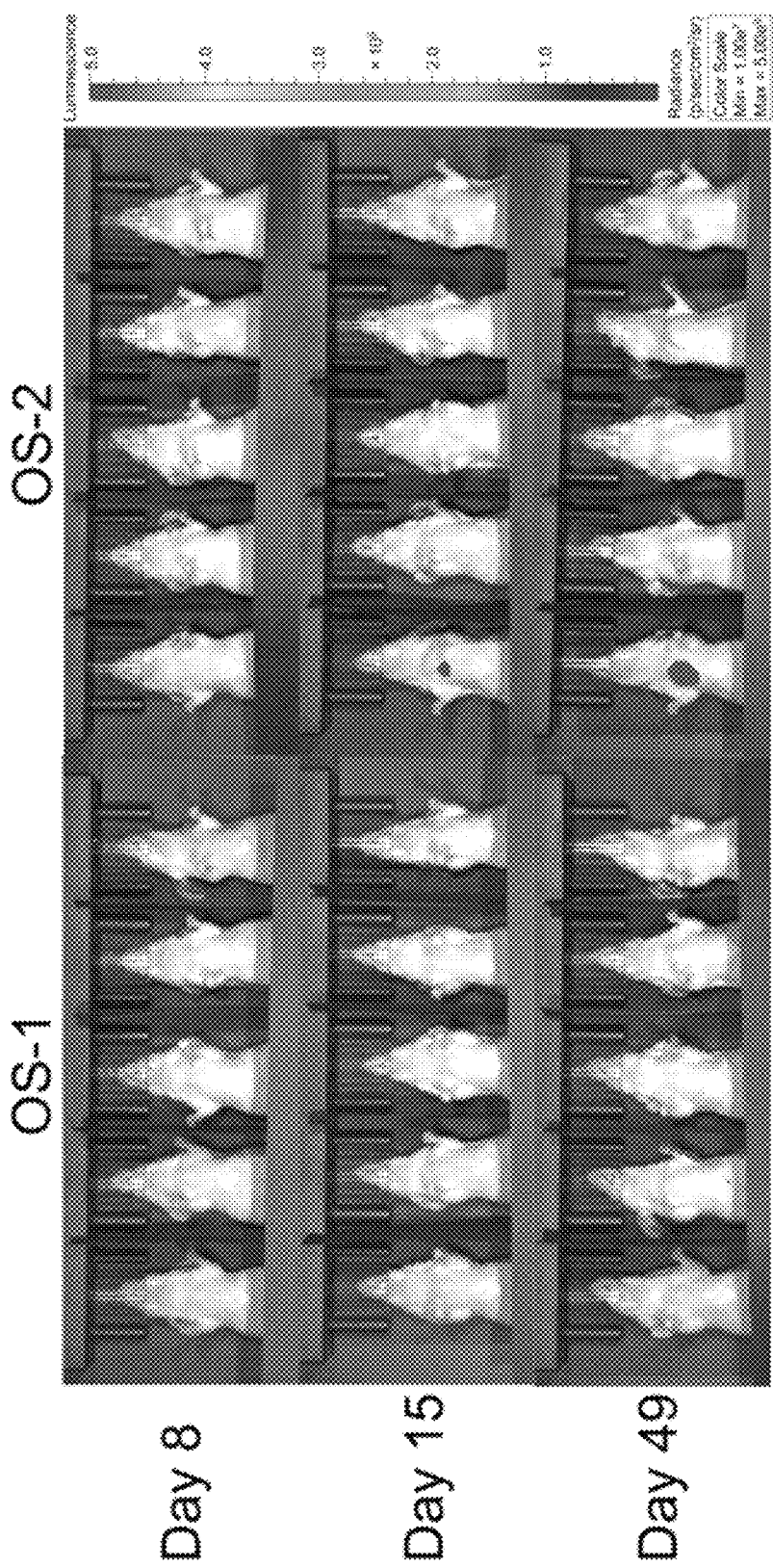

FIGS. 7A and 7B are photographic representations of data pertaining to the application of the techniques described herein to the OS-1/OS-2 xenograft example. FIG. 7A includes photographs of mice injected with OS-1 and OS-2 cells at day 1 post-injection and again at day 8 post-injection. FIG. 7B includes photographs of the mice injected with OS-1 and OS-2 cells at days 8, 15, and 49 post-injection. Luminescence resulting from luciferase activity is shown in radiance ($p/sec/cm^2/sr$). Differential metastatic propensity in orthotopic canine OS-1 and OS-2 xenografts: Luciferase activity was observed in the lungs of mice receiving intratibial OS-2 cells, but not in mice injected with OS-1 cells, within 6 hours of injections (FIG. 7A). This was interpreted as evidence of systemic dissemination of OS-2 cells with accumulation in the lungs. The luciferase signal disappeared from the lungs within one week after tumor administration, but the presence of OS-2 cells was evident focally in the lungs of one mouse from this group again within two weeks after tumor administration, and the luciferase activity in this area continued to increase until the end of the experiment (FIG. 7B). When the mice from all the experiments were considered together, OS-2 cells achieved metastatic dissemination more rapidly than OS-1 cells (by 15, 22, and 29 days), although the rate of microscopic and macroscopic metastasis between the two groups on Day 36 when the experiments were terminated was not different based on imaging ($p=0.35$) or histopathology ($p=0.77$; see also the table illustrated in FIG. 22).

Figure 8B:
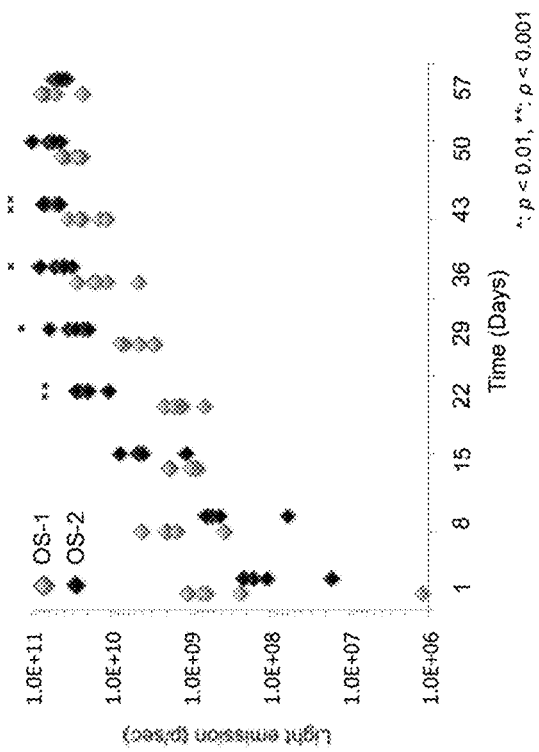
FIGS. 8A-8C are photographic and graphical representations of data pertaining to the application of the techniques described herein to the OS-1/OS-2 xenograft example.
Figure 8A:
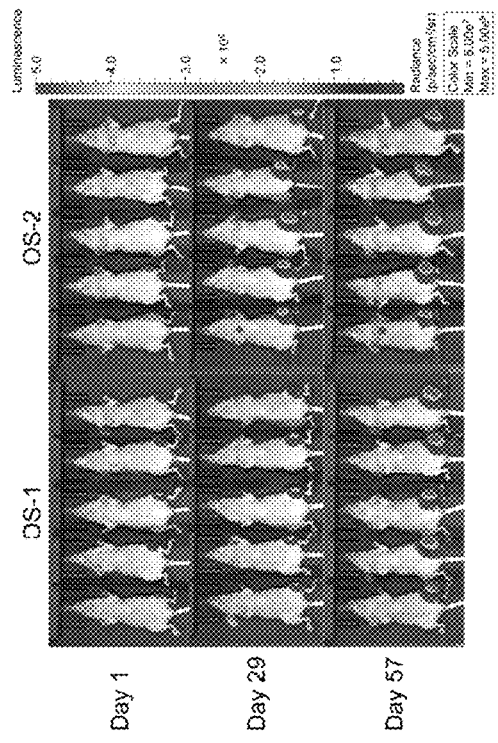
Figure 8C:
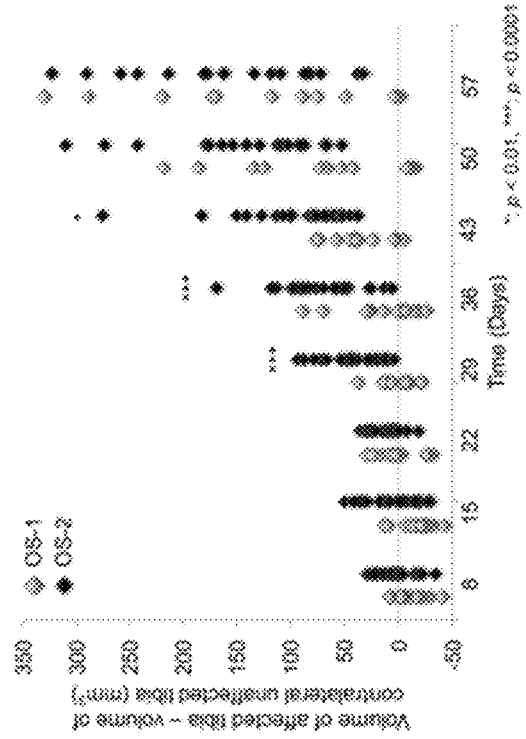

FIGS. 8A-8C are photographic and graphical representations of data pertaining to the application of the techniques described herein to the OS-1/OS-2 xenograft example, and indicate differential growth rates at the primary site in orthotopic canine OS-1 and OS-2 xenografts. FIG. 8A includes photographs of mice injected with OS-1 and OS-2 cells at days 1, 29, and 57 post-injection. Luminescence resulting from luciferase activity is shown in radiance ($p/sec/cm^2/sr$). FIG. 8B illustrates in vivo luciferase activity at different times from 1-59 days post-injection. FIG. 8C illustrates disease progression over time as indicated by tibia volume. Development and progression of primary tumors were examined using in vivo imaging starting six hours after orthotopic cell injections and then weekly for the duration of the study. Luciferase activity was detectable within 6 hours in many of the mice receiving OS-1 or OS-2 cells, and all of the mice showed disease progression over time. Expansion of tumor cells may be inferred from the increased luciferase emission over time. FIG. 8B shows that OS-2 intratibial xenografts had grown significantly faster than OS-1 intratibial xenografts by day 22 and this difference persisted until day 50. The results shown in FIG. 8C encompass a more complex process, as the physical size of the tumors in the proximal tibia would be influenced by infiltrating host stromal cells and swelling. The data confirm that OS-2 intratibial xenografts grew significantly faster than OS-1 intratibial xenografts in this example, although the effect was delayed (detectable by day 29), with this relative difference persisting until day 50 (FIGS. 8B and 8C; see also the table illustrated in FIG. 22). It is worth noting that neither indirect imaging measurements nor direct physical measurements may necessarily account for tumor invasion and loss of periosteal integrity, as is described below. Nevertheless, the data shown in FIGS. 8A-8C and FIG. 23 indicate that, in this example, disease progression was significantly faster in animals harboring OS-2 xenografts than in animals harboring OS-1 xenografts.

FIGS. 9A-9J are graphical representations of data pertaining to the application of the techniques described herein to the OS-1/OS-2 xenograft example. Primary and metastatic tumors derived from orthotopic implantation of OS-1 and OS-2 cells show histological features and organization that are characteristic of canine OS: All of the mice injected with OS-1 or OS-2 cells had evidence of gross tumor burden in the proximal tibia at necropsy on the eighth week after injection (FIGS. 9A and 9B). Histologically, OS-1-derived tumor xenografts were characterized by a relatively well-differentiated, polygonal to spindle-shaped cells that had round to oval nuclei, mild to moderate anisocytosis and anisokaryosis, and infrequent mitotic activity (FIGS. 9C and 9E). These tumors contained organized osteoid ribbons and showed limited destruction of cortical bone and epiphyseal invasion (FIG. 9C).

In contrast, OS-2 tumors had a more aggressive appearance with spindle-shaped, anaplastic cells that had round to elongate nuclei, moderate anisocytosis and anisokaryosis, and frequent mitotic activity (FIGS. 9D and 9F). The cells in these tumors were embedded in a poorly organized, pale eosinophilic matrix and they showed extensive necrosis with marked destruction of cortical bone and epiphyseal invasion (FIG. 9D).

The different metastatic propensity of OS-1 and OS-2 was confirmed histologically (FIGS. 9G-9J; also see the table illustrated in FIG. 22). Fewer than 20% of the mice injected with OS-2 and 7% of the mice injected with OS-1 developed metastasis by Day 36. When lung metastasis was present, the histological appearance of the metastatic tumors recapitulated that of the parent tumors as illustrated by the photomicrographs on one mouse receiving OS-2 orthotopically in FIGS. 9H and 9J. In these animals, the morphology and mitotic activity of the cells and their residence in a poorly organized, pale eosinophilic matrix with extensive areas of necrosis and frequent mitotic activity were comparable to that seen in the primary tumors.

FIGS. 10A-19 illustrate bioinformatics methods that may be used to carry out one or more portions of the methods described herein as applied to the OS-1/OS-2 example. Generally, FIGS. 10A-19 illustrate that a single hybrid reference genome for two species is created by combining the reference sequences of all chromosomes of each species into one file, with chromosome names modified to indicate the species of origin. A single hybrid genome annotation file describing the locations of genes in the genome is created by combining the annotation of each species into one file, with chromosome and gene names modified to indicate the species of origin. A sequence alignment program such as HISAT2 is used to align RNA-Seq sequence reads to the hybrid genome. Most reads may map uniquely to a chromosome of one of the species. Some parts of the genomes may be identical in both species resulting in a small number of multi-mapped reads mapping to two chromosomes, one from each species, although longer sequence reads reduce the number of multi-mapped reads. The presence and abundance levels of genes may be determined by comparing the genomic location of each uniquely aligned read with the genomic locations of genes in the hybrid annotation file and summing the number of reads aligning to each gene. Excluding multi-mapped reads from this abundance estimation step may help avoid incorrectly identifying the presence of graft-derived nucleic acids. Aligning RNA-Seq reads only to the reference genome of the graft species will result in the spurious identification of graft-derived genes in cases where the genes have identical sequences in both species. Comparing gene expressions levels from a xenograft sample with a negative control sample provides further power to reduce false-positives.

Figure 10A:
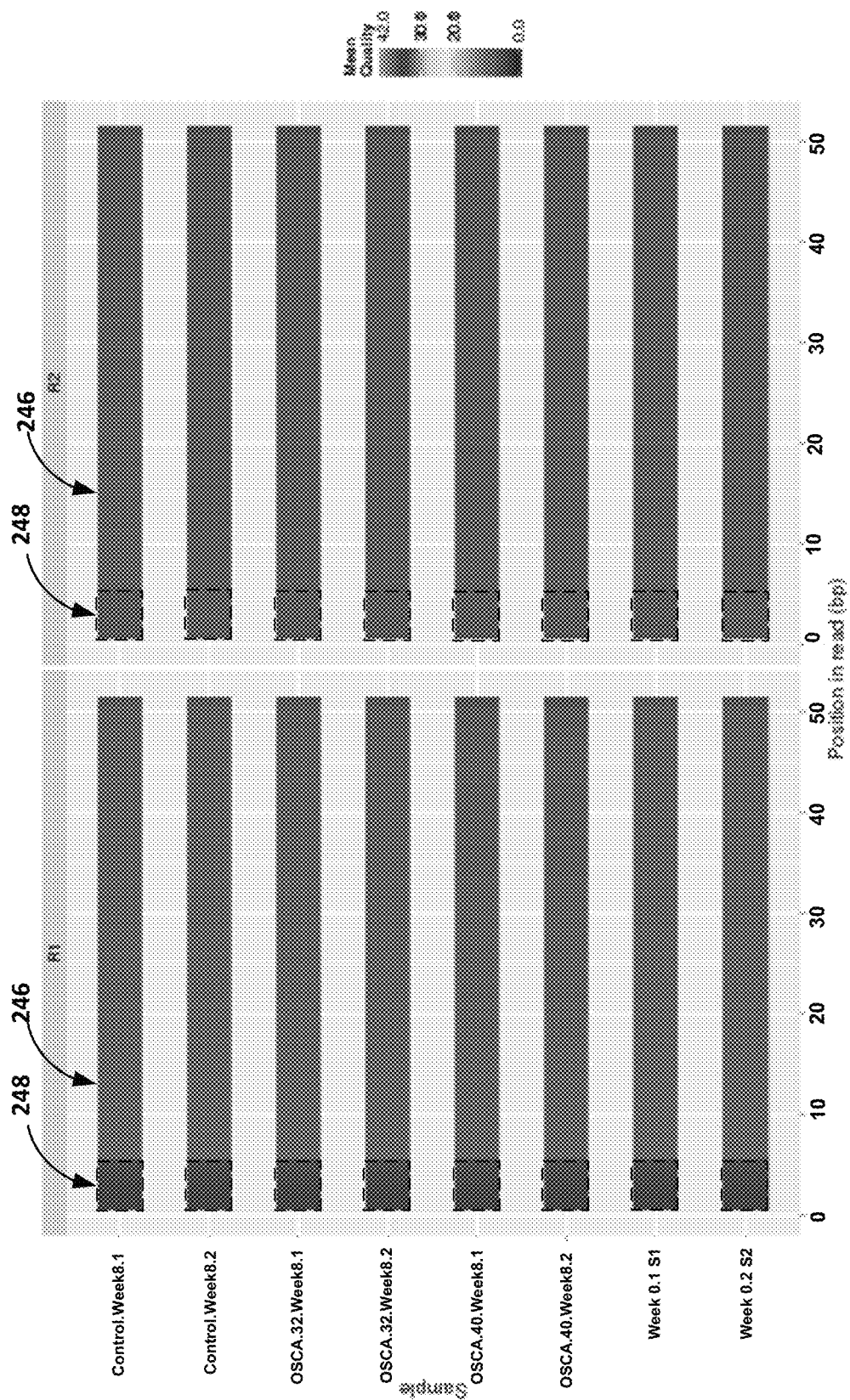
FIGS. 10A and 10B are graphical representations of a data analysis technique in accordance with the examples of this disclosure, as applied to the OS-1/OS-2 xenograft example.

FIG. 10A is a graphical representation of a data analysis technique in accordance with the examples of this disclosure, as applied to the OS-1/OS-2 xenograft example, and illustrates a portion of the bioinformatics workflow analysis in accordance with an example technique of this disclosure. As shown in FIG. 10A, Phred scores may be used for a quality control check to ensure that the raw data fall within acceptable parameters and that there are no problems or biases in the data. In FIG. 10A, a plot of mean quality values (Phred scrore) across all bases at each position in the sequence read is prepared. A Phred score >28 indicate good calling performance. Greyscale shading indicates quality: very good quality calls (246), and calls of reasonable quality (248).

Figure 10B:
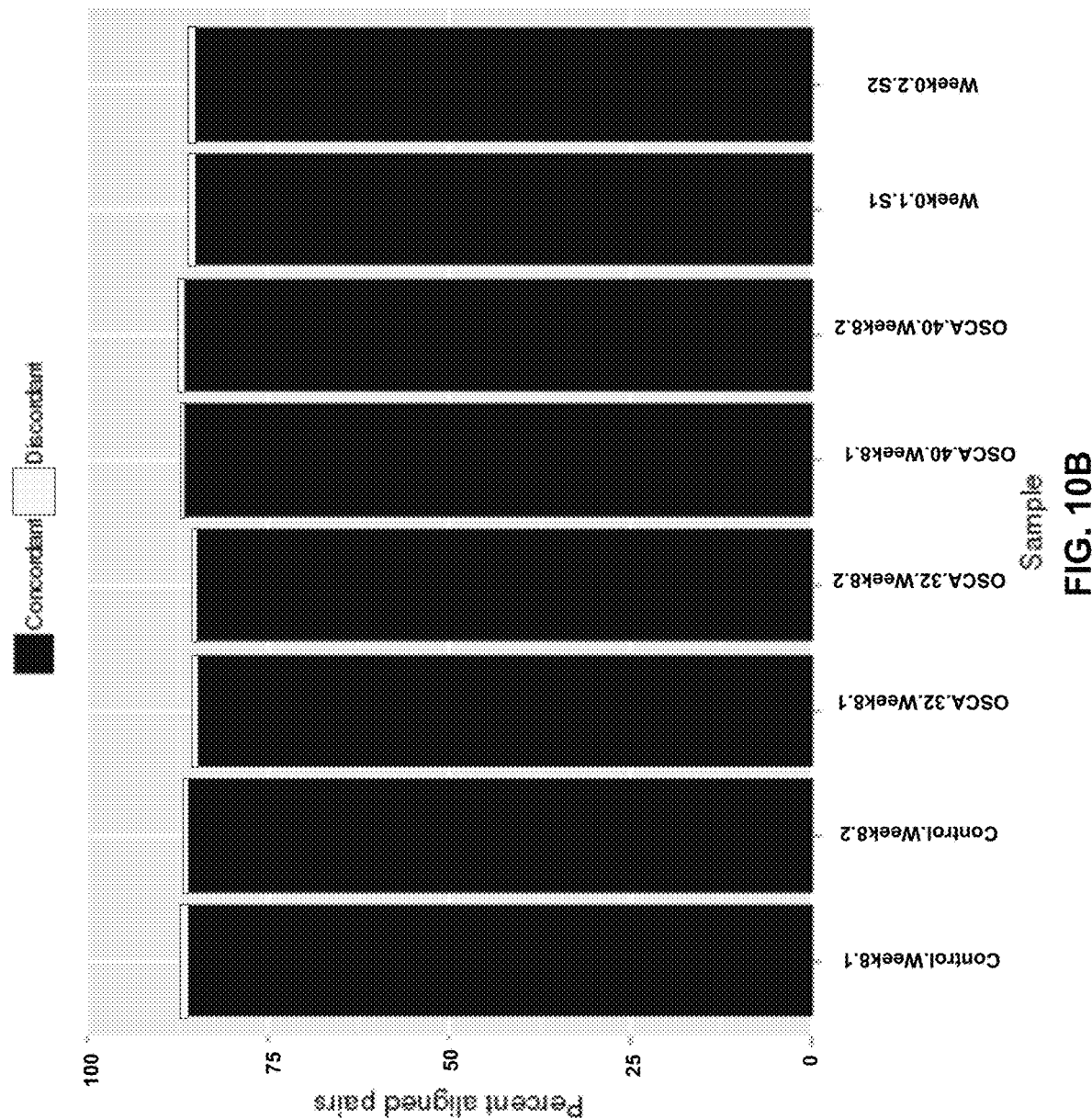

FIG. 10B is a graphical representation of a data analysis technique in accordance with the examples of this disclosure, as applied to the OS-1/OS-2 xenograft example, and further illustrates a portion of the bioinformatics workflow analysis in accordance with an example technique of this disclosure. As shown in FIG. 10B, a percent of sequences aligned to the cross-species hybrid genome, such as by using a HISAT2 aligner to align the RNA sequences to cross-species hybrid genome, is determined.

Figure 11:
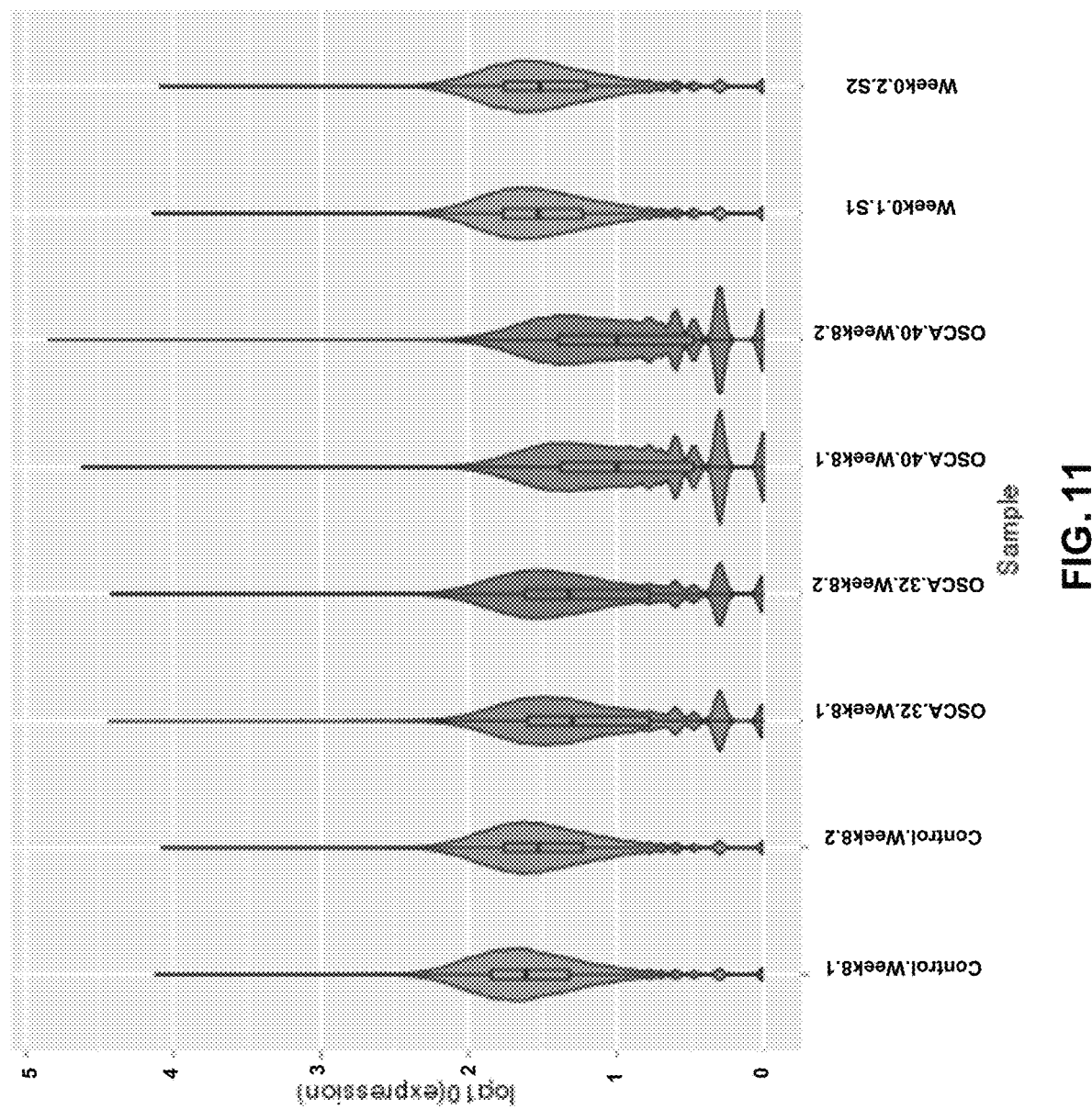
FIG. 11 is a graphical representation of a data analysis technique in accordance with the examples of this disclosure, as applied to the OS-1/OS-2 xenograft example.

FIG. 11 is a graphical representation of a data analysis technique in accordance with the examples of this disclosure, as applied to the OS-1/OS-2 xenograft example, and further illustrates a portion of the bioinformatics workflow analysis in accordance with an example technique of this disclosure. As shown in FIG. 11, gene abundance values may be generated and graphically rendered. The presence and abundance levels of genes are determined by comparing the genomic location of each uniquely aligned read with the genomic locations of genes in the hybrid annotation file and summing the number of reads aligning to each gene. For this analysis raw counts may be generated by a feature counts summarization program as the abundance value. Such a program does not count reads overlapping with more than one genomic region. FIG. 11 illustrates the violin plots that show the distributions of gene abundance values, although other types of plots also may be used to illustrate gene abundance values.

Figure 12:
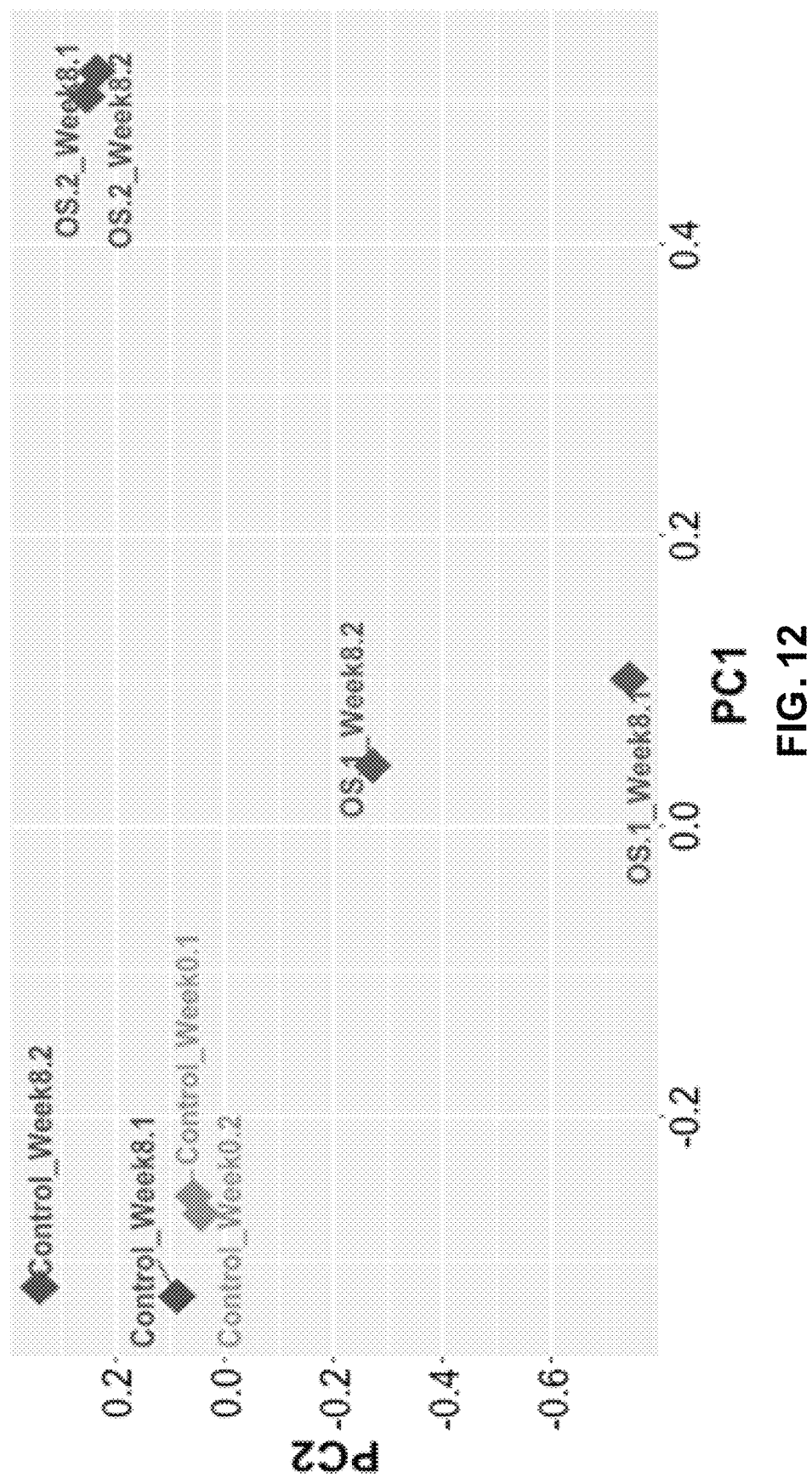
FIG. 12 is a graphical representation of a data analysis technique in accordance with the examples of this disclosure, as applied to the OS-1/OS-2 xenograft example.

FIG. 12 is a graphical representation of a data analysis technique in accordance with the examples of this disclosure, as applied to the OS-1/OS-2 xenograft example, and further illustrates a portion of the bioinformatics workflow analysis in accordance with an example technique of this disclosure. Specifically, FIG. 12 is plot from multidimensional scaling of gene abundance values is examined to explore relationships between samples and to identify and potential outliers, and illustrates multi-dimensional scaled plot for samples in this experiment based on gene abundance values illustrated in FIG. 11. Note scale has been shrunken to appreciate separation. Samples from controls and mice without tumors form a tight cluster, with some separation along the first dimension for tumor samples, and separation along the second dimension between the tumor samples.

Figure 13:
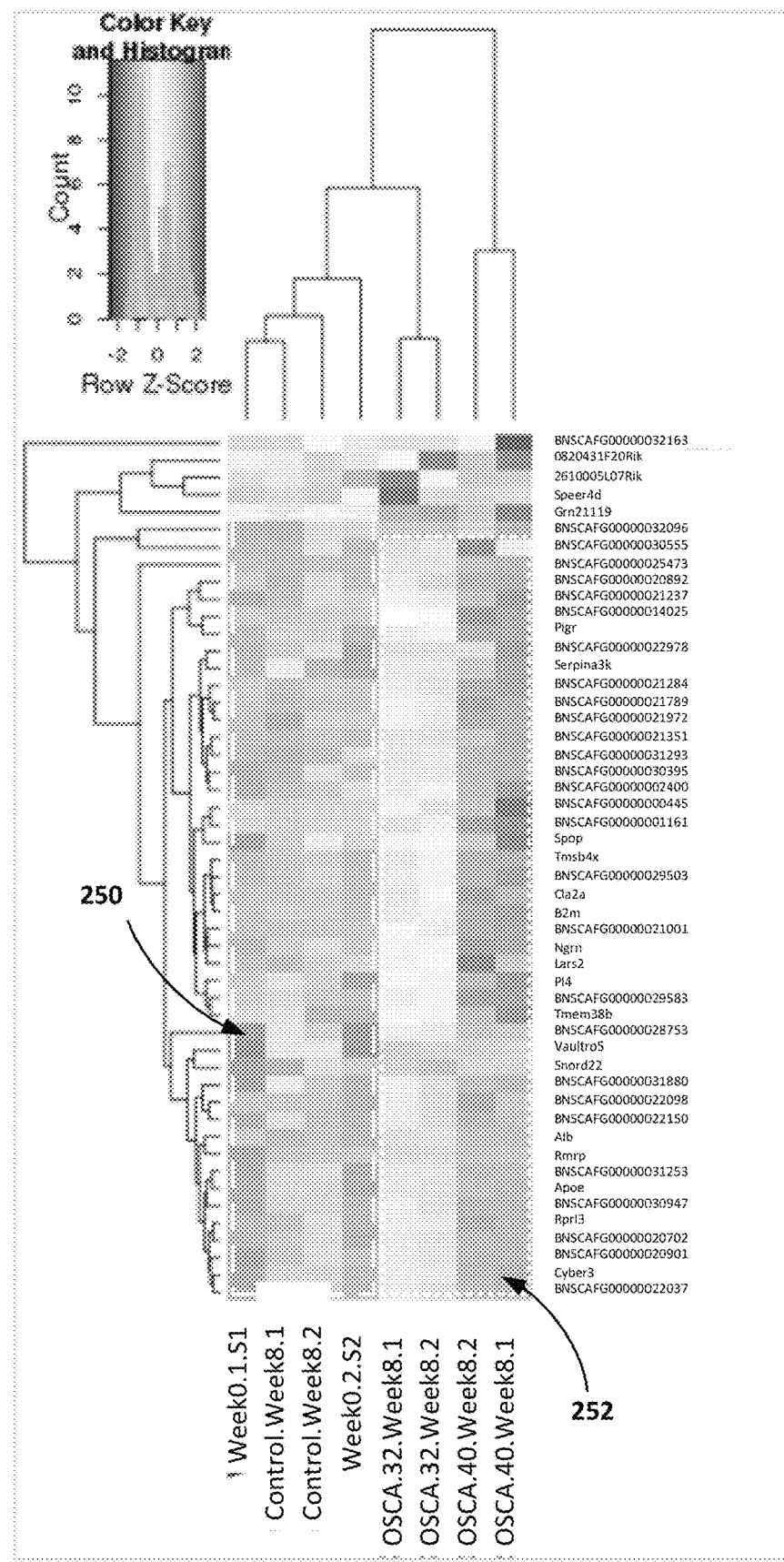
FIG. 13 is a graphical representation of a data analysis technique in accordance with the examples of this disclosure, as applied to the OS-1/OS-2 xenograft example.

FIG. 13 is a graphical representation of a data analysis technique in accordance with the examples of this disclosure, as applied to the OS-1/OS-2 xenograft example, and further illustrates a portion of the bioinformatics workflow analysis in accordance with an example technique of this disclosure. Specifically, FIG. 13 is a hierarchical clustering heat map illustrating that samples that are most similar occupy closer positions in tree, while samples that are less similar are separated by larger numbers of branch points. Hierarchical clustering heatmaps, such as the heatmap of FIG. 13, may be generated after converting gene abundance values to z-scores. A color or greyscale scheme may be applied for the visualization of "high" and "low" gene abundance values in the samples, as shown in FIG. 13. For the sake of illustration, an area indicating low z-scores is depicted at 250, and an area of high z-scores at 252. The rows of the heatmap identify the names of the genes represented in the heatmap. In the heatmap of FIG. 13, the dog genes are identifiable by having an Ensembl gene name (e.g., ENSCAFG . . . ID), while the mouse genes are identifiable by murine gene symbol. OSCA-40 replicate samples cluster together away from OSCA-32 and the control samples indicating that they are more similar to one another than to other samples.

Figure 14:
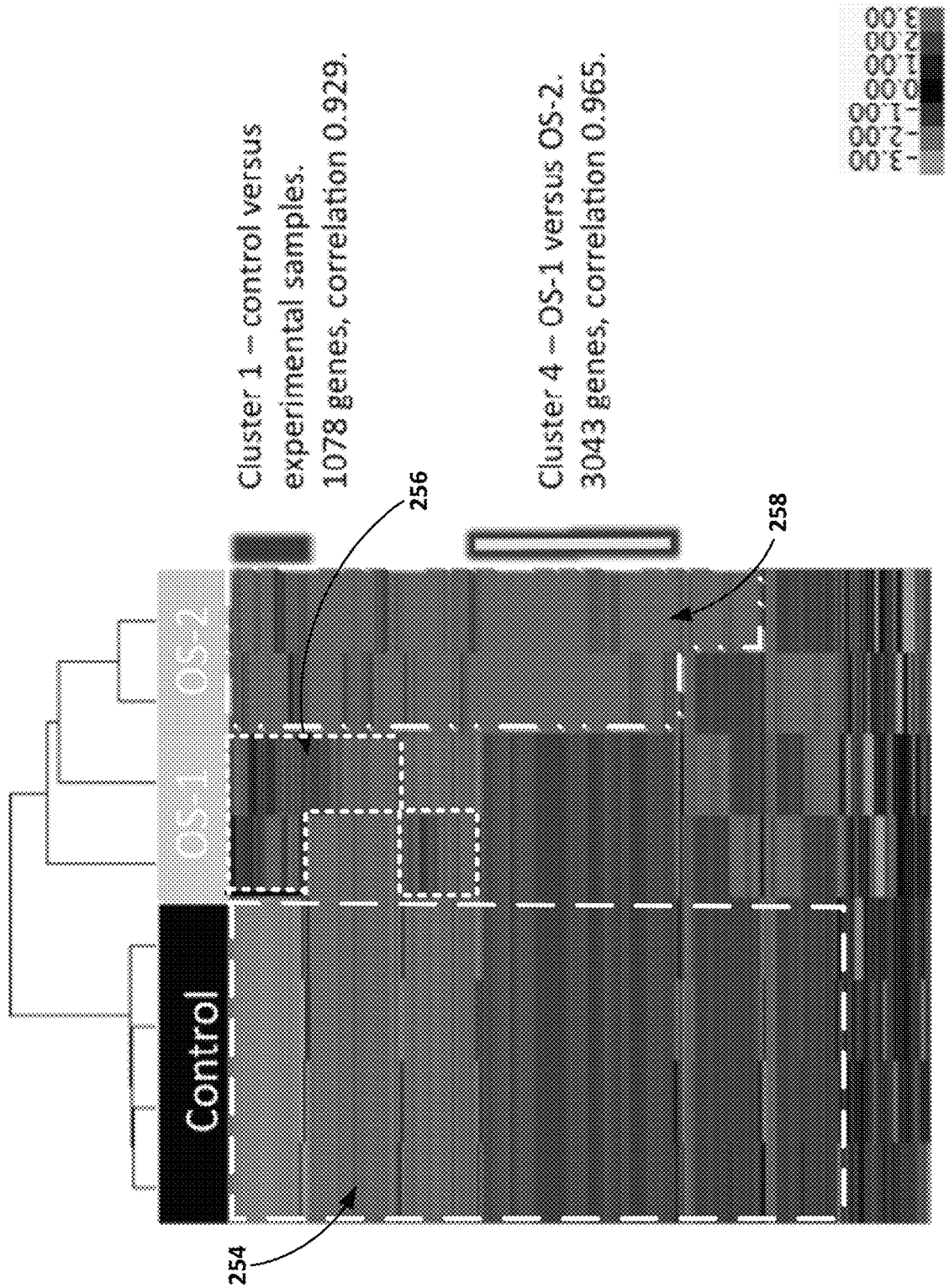
FIG. 14 is a graphical representation of a data analysis technique in accordance with the examples of this disclosure, as applied to the OS-1/OS-2 xenograft example.

FIG. 14 is a graphical representation of a data analysis technique in accordance with the examples of this disclosure, as applied to the OS-1/OS-2 xenograft example, and further illustrates a portion of the bioinformatics workflow analysis in accordance with an example technique of this disclosure. As illustrated in FIG. 14, identification of canine and murine may performed to identify genes that are differentially abundant in: controls versus xenograft samples (canine specific sequences), and OS-1 versus OS-2 xenograft samples. FIG. 14 illustrates a hierarchical clustering heatmap of log transformed and mean centered gene abundance values. The heatmap represents clustered gene-level counts with lower than mean (values of −3.00-−1.00; area 254), higher than the mean (values of 1.00-3.00; areas 256 and 258), and mean (value of 0.00) levels of expression. Each row of the heat map represents a single gene. As shown in FIG. 14, there are a number of highly correlated genes that are abundant in xenograft samples, OS-1 (OSCA-32) and OS-2 (OSCA-40) compared to control samples (denoted as Cluster 1). These 1078 genes all had canine genes IDs. There are a number of highly correlated genes that are more abundant in OS-2 xenografts compared to OS-1 xenograft samples (denoted as Cluster 4). In the example illustrated in FIG. 14, such genes all had canine gene IDs.

Figure 15:
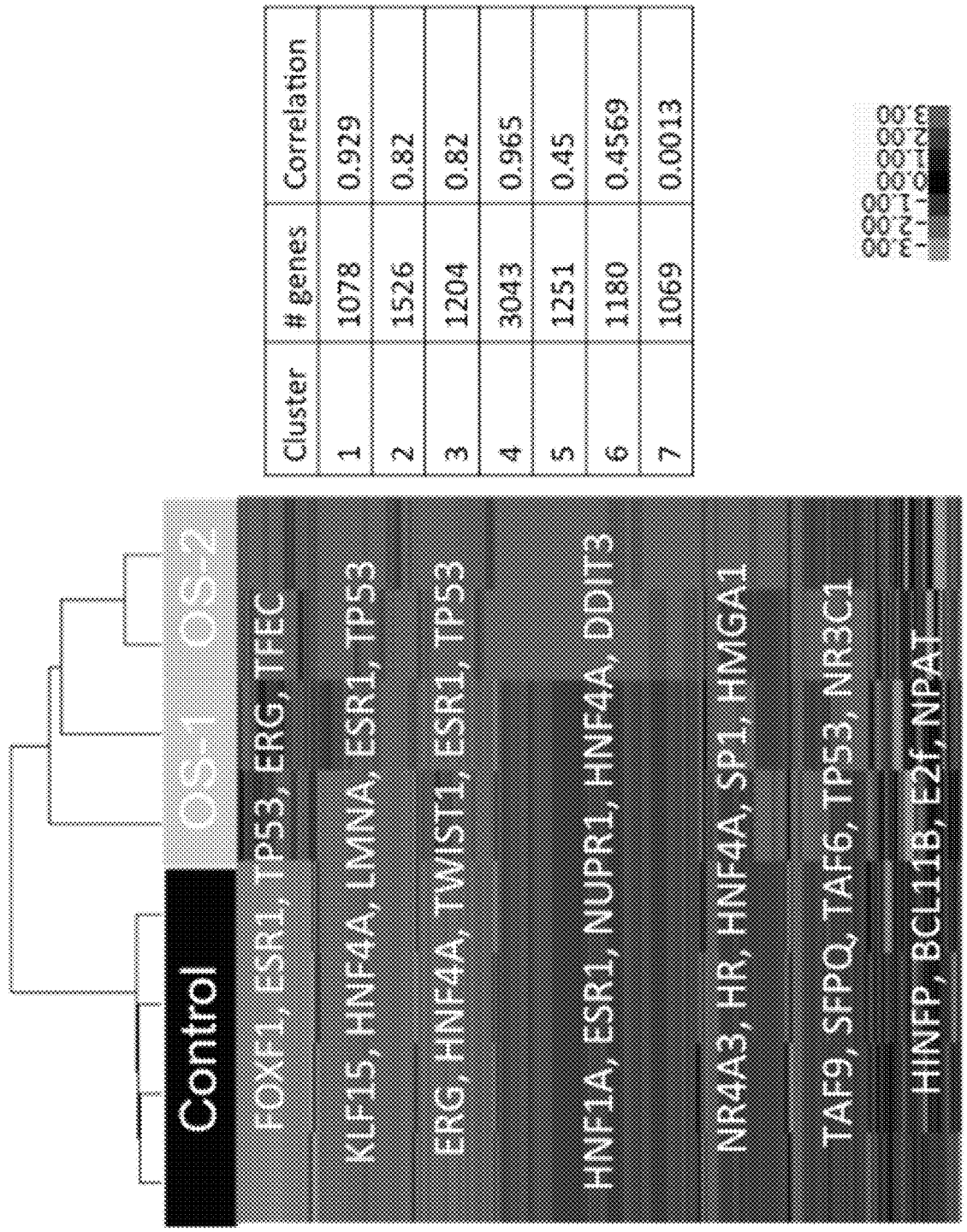
FIG. 15 is a graphical representation of a data analysis technique in accordance with the examples of this disclosure, as applied to the OS-1/OS-2 xenograft example, indicating predicted upstream regulators identified from the data analysis technique of FIG. 14.

FIG. 15 is a graphical representation of a data analysis technique in accordance with the examples of this disclosure, as applied to the OS-1/OS-2 xenograft example, and further illustrates a portion of the bioinformatics workflow analysis in accordance with an example technique of this disclosure, including the determination of biological processes and canonical pathways associated with gene clusters identified from the hierarchical clustering heatmap of FIG. 14. FIG. 15 depicts the heatmap of in FIG. 14 overlaid with the outcome of a technique that includes predicting upstream regulators for the seven gene clusters that were identified from hierarchical clustering heatmap by the data analysis technique of FIG. 14. FIG. 15 illustrates that Cluster 7 consists of exclusively mouse genes.

Figure 16:
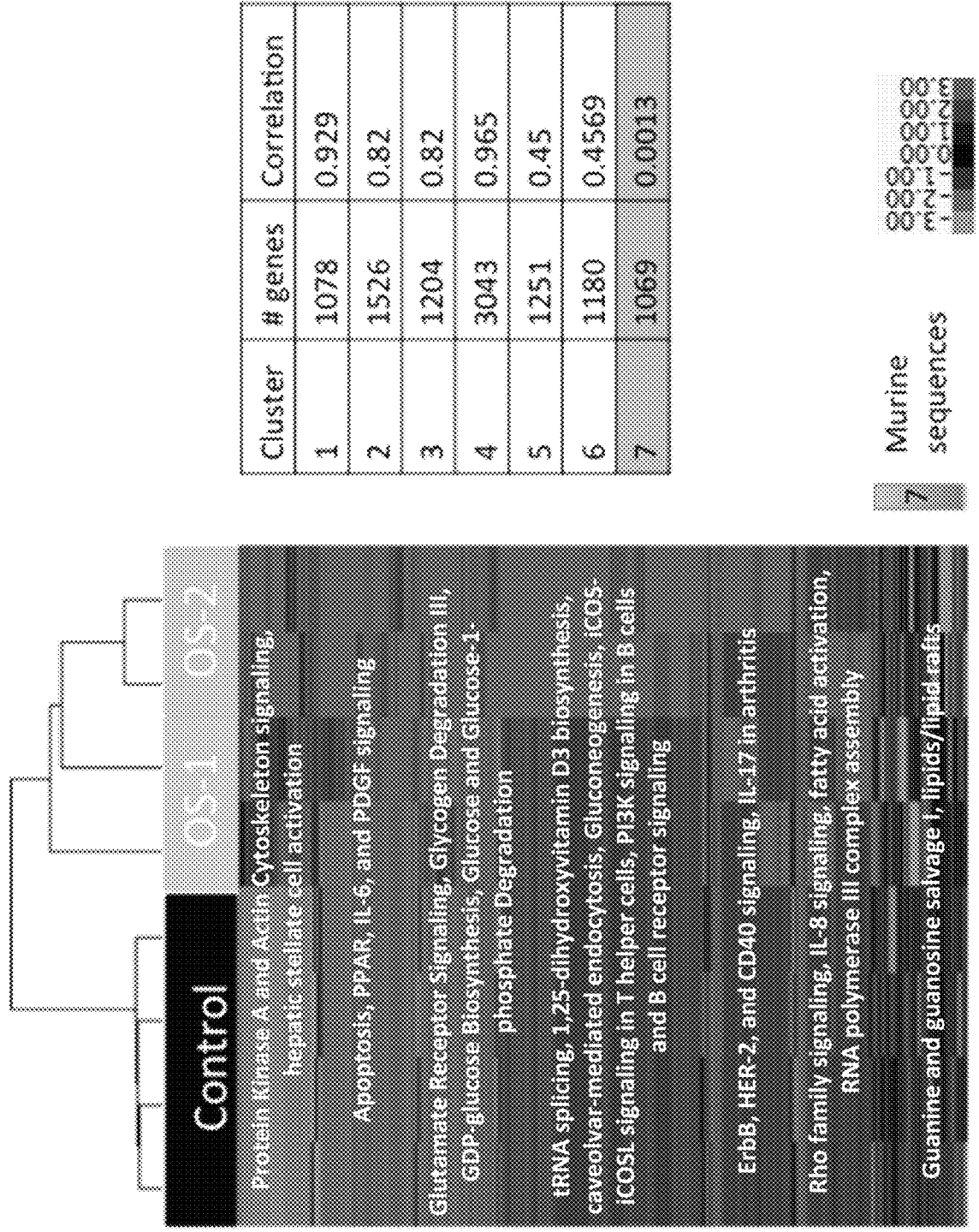
FIG. 16 is a graphical representation of a data analysis technique in accordance with the examples of this disclosure, as applied to the OS-1/OS-2 xenograft example, indicating biological processes and canonical pathways associated with gene clusters identified from the data analysis technique of FIG. 14.

FIG. 16 is a graphical representation of a data analysis technique in accordance with the examples of this disclosure, as applied to the OS-1/OS-2 xenograft example, and further illustrates a portion of the bioinformatics workflow analysis in accordance with an example technique of this disclosure. As illustrated in FIG. 16, biological processes and canonical pathways associated with gene clusters identified from the hierarchical clustering heatmap of FIGS. 14 and 15 may be determined. The heat map pictured in FIG. 16 is the same as shown in FIGS. 14 and 15. Top predicted transcriptional regulators of genes for each gene cluster defined by hierarchical clustering are shown in the heatmap. FIG. 16 illustrates that Cluster 7 consists of exclusively mouse genes. ErbB-1 also is named epidermal growth factor receptor (EGFR), and ErbB-2 is also named HER2 in humans and neu in rodents.

Figure 17:
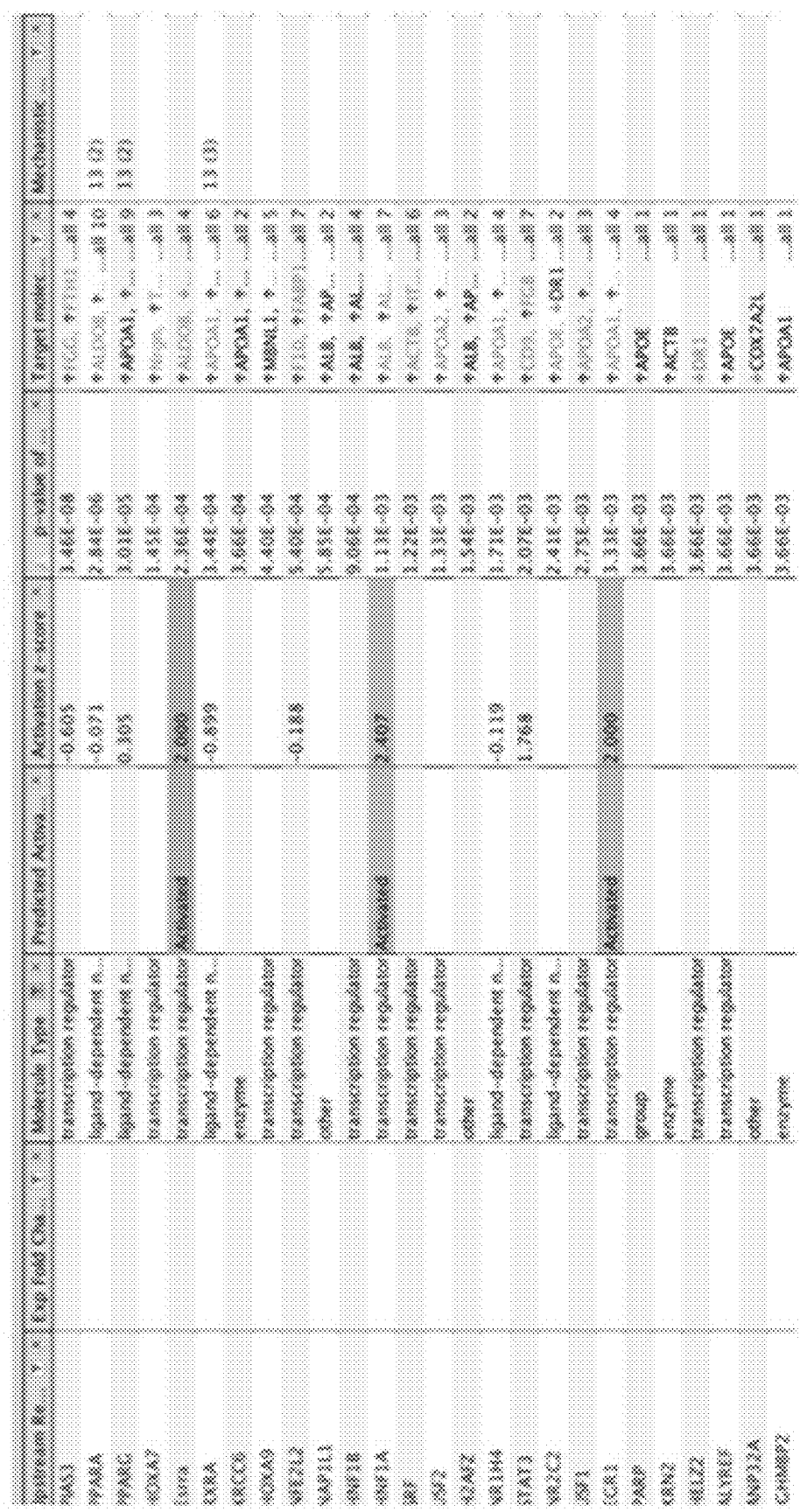
FIG. 17 is a graphical representation of a data analysis technique in accordance with the examples of this disclosure, as applied to the OS-1/OS-2 xenograft example.

FIG. 17 is a graphical representation of a data analysis technique in accordance with the examples of this disclosure, as applied to the OS-1/OS-2 xenograft example, and further illustrates a portion of the bioinformatics workflow analysis in accordance with an example technique of this disclosure. FIG. 17 illustrates a determination of canine and murine genes that have statistically different abundances and identification of predicted upstream regulators of these genes with respect to (1) controls versus xenograft samples, and (2) OS-1 xenograft samples versus OS-2 xenograft samples. As illustrated in FIG. 17, predicted upstream regulators for 125 statistically different mouse (host) genes between controls and xenograft samples were identified using the data analysis technique of FIG. 17.

Figure 18:
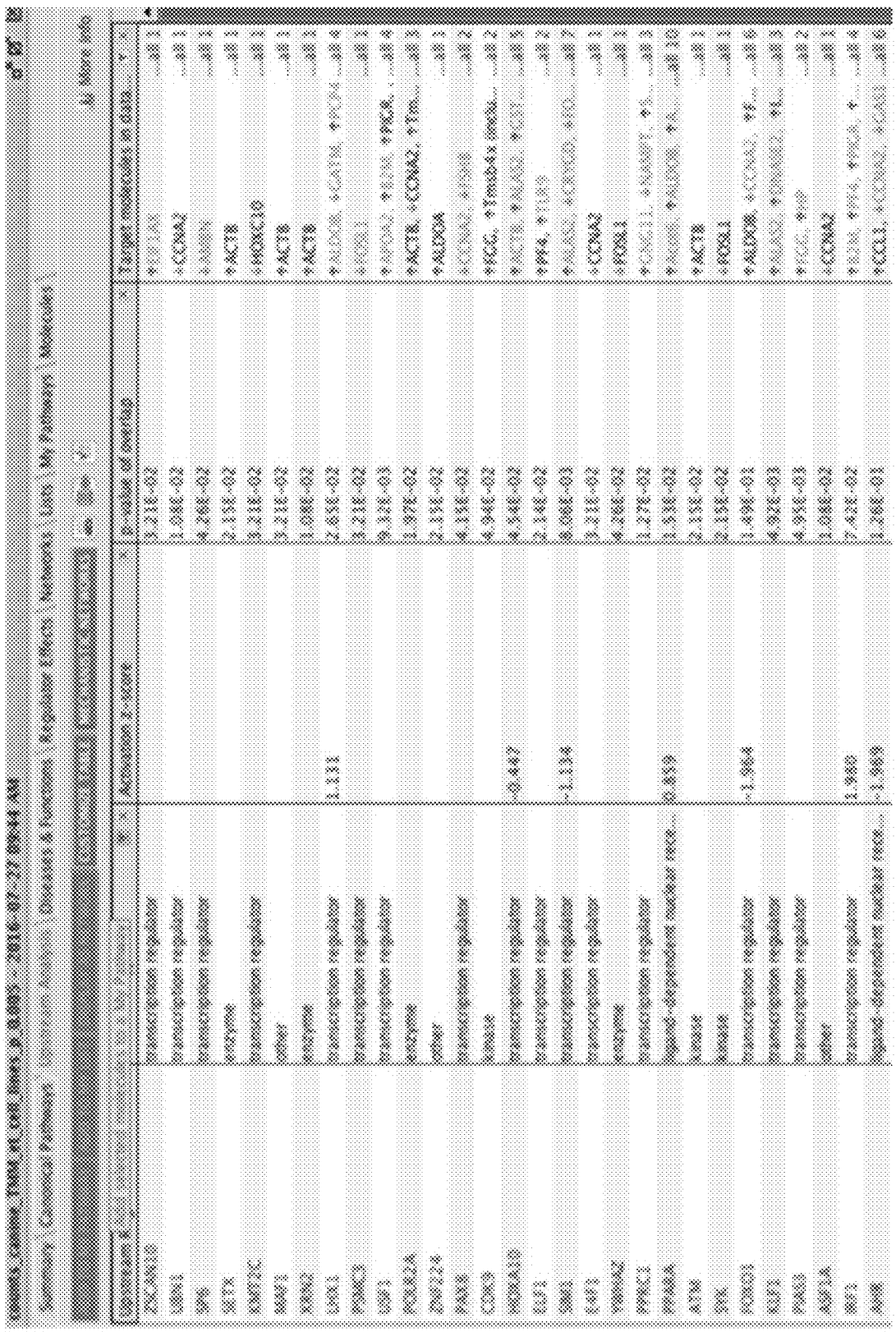
FIG. 18 is a graphical representation of a data analysis technique in accordance with the examples of this disclosure, as applied to the OS-1/OS-2 xenograft example.

FIG. 18 is a graphical representation of a data analysis technique in accordance with the examples of this disclosure, as applied to the 0S-1/OS-2 xenograft example, and further illustrates a portion of the bioinformatics workflow analysis in accordance with an example technique of this disclosure. At FIG. 18, predicted upstream regulators for 325 statistically (p<0.005) different mouse (host) genes between OS-1 and OS-2 xenograft samples are determined. Predicted activity is in OS-2 with respect to OS-1 xenograft samples.

Figure 19:
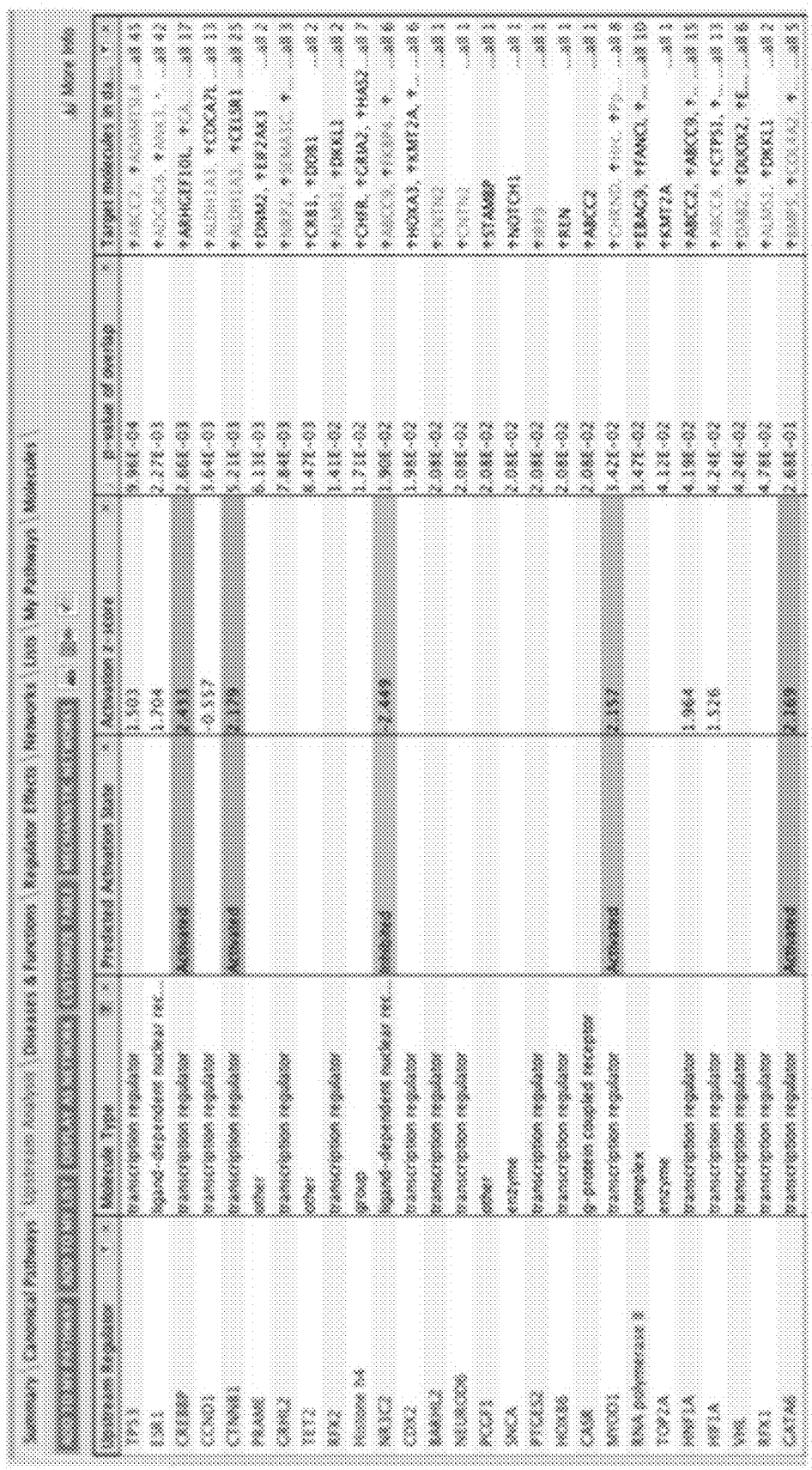
FIG. 19 is a graphical representation of a data analysis technique in accordance with the examples of this disclosure, as applied to the OS-1/OS-2 xenograft example.

FIG. 19 is a graphical representation of a data analysis technique in accordance with the examples of this disclosure, as applied to the OS-1/OS-2 xenograft example, and further illustrates a portion of the bioinformatics workflow analysis in accordance with an example technique of this disclosure. FIG. 19 illustrates predicted upstream regulators of 530 statistically (p<0.05) different canine genes between OS-1 and OS-2 xenograft samples. Predicted activity is in OS-2 with respect to OS-1 xenograft samples. In some examples, canine genes may validate previously reported data indicating differences between tumors arising from OS-1 and OS-2, although canine genes isolated from blood may be different from genes obtained from tissue (e.g., from tumor tissue).

Figure 20A:
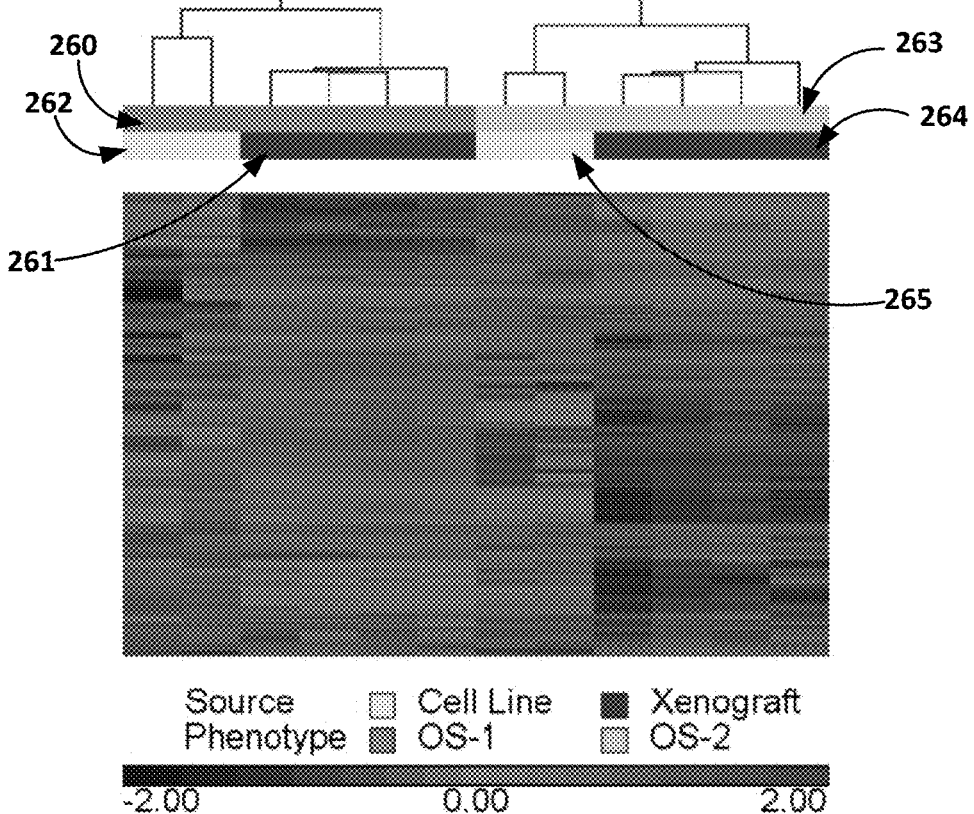
FIGS. 20A and 20B are graphical representations of a data gathering and analysis technique in accordance with the examples of this disclosure, as applied to the OS-1/OS-2 xenograft example
Figure 20B:
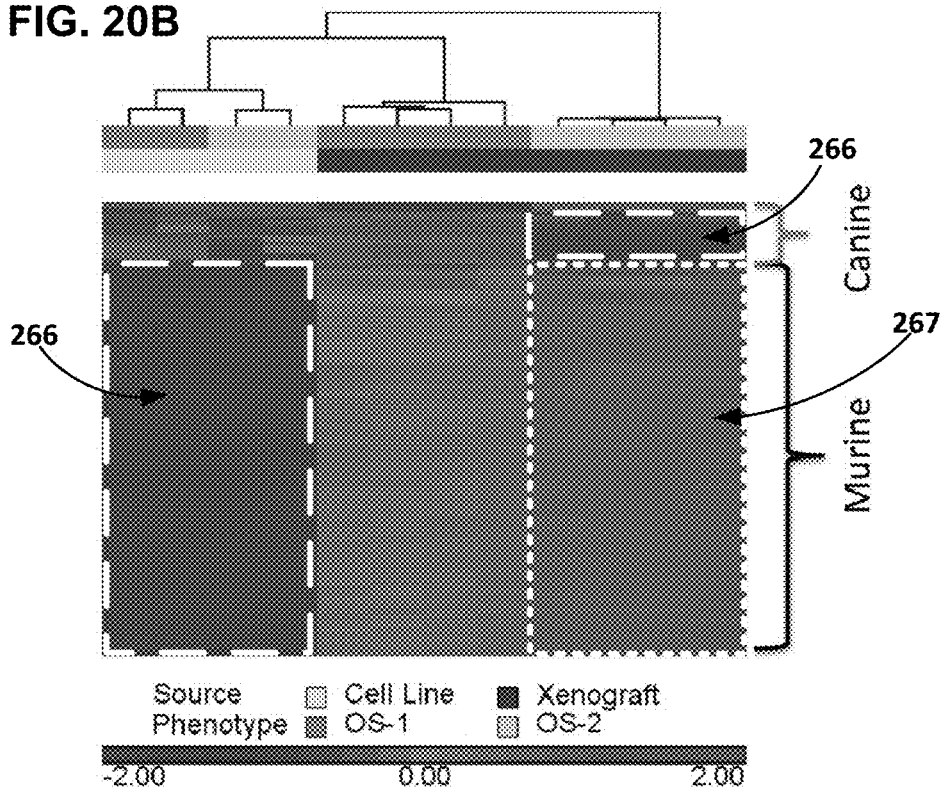

FIGS. 20A and 20B are graphical representations of a data gathering and analysis technique in accordance with the examples of this disclosure. FIG. 20A illustrates that gene signatures of tumor cells in OS xenografts resemble those of parent cell lines. FIG. 20B illustrates hierarchical clustering of tumor xenografts and parent cell lines with canine and murine genes. One obstacle to using xenograft models to understand the heterogeneity of genetically complex tumors is the presumption that these tumors are unstable and will drift rapidly as they adapt to the host microenvironment. Indeed, previous data suggest that altered genomic signatures due to tumor cell plasticity and/or harsh clonal selection lead to unpredictable behavior of tumor cell lines after being transplanted into mice. Here, RNA sequencing was used to examine the stability of key transcriptomic properties between the parental OS cell lines and their corresponding tumor xenografts. The tumor xenografts were more similar to their corresponding parent cell lines than to each other or to the alternative cell line based on principal components analysis and by unsupervised clustering (FIG. 20A), where tumor xenografts were assigned to the same group as their corresponding parent cell line based on the expression signatures from canine genes.

As shown in FIG. 20A, gene signatures of parent tumor cell lines maintained in OS-1 and OS-2 xenograft tumors. 24,579 total canine genes were filtered to remove genes that did not have a log 2 counts per million (CPM) mean-centered value ≤1 in at least two samples. 13,141 genes remained after filtering. The heatmap represents clustered gene-level counts with lower than mean (values of −2.00-~−0.10; e.g., areas 266 in FIG. 20B), higher than the mean (~0.10-2.00; e.g., area 267 in FIG. 20B), and mean (0.00) levels of expression. Each row represents a single gene. The dendrogram represents the distance or dissimilarity between sample clusters, calculated using unsupervised hierarchical clustering on CPM values for the 13,141 filtered genes. In this dendrogram, there are two sample clusters as two branches that occur at about the same vertical distance. One of the sample clusters consists of four OS-1 (260) xenograft tumors (261) and two parental cell line replicates (262), and one of these clusters consists of four OS-2 (263) xenograft tumors (264) and two parental cell line replicates (265). All replicates are biological replicates.

When dog and mouse genes were analyzed together, expression of mouse-specific genes was not detected in the canine cell lines (FIG. 20B), indicating that the mouse genes present in the tumor xenograft tissues could be accurately differentiated from the dog genes using the comparative bioinformatics approach. Furthermore, significantly larger numbers of mouse genes were detectable in OS-2 than in OS-1 xenografts, suggesting the former tumors were more heavily infiltrated by host stroma (FIG. 20B).

FIG. 20B illustrates log-transformed and mean-centered counts per million (CPM) values for 47,997 canine and murine genes in xenograft and parental cell line samples that were filtered to remove genes that did not have a log 2 CPM mean-centered value ≥3 in at least two samples. This filtering step excluded most of the canine genes while including the murine genes. Unsupervised hierarchical clustering with counts per million values for the remaining 13,968 canine and murine genes indicated that expression levels of murine genes in canine cell lines was absent in comparison to the tumor xenografts, illustrating that murine genes can be properly differentiated from the canine genes in xenografts.

FIGS. 21A-21C are graphical representations of data gathering and analysis techniques in accordance with the examples of this disclosure, and illustrate that OS-1 and OS-2 xenografts may promote distinct tumor-associated stromal environments. To determine the nature of the stromal interactions and the identity of the infiltrating cells in the xenografts, pair-wise Exact Test comparisons were performed, with TMM normalization of gene counts, to identify the differentially expressed murine genes in tumors from each group (OS-1 and OS-2). Four biological replicates were used for each OS subtype. Common dispersion across all genes was calculated as 0.079 and the biological coefficient of variation (BCV) as 0.23. Mean tag-wise dispersion (individual dispersion for each gene) was calculated as 0.095. Using a false discovery rate (FDR)-adjusted p-value of <0.005 and $\log_2$ fold change >2,482 genes were identified that were expressed at significantly different levels between the two groups (FIG. 21A; Table S2). After identifying differentially expressed genes (DEG), log transformed and mean-centered counts per million (CPM) values for 47,997 canine and murine genes were generated. The Pearson distance similarity metric and average linkage clustering method was used for hierarchical clustering of $\log_2$ CPM values for the 482 differentially expressed murine genes (see table S2 below for detailed gene lists).

The heatmap in FIG. 21A shows clustered gene-level counts with lower than mean (negative values; e.g., area 270), higher than the mean (positive values; e.g., area 272), and mean (value=zero) levels of expression. Each row represents a single gene. The dendrogram of the horizontal axis of the heat map shows two sample clusters; OS-1 and OS-2 xenografts are in separate sample groups (FIG. 21A). The rows of the heat map (vertical axis) cluster into two highly correlated groups. Rows corresponding to a positive value in the vertical dendrogram are murine genes that are upregulated in OS-2 xenografts (e.g., a majority of the rows in region 270), whereas rows corresponding to a negative value are downregulated relative to OS-1 xenografts (e.g., a majority of the rows in region 272). Enriched pathway and functional classification analyses of DEGs were performed using QIAGEN's Ingenuity® Pathway Analysis (IPA®, QIAGEN Redwood City, www.qiagen.com/ingenuity) according to row cluster designation. Upregulated genes are identified in FIG. 21B, and downregulated genes are identified in FIG. 21C.

To better understand the differences between OS-1 and OS-2, the upregulated and downregulated murine genes in OS-2 were considered as separate lists and used IPA to identify enriched biological functions and transcription factors that regulate these genes. The 482 differentially expressed murine genes included 240 that were upregulated, and 242 that were downregulated in OS-2 tumor xenografts relative to OS-1 tumor xenografts. The most upregulated murine gene in the OS-2 xenografts was Mcpt 1 (+11.25 fold), whereas the most downregulated murine gene was Nkx2-1 (−10.97 fold) (see table S2).

Based on biological function and processes, the most upregulated murine genes in OS-2 tumors were proteases, metallopeptidases, cytokines, and chemokines involved in cell movement, leukocyte migration, inflammation, and angiogenesis (FIG. 21C, Table S2). On the other hand, the most downregulated genes in OS-2 tumor xenografts were transcriptional regulators of cellular differentiation and cell cycle involved in formation and morphology of muscle (FIG. 21C, Table S2).

FIGS. 22-27 are tables providing additional information pertaining to the application of the techniques described herein to the OSC1/OSC2 xenograft example. For example, the tables illustrated in FIGS. 22-27 provide information pertaining to the metastatic rates, rates of tumor progression, and pathways for differentially expressed murine genes and their upstream regulators for this particular example.

FIG. 22 is a table that illustrates the metastatic properties of the OS-1 xenografts as compared to the OS-2 xenografts at 15-57 days post-injection. When the mice from all the experiments were considered together, OS-2 cells achieved metastatic dissemination more rapidly than OS-1 cells (by 15, 22, and 29 days), although the rate of microscopic and macroscopic metastasis between the two groups on Day 36 when the experiments were terminated was not different based on imaging (p=0.35) or histopathology (p=0.77). The different metastatic propensity of OS-1 and OS-2 was confirmed histologically as illustrated in FIG. 9.

FIG. 23 is a table that illustrates that the OS-1 and OS-2 xenografts show differential rates of tumor progression. As shown in FIG. 23, the progress of OS-2 xenograft tumors (as determined by measured in change in tumor volume) was significantly more rapid than the progress of the OS-1 xenograft tumors from 22-43 days post-injection.

FIG. 24 is a table that illustrates a MetaCore analysis identifying pathways for murine genes that are differentially expressed between OS-1 and OS-2 xenograft tumors. The top 10 most enriched pathways, shown in FIG. 24, suggest immune and inflammatory themes that modulate IL-17, TGF-beta signaling, the complement system, and patterning behavior and cytoskeletal remodeling with involvement of Rho GTPases. Analysis of the 482 murine genes identified as differentially expressed between OS-1 and xenograft tumors was performed with MetaCore software (https://portal.genego.com/) to show the top 10 processes and pathways ranked in terms of the enrichment of the common target-related genes (p-value).

FIG. 25 is a table identifying upstream regulators of differentially-expressed murine genes in OS-2 xenograft tumors as compared to OS-1 xenograft tumors. These upstream regulators of the 482 differentially expressed murine genes were observed using IPA. The most significant, predicted activated upstream regulators in OS-2 (worse prognosis), relative to OS-1 tumor xenografts were CEBPB and NFKB1 (p-value 5.54E-10 and 3.94E-09, respectively), whereas the most significant, predicted inhibited upstream regulator was MEF2C (p-value 2.54E-23) (FIG. 25). The retinoblastoma tumor suppressor gene (RB1) was also among the predicted significant upstream regulators (p-value 1.25E-04) showing inactivation in OS-2 xenograft tumors, as otherwise may have predicted based on previous studies. The differentially expressed murine genes were determined by pair-wise Exact Test comparisons in EdgeR. IPA was used to determine upstream modulators of the 482 differentially expressed genes and their predicted activities. Predicted activity based on gene expression values in OS-2 xenografts relative to OS-1 xenografts. A Z-score >2 indicates activation, while a Z-score <−2 indicates inactivation.

FIG. 26 is a table identifying upstream regulators of the upregulated murine genes in OS-2. The upstream regulators predicted to modulate expression and activity of the 240 upregulated murine genes expressed in the OS-2 tumor xenografts included the T-helper cell type-17 (Th17) activating cytokines TGF-β (p-value 1.26E-27), IL-1B (p-value 9.07E-25), and IL-6 (p-value 9.03E-22). Differentially expressed genes were determined by pair-wise Exact Test comparisons in EdgeR. IPA was used determined upstream modulators of the 240-upregulated murine genes in OS-2 xenografts. Predicted activity based on gene expression values in OS-2 xenografts. A Z-score >2 indicates activation, while a Z-score <−2 indicates inactivation.

FIG. 27 provides a table indicating upstream regulators of downregulated murine genes in OS-2 xenografts relative to OS-1 xenografts. The top upstream regulators predicted to modulate expression and activity of the 244 downregulated murine genes in the OS-2 xenografts were MEF2C and MYOD1 (p-value 1.15E-24 and 2.16E-15, respectively). MEF2C and MYOD1, both predicted as being inhibited in OS-2 xenografts and activated in OS-1 tumors, are important in promoting transcription of muscle-specific target genes and play a role in muscle differentiation. Differentially expressed genes were determined by pair-wise Exact Test comparisons in EdgeR. IPA was used determined upstream modulators of the 242-downregulated murine genes in OS-2 xenografts. Predicted activity based on gene expression values in OS-2 xenografts. A Z-score >2 indicates activation, while a Z-score <−2 indicates inactivation.

Figure 28A:
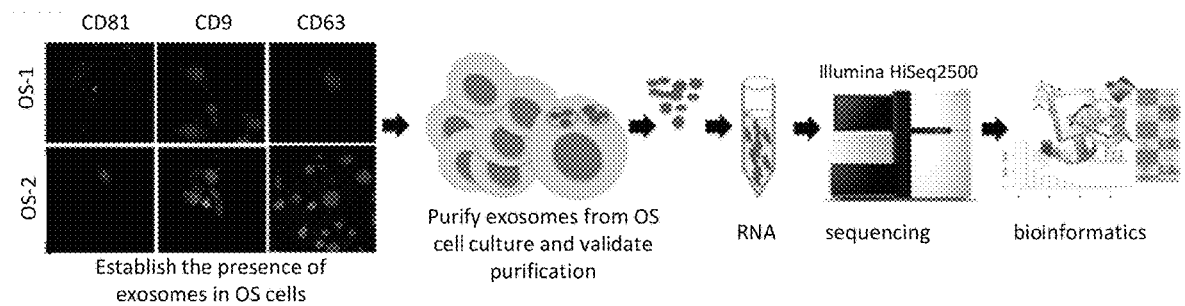
FIGS. 28A-28C are graphical representations of a workflow by which RNA contents of OS-derived exosomes from cultured cells may be defined using next-generation sequencing, and outcomes of example of data analyses performed on data derived from the workflow indicating that exosomes from OS-1 and OS-2 contain transcripts involved in different cell behaviors.
Figure 28B:
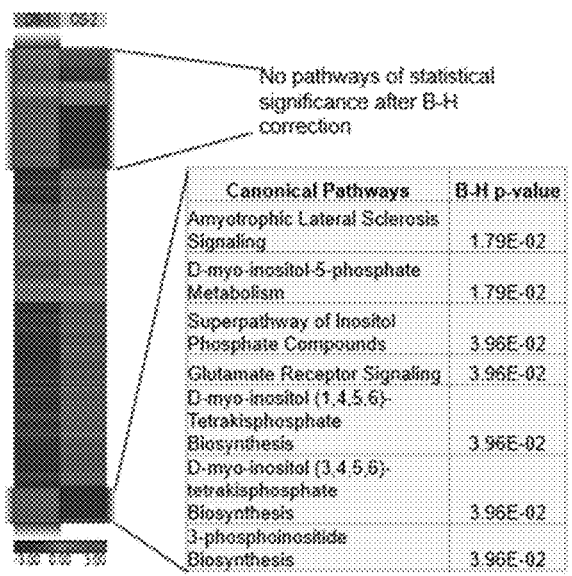
Figure 28C:
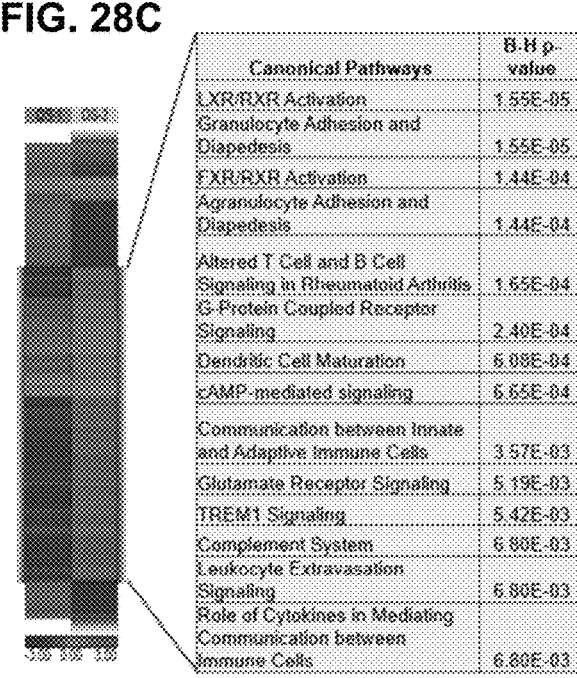

FIGS. 28A-28C are graphical representations of a workflow by which RNA contents of OS-derived exosomes from cultured cells may be defined using next-generation sequencing, and outcomes of example of data analyses performed on data derived from the workflow indicating that exosomes from OS-1 and OS-2 contain transcripts involved in different cell behaviors. FIG. 28A illustrates that an example workflow may include establishing the presence of exosomes in OS cultured cells, purifying the exosomes from OS cell culture and validating the purification, isolating RNA molecules, sequencing the RNA molecules, and then performing bioinformatics analysis on the resulting sequences to determine the identity of the RNA molecules, as well as other characteristics of the RNA molecules. For example, as shown in FIGS. 28B and 28C, other characteristics of the RNA molecules that may be determined by the bioinformatics analysis of FIG. 28A may include identifying pathways and cell behaviors associated with genes corresponding to the sequenced RNA molecules. For example, the heatmap and table of FIG. 28B indicate that OS-1 derived exosomes may contain RNA associated with genes involved in cellular signaling and metabolism, whereas the heatmap and table of FIG. 28C indicate that OS-2 derived exosomes may contain RNA associated with genes involved in communication between innate and adaptive immune cells.

FIGS. 29A-29C are graphical representations of a workflow by which RNA contents of OS-derived exosomes from cultured cells may be defined, and outcomes of example data analyses performed on data derived from the workflow indicating that decreased expression of cytokines may be found in fibroblasts treated with OS-2 derived exosomes. FIG. 29A illustrates that an example workflow may include culturing a test group of fibroblasts with exosomes derived from OS cells (with a phenotype of either OS-1 or OS-2), and culturing a control group of fibroblasts without exosomes derived from OS cells. The workflow may further include isolating RNA from the groups of fibroblasts, sequencing the RNA molecules, and then performing bioinformatics analysis on the resulting sequences to determine the identity of the RNA molecules and differences in gene expression between the test fibroblasts that were cultured with OS exosomes and the control fibroblasts that were cultured without OS exosomes. FIG. 29B is a table indicating differentially-expressed genes identified in fibroblasts that were cultured with OS-1 exosomes, as compared to fibroblasts cultured with OS-2 exosomes and/or as compared to fibroblasts cultured without OS exosomes. FIG. 29C is a table indicating differentially-expressed genes identified in fibroblasts that were cultured with OS-2 exosomes, as compared to fibroblasts cultured with OS-1 exosomes and/or as compared to fibroblasts cultured without OS exosomes. In the illustrated example of FIGS. 29A-29C, the RNA sequences derived from the fibroblasts cultured with OS-2 exosomes indicated that such fibroblasts had decreased expression of cytokines as compared to fibroblasts cultured with OS-1 exosomes and/or as compared to fibroblasts cultured without OS exosomes.

Figure 30A:
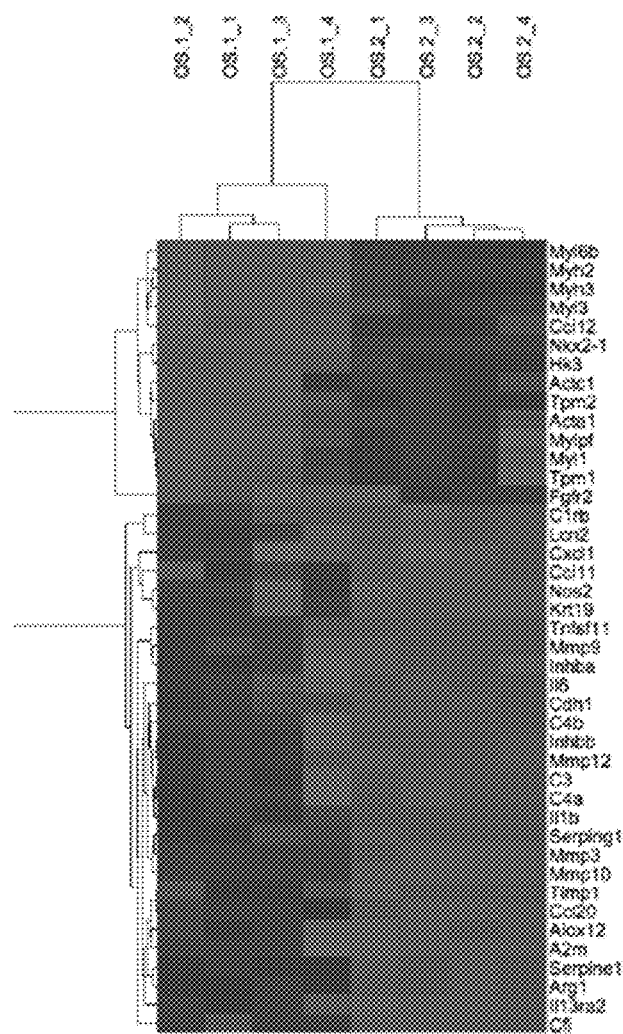
FIGS. 30A and 30B are graphical representations of differentially expressed mouse genes.
Figure 30B:
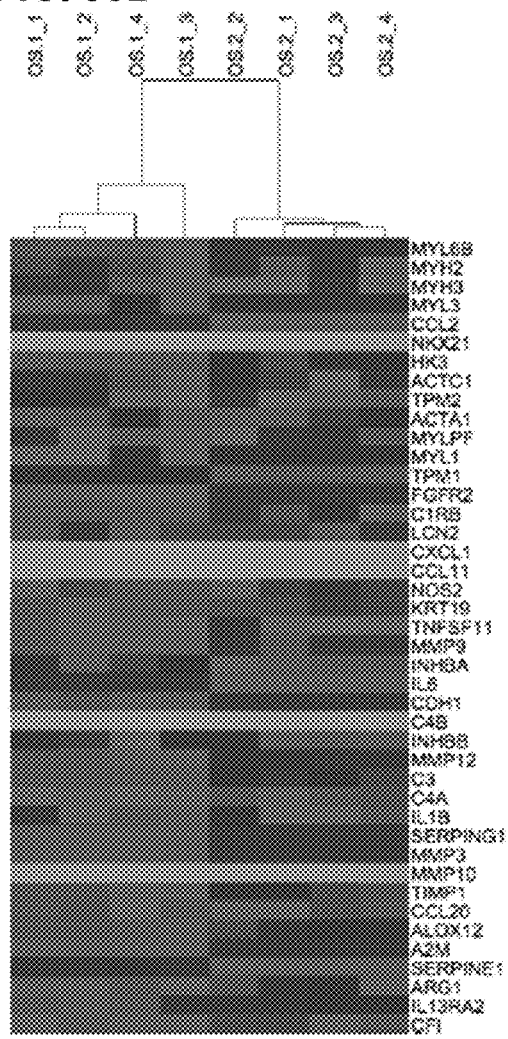

FIGS. 30A and 30B are graphical representations of differentially expressed mouse genes. The heatmaps depicted in FIGS. 30A and 30B illustrate top differentially expressed genes (mouse) identified by MetaCore Analysis, and indicates that different platforms and different methods of measuring gene expression and analyzing resulting data may produce consistent results.

Figure 31A:
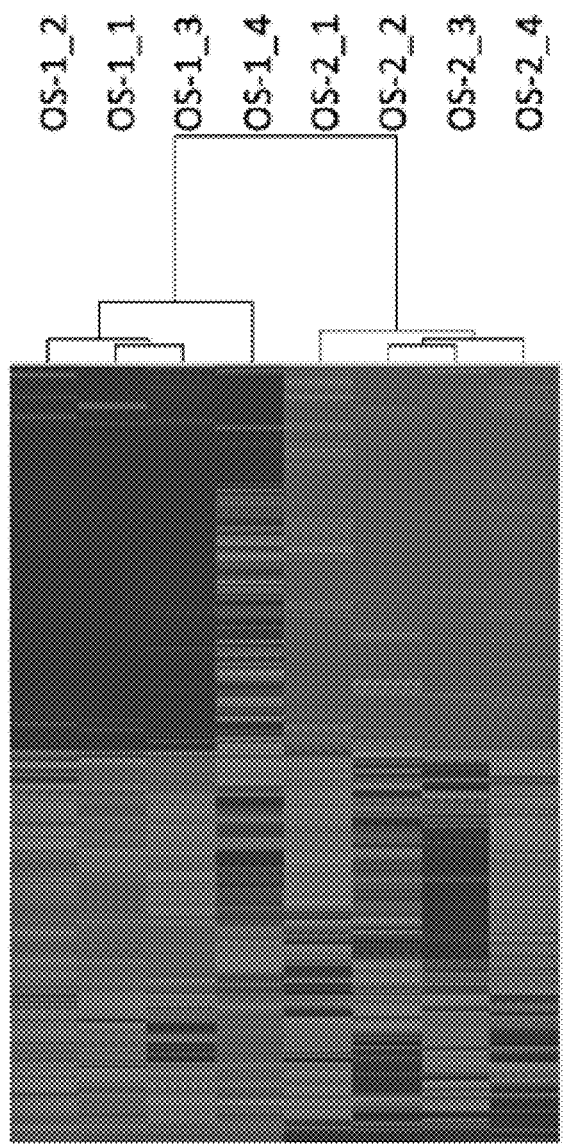
FIGS. 31A and 31B are graphical representations of differentially expressed mouse genes and canine orthologs of the mouse genes.
Figure 31B:
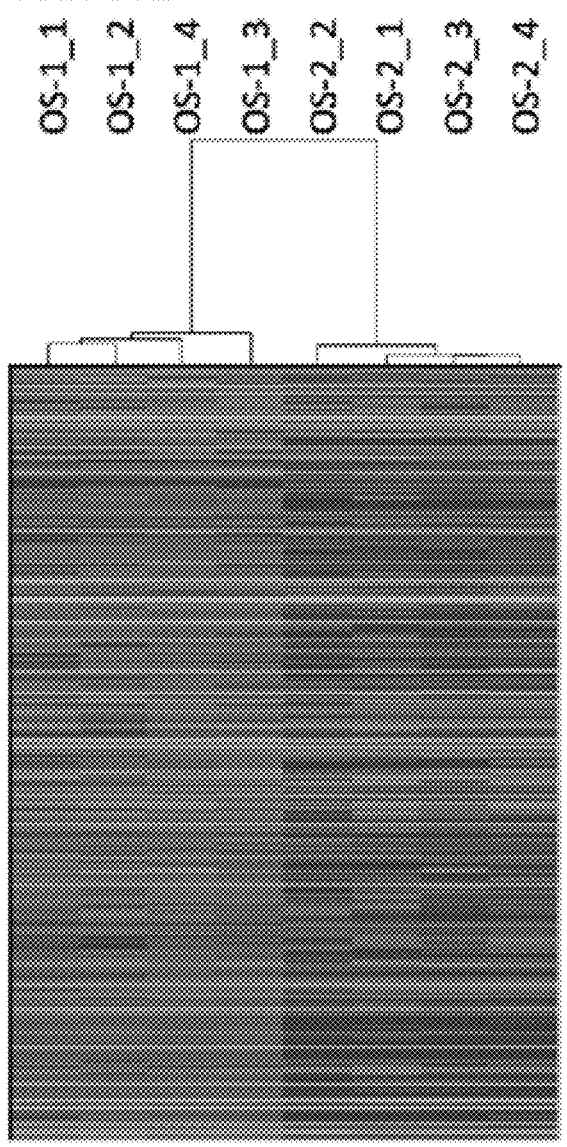

FIGS. 31A and 31B are graphical representations of differentially expressed mouse genes and canine orthologs of the mouse genes. The differentially-expressed mouse genes are depicted by the heatmap in FIG. 31A, and the canine orthologs of the differentially-expressed mouse genes are depicted in the same order by the heatmap in FIG. 31B. FIGS. 31A and 31B illustrate that the differential expression of mouse transcripts (e.g., mRNA profiles) in exosomes isolated from mice harboring OS-1 or OS-2 xenografts was not due to spurious mapping of canine genes to the mouse genome.

Figure 32:
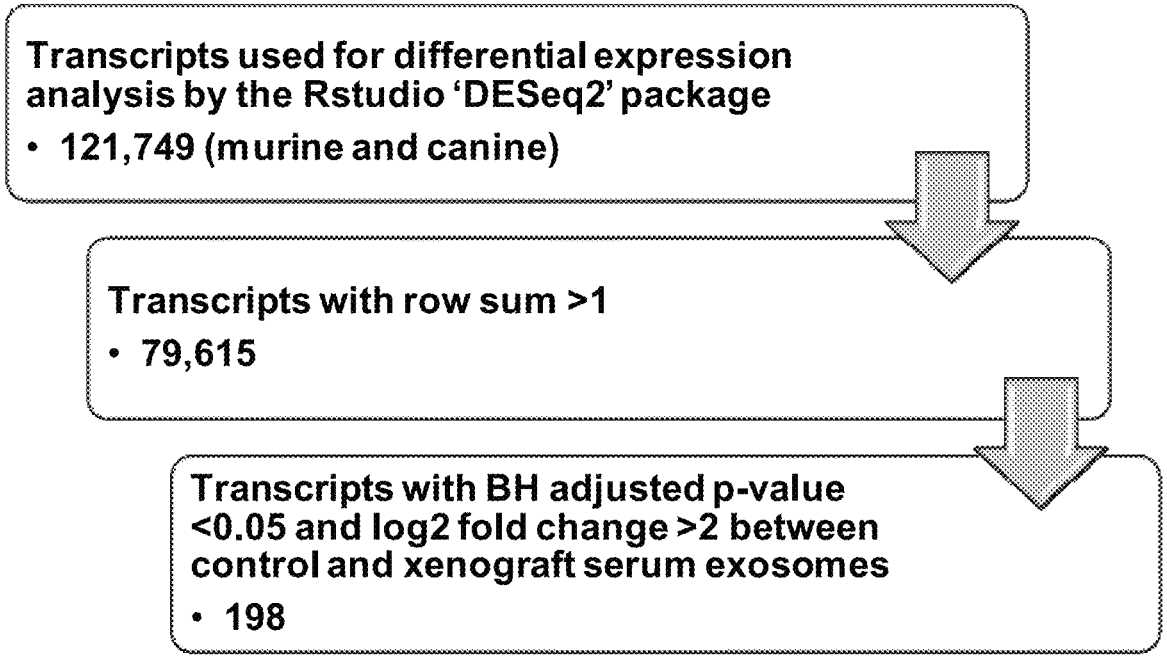
FIG. 32 is a graphical illustration of a bioinformatics method that shows the number of transcripts at each step of differential expression analysis.

FIG. 32 is a graphical illustration of a bioinformatics method that shows the number of transcripts at each step of differential expression analysis. The 'DESeq2' package in RStudio (version 0.99.491) was used for differential analysis of transcript counts obtained from Kallisto data. Transcript counts were first summarized to gene counts and then DESeq2 was used to convert count values to integer mode, correct for library size, and estimate dispersions and log 2 fold changes between comparison groups. Genes with a BH adjusted p-value <0.05 and log 2 fold change >+/−2 between control and xenograft samples were called significant. Statistically differentially expressed canine genes were removed if they had a DeSeq2 normalized value of greater than zero in the control (mouse sequences), as these may be genes that are highly homologous between the mouse and canine).

FIG. 33A-33C are is graphical representations of 198 differentially expressed transcripts. FIG. 33A is a heatmap representing all 198 differentially expressed transcripts. FIGS. 33B and 33C are close-up portions of the heatmap of FIG. 33A that respectively represent mouse- and dog-specific transcripts.

Figure 34A:
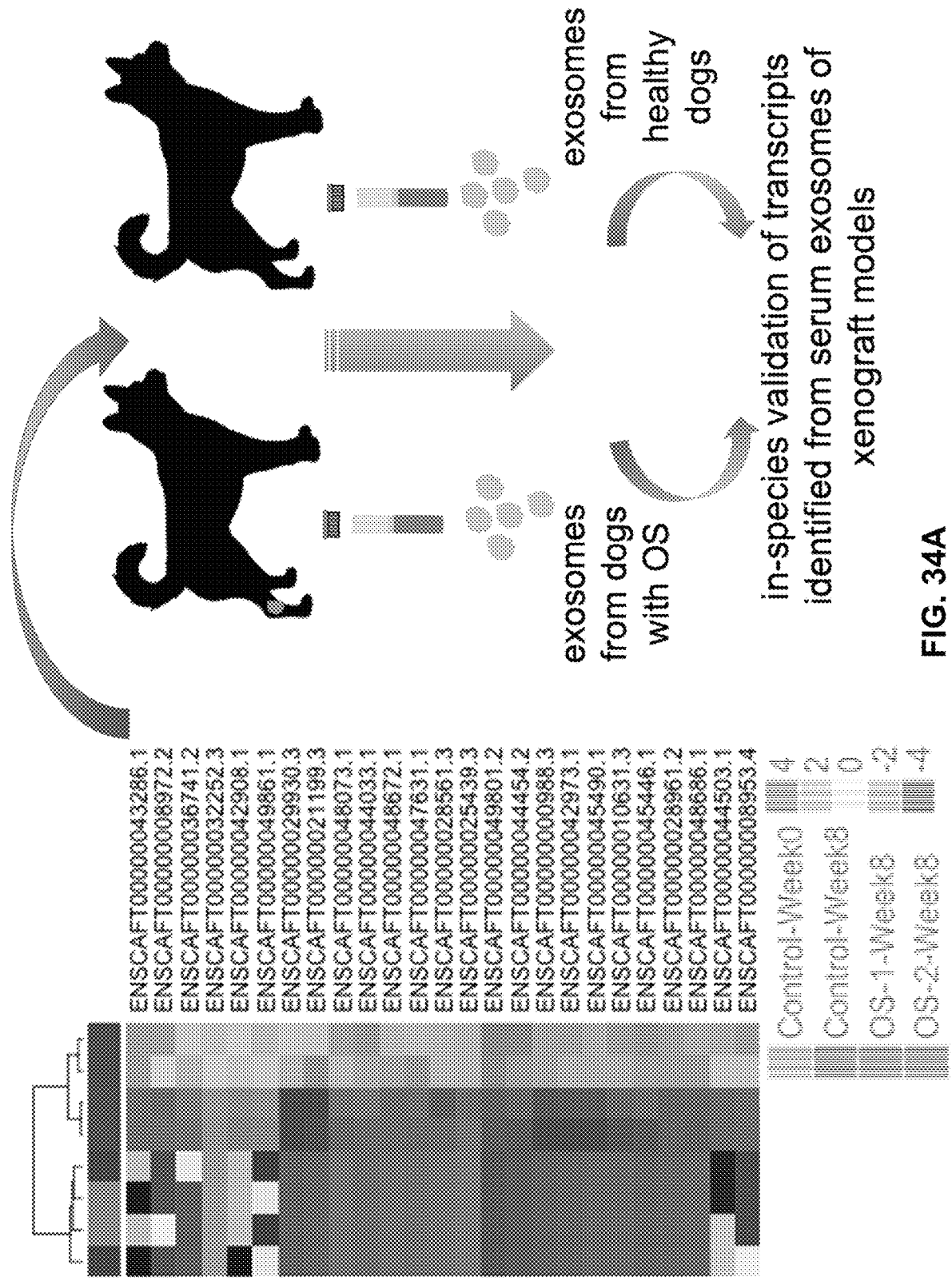
Figure 34B:
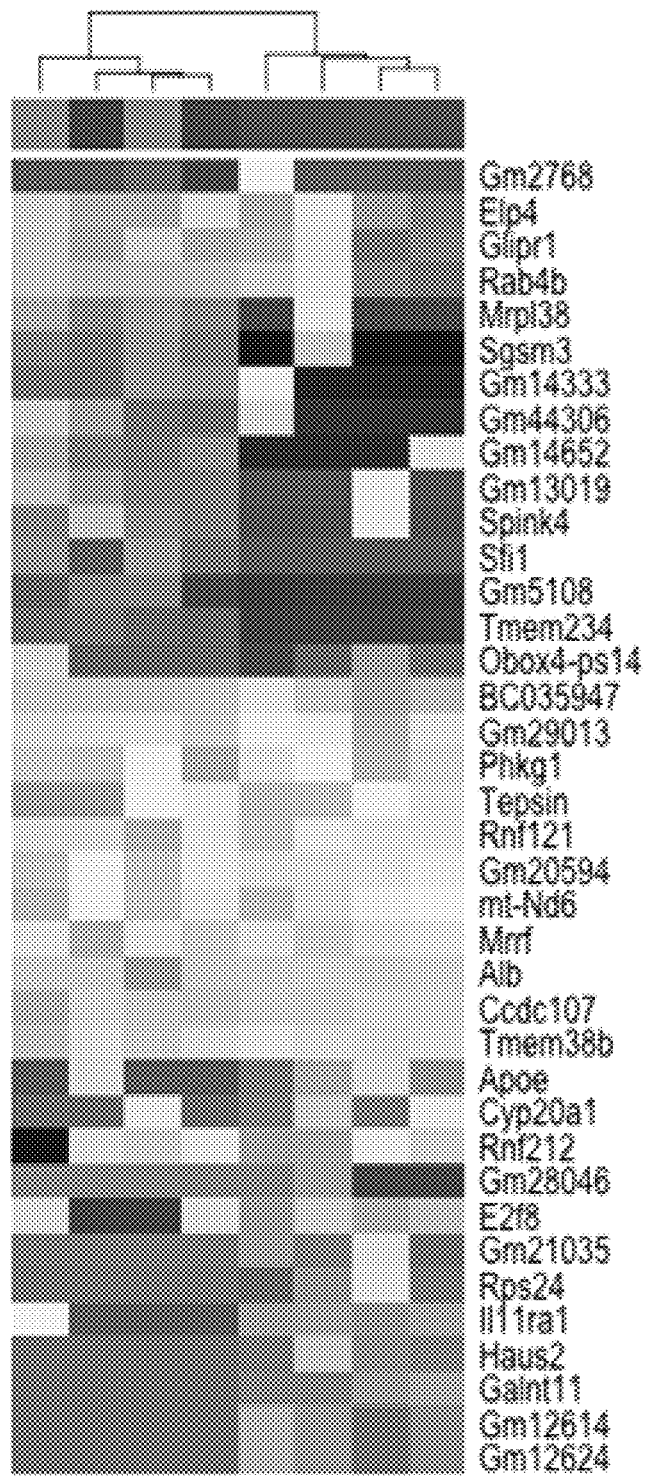

FIGS. 34A-34D are graphical representations of the detection of biomarkers of disease and host response. FIG. 34A is a heatmap of 25 most differentially expressed dog transcripts identified by statistical with DESeq2, which may be validated in dog patients with spontaneous osteosarcoma, and incudes a graphical representation of a cycle in which exosomes from dogs with osteosarcoma and healthy dogs is used for in-species validation of transcripts identified from serum exosomes of xenograft models. FIG. 34B is a heatmap of 38 differentially expressed mouse genes. FIG. 34C illustrates significant pathways, and FIG. 34D illustrates a top network (cell cycle) identified by IPA as being associated with differentially expressed host (mouse) genes shown in FIG. 34B.

In the example described herein, mouse xenografts were used to study the heterogeneity and biological behavior of OS in vivo. Specifically, this approach creates opportunities to examine tumor-intrinsic properties, as well as organotypic, tumor-stromal interactions that influence tumor progression. Cells were injected at the orthotopic site to simulate the biology of the spontaneous disease. The anatomical site of implantation may be considered carefully, as the biological behavior of tumors is dependent on both the intrinsic properties of tumor cells and host factors that differ between tissues and organs. The microenvironment in subcutaneous xenografts consists of desmoplastic mouse stromal cells that do not resemble the organization seen in autochthonous tumors. These properties also apply to OS: orthotopic canine OS xenografts in nude mice produced osteoid matrix and metastasized spontaneously, while subcutaneous xenografts did not.

The data show that heterogeneity of biological behavior (including metastatic propensity) can be recapitulated to a limited extent in tumors from cell lines, but more readily by utilizing multiple cell lines that cover the spectrum of tumor behavior. Further, the data show that the major genetic drivers that distinguish the two canine OS cell lines in vitro were retained in the orthotopic xenografts. In addition to stability of the transcriptome, the cell lines show stable morphology from the primary canine tumors to the primary orthotopic tumors, and to the metastatic tumors. Confirmation of genetic and morphologic stability over many passages was validated the utility of the present model to understand OS tumor heterogeneity.

As predicted from the original behavior of the spontaneous tumors in the dogs and from their gene and microRNA expression signatures, the logarithmic expansion phase of OS-2 primary xenografts was faster than that of OS-1 primary xenografts. However, both cell lines seemed to reach the tumor endpoints at approximately the same time. Two factors might account for this. First, the tumors are growing within a cavity surrounded by bone, and despite the fact that OS-2 xenografts showed greater epiphyseal destruction and invasion, the bone constrains the maximum size achievable by the primary tumors within the experimental time frame. Second, mice with OS-2 xenografts did not show greater morbidity than mice with OS-1 xenografts, determined by the absence of lameness, ambulatory deficits, and other behaviors associated with chronic pain. This could be due to adaptive behavior of prey species to hide pain; however, previous work has shown that painful intramedullary bone tumors produce behavioral changes in mice. It should be noted that these cell lines accurately represent the biological behavior of the tumors from which they were originally derived, and more broadly the classification of more aggressive and less aggressive tumors. Furthermore, such properties have been verified independently by other groups using one of these cell lines, and they generally extend to human and murine osteosarcoma.

Beyond growth at the primary site, biological behavior can be quantified by metastatic propensity and successful spread to distant sites. Again, the predictions from the original spontaneous tumors were confirmed experimentally in the models described herein. OS-2 cells were a representative example from a group of highly aggressive tumors (worse prognosis) that showed high expression of cell cycle and DNA damage repair associated genes, with concomitant reduced expression of a complement of genes that defined "microenvironment interactions. This reduced expression of molecules that mediate local cell communication could explain, at least in part, the observation that cells injected intratibially achieved rapid systemic distribution, spreading to the lungs within 6 hours; i.e., there was nothing to hold the cells in place, and they had no preference to remain in the local bone environment.

The results suggest that even though both OS-1 and OS-2 cell lines can establish a metastatic niche, they do so with different kinetics, creating a suitable model to study intrinsic differences in metastatic propensity, as well as host-related factors that contribute to the metastatic niche in OS.

Based on these observations, two distinct mechanisms for the different metastatic potential of OS-1 and OS-2 xenografts are herein proposed. OS-2 cells might have greater metastatic potential due to their interaction with the local microenvironment in the bone, which leads to reduced retention, and potentially to an increased capability to condition the distant site. The alternative possibility is that OS-2 cells seed the lungs shortly after inoculation, and even though many of these cells might leave the lungs or die, accounting for the loss of luciferase signal by 24 hours, some cells remain and eventually form the pulmonary lesions (i.e., equivalent to seeding or colonization by intravenous inoculation). Preliminary experiments suggest that OS-1 and OS-2 cells have low efficiency of pulmonary colonization upon intravenous injection which would indicate the first possibility occurs.

Highly expressed mouse genes present in the OS-2 xenografts were associated with B cell signaling, inflammation, and immune response, whereas mouse genes in the OS-1 cells xenografts were associated with patterning, and especially with muscle formation. Increased expression of myogenic regulators in mouse stromal cells in OS-1 xenografts raises interesting questions regarding possible effects of OS-1 tumor cells on marrow derived mesenchymal stromal cells.

Intriguingly, the most downregulated murine gene in the OS-2 xenografts was the transcription factor Nkx2-1, which is known to regulate lung epithelial cell morphogenesis and differentiation. Down-regulation of NKX2-1 has been shown to precede dissemination of lung adenocarcinoma cells. NKX2-1 amplification has been reported in one human OS patient but there are no reports of down regulation or loss of NKX2-1 in OS patients.

Thus, xenograft models that recapitulated the heterogeneous biological behavior of OS have been developed and have been described herein. These models may be useful to understand the mechanisms that drive progression and metastasis of OS, as they are expandable into additional cell lines to represent a wider spectrum of disease.

Materials and Methods

Cells and culture conditions: Two canine OS cell lines representing previously described "highly aggressive" and "less aggressive" molecular phenotypes (OS-1 and OS-2), were used in this study. OS-1 and OS-2 are derivatives of the OSCA-32 and OSCA-40 and OSCA-40 cell lines. Specifically, OS-1 represents a subline that successfully established tumors after orthotopic implantation, as the parental OSCA-32 did not establish heterotopic or orthotopic tumors in every occasion. OS-2 represents the parental OSCA-40, which reliably formed tumors after orthotopic implantation in every experiment done.

Cell lines were validated using STR Short Tandem Repeats (STR) profiles by DNA Diagnostics Center (DDC Medical) (Fairfield, Ohio). OS-1 and OS-2 cells were modified to stably express green fluorescent protein (GFP) and firefly luciferase as described (Scott et al., 2015) and used for orthotopic injections in mice. After transfection and selection, it was confirmed that the GFP/luciferase construct was stably integrated in each cell line by fluorescence in situ hybridization, and it was corroborated that the two cell lines had approximately equivalent luciferase activity on a per cell basis using conventional luciferase assays. All cell lines were grown in DMEM (Gibco, Grand Island, N.Y.) containing 5% glucose and L-glutamine, supplemented with 10% fetal bovine serum (Atlas Biologicals, Fort Collins, Colo.), 10 mM4-(2-hydroxyethyl)-1-piperazine ethanesulphonic acid buffer (HEPES) and 0.1% Primocin (Invivogen, San Diego, Calif.) and cultured at 37° C. in a humidified atmosphere of 5% $CO_2$. Canine OS cell lines are available for distribution through Kerafast, Inc. (Boston, Mass.). Each cell line was passaged more than 15 times before the experiments when they were inoculated into mice.

Mice: Six-week old, female, athymic nude mice (strain $NCr^{nu/nu}$) were obtained from Charles River Laboratories (Wilmington, Mass.). The University of Minnesota Institutional Animal Care and Use Committee approved protocols for mouse experiments of this study (Protocol No.: 1307-30806A).

Tumor xenografts: Eight animals per group provide >95% power to identify a 15% change in the median time to tumor when the σ for both populations is <2.0 and the acceptable α error is 5% (p<0.05). Experimental replicates increased statistical robustness, accounting for the expected heterogeneity.

Four replicate experiments were done to assess orthotopic growth and metastatic dissemination of OS-1 and OS-2 cells. For the first pilot experiment, groups of three mice were used to validate the approach. All of the mice receiving OS-1 xenografts showed successful implantation, but only two of the three mice receiving OS-2 xenografts showed successful implantation. For the second experiment, groups of 16 mice were used to establish significance. In this experiment, all of the mice receiving OS-2 xenografts showed successful implantation, but eight mice injected with OS-1 xenografts had significant adverse effects during anesthesia and were not recovered (i.e., they were humanely euthanatized). For the third experiment, nine mice were inoculated with OS-2 cells to verify the unexpected effects of rapid dissemination to the lung. No mice received OS-1 for this experiment. Finally, for the fourth experiment, five mice were inoculated with each cell line (OS-1 and OS-2) to achieve a biological replicate of experiment two, maintaining the sample size at a number to maximize a positive outcome. Appropriate censoring was used to include all animals in the analyses, only excluding any which succumbed acutely or subacutely during the intratibial injection procedure. Thus, 16 mice inoculated with OS-1 were included in the analyses of tumor growth, and 32 mice inoculated with OS-2 were included in the analyses of tumor growth.

It was previously determined that four samples per group approximate the point of minimal returns using large genomic datasets for gene expression profiling, and these estimates hold true from microarrays to RNAseq where the fidelity of replication within samples is high, despite orders of magnitude more data (see analysis of RNA sequencing below).

Animals were assigned to separate cages (4 animals each) in random order for each experiment. All of the animals in each cage received the same treatment. OS-1 and OS-2 cells expressing GFP and firefly luciferase were injected intratibially. Mice were anesthetized with xylazine (10 mg/kg, I.P.) and ketamine (100 mg/kg, I.P.), and $1\times10^5$ cells suspended in 10 µl of sterile PBS were injected into the left tibia using a tuberculin syringe with 29-gauge needle. Buprenorphine (0.075 mg/kg, I.P. q.8 hours; Buprenex®, Reckitt Benckiser Healthcare, Richmond, Va.) was used for pain control over the first 24 hours after injection of tumor cells, and prophylactic ibuprofen administrated in the water was used over the next 3.

Tumor growth was monitored by measuring width-and-length of the proximal tibia and the stifle joint weekly using calipers, as well as by in vivo imaging as described (Kim et al., 2014). Bioluminescence imaging (Xenogen IVIS spectrum, Caliper Life Sciences, Hopkinton, Mass.) was done after injection of D-luciferin (Gold biotechnology, St. Louis, Mo.) following isoflurane inhalant anesthesia and analyzed with Living Image Software (Caliper Life Sciences). Bone tissue volume was calculated from both tibiae using the equation $V=L\times W^2\times 0.52$ (Banerjee et al., 2013) and tumor volume was estimated by subtracting the normal bone tissue volume of the contralateral unaffected (right) tibia from the volume of the affected (left) tibia.

Mice were observed for up to 8 weeks or until tumor endpoint criteria were reached (ill thrift, tumor reaching 1 cm in the largest diameter, visible lameness, pain, or severe weight loss), at which time they were humanely euthanized with pentobarbital sodium and sodium phenytoin solution (Beuthanasia-D Special®, Schering-Plough Animal Health, Union, N.J.). Primary bone tumors and lung tissues were dissected and a portion of each was stored at −80° C. for RNA extraction. The remaining tissues were fixed in 10% neutral-buffered formalin, and processed for routine histological examination.

Luciferase activity and tumor sizes were compared using multiple t-test and Holm-Sidak method with Prism 6 software (GraphPad). p<0.05 was used as the level of significance.

RNA extraction, library preparation, and RNA sequencing: Total RNA was extracted from primary intratibial tumors and from cell lines using miRNeasy Mini Kit (QIAGEN, Valencia, Calif.). RNA integrity was examined using Agilent 2100 Bioanalyzer (Agilent Technologies, Santa Clara, Calif.) and RIN values of all samples were >8.0. Sequencing libraries were prepared with TruSeq Library Preparation Kit (Illumina, San Diego, Calif.). RNA sequencing (100-bp paired-end) with HiSeq 2500 (Illumina) was done at the University of Minnesota Genomics Center (UMGC). A minimum of ten million read-pairs was generated for each sample.

Analysis of RNA sequencing data: Initial quality control analysis of RNA sequencing (FASTQ) data for each sample was performed using the FastQC software (version 0.11.2) (Andrews). FASTQ data were trimmed with Trimmomatic (Bolger, 2014). HISAT2 (Kim et al., 2015) was used to map paired-end reads from eight xenograft tumors (four tumors of OS-1 and four tumors of OS-2) and four parental cell line samples (two each for OS-1 and OS-2 cell lines). For accurate alignment of sequencing reads to canine and murine genes within xenograft tumors a HISAT2 index for mapping was built from a multi-sequence fasta file containing both the canine (canFam3) and murine (mm10) genomes. Insertion size metrics were calculated for each sample using Picard software (version 1.126) (http://picard.sourceforge.net/). Samtools (version 1.0_BCFTools_HTSLib) was used to sort and index the bam files (Li et al., 2009). Transcript abundance estimates were generated using the Rsubread featureCounts program for differential gene expression analysis (Liao et al., 2014).

Gene counts for each xenograft sample were imported into RStudio (v. 3.2.3) for differential gene expression (DGE) analysis with EdgeR. Lowly expressed genes were removed by filtering. A gene was considered expressed if had log 2-transformed read counts per million (CPM) >1 in at least two of the eight xenograft tumors. Biological variation within xenograft sample groups was estimated by common dispersion and biological coefficient of variation (BCV) calculations. Pair-wise empirical analysis of differential gene expression was performed on sample groups (OS-1 and OS-2) using 'Exact Test' for two-group comparisons with trimmed mean of M-values (TMM) normalization (Robinson and Oshlack, 2010). Tagwise dispersion (individual dispersion for each gene) was used to adjust for abundance differences across biological replicates (n=4) within each xenograft group (OS-1 and OS-2). Gene counts as CPM, were imported into Partek Genomic Suite for clustering analysis and visualization. The Pearson similarity metric and average linkage clustering method were used for hierarchical clustering of mean-centered CPM values. Enriched pathway and functional classification analyses of DGEs were performed using IPA. The reference set for all IPA analyses was the Ingenuity Knowledge Base (genes only) and human Entrez gene names were used as the output format. To understand the high level functions and utilities that each gene identified as differentially expressed between OS-1 and OS-2 was associated with, Metacore software (Thompson Reuters) was used to identify statistically over-represented cellular processes in the dataset.

The following table, referred to above as Table S2, provides a list of differentially-expressed murine genes in OS-2 relative to OS-1 xenografts. Fold change (FC), p values, and FDR-adjusted p values were calculated by pair-wise Exact Test comparisons in EdgeR. Genes were annotated with the Ingenuity Knowledge Base of IPA.

| Gene | logFC | PValue | FDR | Entrez Gene Name | Location | Type(s) |
| --- | --- | --- | --- | --- | --- | --- |
| Nkx2-1 | −10.97163756 | 3.67E−43 | 2.51E−39 | NK2 homeobox 1 | Nucleus | transcription regulator |
| Zic1 | −10.37720965 | 2.80E−28 | 5.47E−25 | Zic family member 1 | Nucleus | transcription regulator |
| Kcnq2 | −7.93642633 | 1.90E−18 | 1.37E−15 | potassium channel, voltage gated KQT-like subfamily Q, member 2 | Plasma Membrane | ion channel |
| Smpd3 | −5.937398394 | 4.58E−11 | 4.93E−09 | sphingomyelin phosphodiesterase 3, neutral membrane (neutral sphingomyelinase II) | Cytoplasm | enzyme |
| Phex | −5.479136674 | 3.98E−13 | 7.78E−11 | phosphate regulating endopeptidase homolog, X-linked | Cytoplasm | peptidase |
| Fam43b | −5.16551588 | 7.72E−13 | 1.37E−10 | family with sequence similarity 43, member B | Other | other |
| Myoz2 | −5.031353137 | 1.21E−14 | 3.75E−12 | myozenin 2 | Other | other |
| Myh2 | −5.016278218 | 1.42E−10 | 1.37E−08 | myosin, heavy chain 2, skeletal muscle, adult | Cytoplasm | enzyme |
| Hoxd13 | −5.005651203 | 6.42E−16 | 2.83E−13 | homeobox D13 | Nucleus | transcription regulator |
| Slc13a5 | −4.983558827 | 3.64E−11 | 4.15E−09 | solute carrier family 13 (sodium-dependent citrate transporter), member 5 | Plasma Membrane | transporter |
| Panx3 | −4.824377849 | 2.74E−06 | 7.53E−05 | pannexin 3 | Plasma Membrane | other |
| Tmem145 | −4.602792152 | 2.02E−10 | 1.92E−08 | transmembrane protein 145 | Other | other |
| Lect1 | −4.567514167 | 5.15E−09 | 3.25E−07 | leukocyte cell derived chemotaxin 1 | Extracellular Space | other |
| Asic3 | −4.473594151 | 2.73E−14 | 7.19E−12 | acid sensing (proton gated) ion channel 3 | Plasma Membrane | ion channel |
| Ankrd2 | −4.445048104 | 2.61E−19 | 2.23E−16 | ankyrin repeat domain 2 (stretch responsive muscle) | Nucleus | transcription regulator |
| Fam180a | −4.444919786 | 1.04E−07 | 4.35E−06 | family with sequence similarity 180, member A | Other | other |
| Col9a1 | −4.397295279 | 2.52E−11 | 3.08E−09 | collagen, type IX, alpha 1 | Extracellular Space | other |
| Fabp3 | −4.367492217 | 2.88E−18 | 1.97E−15 | fatty acid binding protein 3, muscle and heart | Cytoplasm | transporter |
| Lyz1 | −4.308114309 | 0.000102599 | 0.001637874 | lysozyme | Extracellular Space | enzyme |
| Adamts18 | −4.303169665 | 3.57E−09 | 2.42E−07 | ADAM metallopeptidase with thrombospondin type 1 motif, 18 | Extracellular Space | peptidase |
| Sp7 | −4.224816491 | 1.29E−08 | 7.16E−07 | Sp7 transcription factor | Nucleus | transcription regulator |
| Omd | −4.186098129 | 2.89E−17 | 1.58E−14 | osteomodulin | Extracellular Space | other |
| 1700101I11Rik | −4.155168387 | 2.75E−07 | 9.92E−06 | RIKEN cDNA 1700101I11 gene | Other | other |
| Dlx6 | −4.109636472 | 3.22E−11 | 3.76E−09 | distal-less homeobox 6 | Nucleus | transcription regulator |
| Actn2 | −4.069827028 | 5.15E−17 | 2.71E−14 | actinin, alpha 2 | Nucleus | transcription regulator |
| Tceal7 | −4.038267592 | 4.23E−06 | 0.000108501 | transcription elongation factor A (SII)-like 7 | Nucleus | transcription regulator |
| Xirp2 | −4.014810326 | 6.23E−10 | 5.33E−08 | xin actin binding repeat containing 2 | Other | other |
| Paqr6 | −3.961900754 | 2.42E−10 | 2.28E−08 | progestin and adipoQ receptor family member VI | Plasma Membrane | other |

-continued

| Gene | logFC | PValue | FDR | Entrez Gene Name | Location | Type(s) |
|---|---|---|---|---|---|---|
| Csrp3 | −3.936461238 | 8.12E−11 | 8.23E−09 | cysteine and glycine-rich protein 3 (cardiac LIM protein) | Nucleus | other |
| Fcrls | −3.810649791 | 2.99E−37 | 1.36E−33 | Fc receptor-like S, scavenger receptor | Plasma Membrane | other |
| Ckmt2 | −3.806425077 | 2.10E−09 | 1.55E−07 | creatine kinase, mitochondrial 2 (sarcomeric) | Cytoplasm | kinase |
| Myl6b | −3.787544034 | 9.99E−09 | 5.82E−07 | myosin, light chain 6B, alkali, smooth muscle and non-muscle | Cytoplasm | other |
| Gli1 | −3.740040126 | 9.38E−17 | 4.58E−14 | GLI family zinc finger 1 | Nucleus | transcription regulator |
| Zdbf2 | −3.73484272 | 1.50E−07 | 6.03E−06 | zinc finger, DBF-type containing 2 | Other | other |
| Opn1mw | −3.726345151 | 8.04E−07 | 2.55E−05 | opsin 1 (cone pigments), long-wave-sensitive | Plasma Membrane | G-protein coupled receptor |
| Gsg1l | −3.72152491 | 9.85E−10 | 8.07E−08 | GSG1-like | Plasma Membrane | other |
| Abra | −3.69798677 | 9.51E−13 | 1.65E−10 | actin binding Rho activating protein | Cytoplasm | other |
| Myom3 | −3.681916158 | 4.38E−08 | 2.07E−06 | myomesin 3 | Other | other |
| Serpinb1c | −3.657917675 | 4.90E−11 | 5.20E−09 | serine (or cysteine) peptidase inhibitor, clade B, member 1c | Extracellular Space | other |
| Foxg1 | −3.648321574 | 1.21E−19 | 1.14E−16 | forkhead box G1 | Nucleus | transcription regulator |
| Ifitm5 | −3.617680152 | 2.81E−09 | 2.03E−07 | interferon induced transmembrane protein 5 | Plasma Membrane | other |
| 9130024F11Rik | −3.490015735 | 2.34E−12 | 3.72E−10 | RIKEN cDNA 9130024F11 gene | Other | other |
| Csmp3 | −3.450251912 | 1.48E−06 | 4.37E−05 | cysteine-serine-rich nuclear protein 3 | Nucleus | transcription regulator |
| Slc47a1 | −3.443994582 | 2.09E−06 | 5.96E−05 | solute carrier family 47 (multidrug and toxin extrusion), member 1 | Plasma Membrane | transporter |
| 2410137F16Rik | −3.441108061 | 6.33E−07 | 2.07E−05 | #N/A | #N/A | #N/A |
| A930003A15Rik | −3.43849311 | 7.11E−08 | 3.21E−06 | RIKEN cDNA A930003A15 gene | Other | other |
| Col11a2 | −3.43289575 | 9.67E−09 | 5.68E−07 | collagen, type XI, alpha 2 | Extracellular Space | other |
| Cst6 | −3.420908168 | 2.33E−07 | 8.66E−06 | cystatin E/M | Extracellular Space | other |
| Actc1 | −3.400606916 | 1.73E−07 | 6.78E−06 | actin, alpha, cardiac muscle 1 | Cytoplasm | enzyme |
| Atp1b4 | −3.352991208 | 2.08E−05 | 0.000425726 | ATPase, Na+/K+ transporting, beta 4 polypeptide | Plasma Membrane | transporter |
| Al4pk2 | −3.341104185 | 9.43E−05 | 0.001527325 | alpha-kinase 2 | Nucleus | kinase |
| Myh1 | −3.324236394 | 1.55E−09 | 1.18E−07 | myosin, heavy chain 1, skeletal muscle, adult | Plasma Membrane | enzyme |
| Hspb3 | −3.317439048 | 1.86E−08 | 9.63E−07 | heat shock 27 kDa protein 3 | Cytoplasm | other |
| Itgb1bp2 | −3.311620649 | 2.66E−09 | 1.93E−07 | integrin beta 1 binding protein (melusin) 2 | Other | other |
| Casq2 | −3.292086149 | 1.53E−08 | 8.17E−07 | calsequestrin 2 (cardiac muscle) | Cytoplasm | other |
| Dmp1 | −3.257994756 | 1.22E−09 | 9.51E−08 | dentin matrix acidic phosphoprotein 1 | Extracellular Space | other |
| Plb1 | −3.242320263 | 4.00E−07 | 1.39E−05 | phospholipase B1 | Cytoplasm | enzyme |
| Cacna2d2 | −3.241001086 | 1.16E−09 | 9.20E−08 | calcium channel, voltage-dependent, alpha 2/delta subunit 2 | Plasma Membrane | ion channel |
| AU022793 | −3.198508581 | 2.72E−06 | 7.49E−05 | expressed sequence AU022793 | Other | other |
| Mylpf | −3.196418301 | 5.32E−07 | 1.77E−05 | myosin light chain, phosphorylatable, fast skeletal muscle | Cytoplasm | other |
| Xirp1 | −3.193088545 | 6.65E−12 | 9.38E−10 | xin actin binding repeat containing 1 | Plasma Membrane | other |
| Dok7 | −3.156216975 | 4.84E−09 | 3.08E−07 | docking protein 7 | Extracellular Space | other |

-continued

| Gene | logFC | PValue | FDR | Entrez Gene Name | Location | Type(s) |
|---|---|---|---|---|---|---|
| Hsd11b2 | −3.155020704 | 5.80E−10 | 5.06E−08 | hydroxysteroid (11-beta) dehydrogenase 2 | Cytoplasm | enzyme |
| Fat3 | −3.116929351 | 9.82E−07 | 3.04E−05 | FAT atypical cadherin 3 | Plasma Membrane | other |
| Bex1 | −3.098852594 | 5.93E−07 | 1.96E−05 | brain expressed gene 1 | Other | other |
| Siglec1 | −3.056322266 | 5.56E−36 | 1.52E−32 | sialic acid binding Ig-like lectin 1, sialoadhesin | Plasma Membrane | other |
| Klhl30 | −3.042670774 | 3.66E−12 | 5.38E−10 | kelch-like family member 30 | Other | other |
| Srpk3 | −3.036559842 | 8.83E−10 | 7.33E−08 | SRSF protein kinase 3 | Cytoplasm | kinase |
| Nmrk2 | −3.036504708 | 9.23E−08 | 3.94E−06 | nicotinamide riboside kinase 2 | Plasma Membrane | kinase |
| Hspb7 | −3.035223935 | 4.33E−12 | 6.23E−10 | heat shock 27 kDa protein family, member 7 (cardiovascular) | Cytoplasm | other |
| Hspb6 | −3.010038437 | 3.90E−11 | 4.38E−09 | heat shock protein, alpha-crystallin-related, B6 | Cytoplasm | other |
| Myh3 | −3.005412878 | 3.96E−09 | 2.63E−07 | myosin, heavy chain 3, skeletal muscle, embryonic | Cytoplasm | enzyme |
| Zim1 | −2.999002281 | 5.28E−07 | 1.77E−05 | zinc finger, imprinted 1 | Nucleus | other |
| Fhl1 | −2.971716832 | 7.50E−12 | 1.05E−09 | four and a half LIM domains 1 | Cytoplasm | other |
| Cryab | −2.942079665 | 4.57E−11 | 4.93E−09 | crystallin, alpha B | Nucleus | other |
| Col26a1 | −2.922599266 | 0.000140087 | 0.002118637 | collagen, type XXVI, alpha 1 | Extracellular Space | other |
| Tpm2 | −2.901026545 | 3.06E−11 | 3.67E−09 | tropomyosin 2, beta | Cytoplasm | other |
| Smpx | −2.8905869 | 3.29E−15 | 1.25E−12 | small muscle protein, X-linked | Cytoplasm | other |
| Mybpc1 | −2.889275402 | 7.51E−07 | 2.41E−05 | myosin binding protein C, slow type | Cytoplasm | other |
| Car3 | −2.883690634 | 3.67E−09 | 2.48E−07 | carbonic anhydrase III | Cytoplasm | enzyme |
| Myl3 | −2.879903468 | 1.51E−05 | 0.000327184 | myosin, light chain 3, alkali; ventricular, skeletal, slow | Cytoplasm | other |
| Acta1 | −2.858497666 | 2.23E−07 | 8.33E−06 | actin, alpha 1, skeletal muscle | Cytoplasm | other |
| Adprhl1 | −2.839594188 | 3.39E−09 | 2.36E−07 | ADP-ribosylhydrolase like 1 | Other | enzyme |
| Robo2 | −2.838080162 | 1.25E−06 | 3.77E−05 | roundabout guidance receptor 2 | Plasma Membrane | transmembrane receptor |
| Col9a2 | −2.836541279 | 9.14E−11 | 9.13E−09 | collagen, type IX, alpha 2 | Extracellular Space | other |
| Frzb | −2.822407749 | 2.37E−07 | 8.77E−06 | frizzled-related protein | Extracellular Space | other |
| Matn3 | −2.818890834 | 2.10E−05 | 0.000429131 | matrilin 3 | Extracellular Space | other |
| Vgll2 | −2.779983734 | 3.56E−09 | 2.42E−07 | vestigial-like family member 2 | Nucleus | transcription regulator |
| Alpl | −2.774474841 | 3.78E−13 | 7.49E−11 | alkaline phosphatase, liver/bone/kidney | Plasma Membrane | phosphatase |
| Cdo1 | −2.770636161 | 1.67E−08 | 8.76E−07 | cysteine dioxygenase type 1 | Cytoplasm | enzyme |
| Mfsd7c | −2.762027564 | 6.69E−07 | 2.18E−05 | feline leukemia virus subgroup C cellular receptor family, member 2 | Plasma Membrane | transporter |
| Crhr2 | −2.736336233 | 1.20E−11 | 1.54E−09 | corticotropin releasing hormone receptor 2 | Plasma Membrane | G-protein coupled receptor |
| Myadml2 | −2.724262402 | 4.46E−06 | 0.00011354 | myeloid-associated differentiation marker-like 2 | Cytoplasm | other |
| Pax2 | −2.719600255 | 9.94E−06 | 0.000228268 | paired box 2 | Nucleus | transcription regulator |
| Zic2 | −2.715698644 | 1.17E−05 | 0.000263232 | Zic family member 2 | Nucleus | transcription regulator |
| S100b | −2.709990606 | 1.76E−14 | 5.13E−12 | S100 calcium binding protein B | Cytoplasm | other |
| Synpo2l | −2.701441875 | 3.57E−09 | 2.42E−07 | synaptopodin 2-like | Cytoplasm | other |
| Cox6a2 | −2.693936484 | 4.57E−07 | 1.54E−05 | cytochrome c oxidase subunit VIa polypeptide 2 | Cytoplasm | enzyme |

| Gene | logFC | PValue | FDR | Entrez Gene Name | Location | Type(s) |
| --- | --- | --- | --- | --- | --- | --- |
| Gm6524 | −2.692410726 | 5.56E−05 | 0.000970923 | katanin p60 (ATPase-containing) subunit A1 pseudogene | Other | other |
| Ccrl1 | −2.676579274 | 2.47E−06 | 6.85E−05 | #N/A | #N/A | #N/A |
| Col22a1 | −2.674727987 | 3.90E−10 | 3.47E−08 | collagen, type XXII, alpha 1 | Extracellular Space | other |
| Cav3 | −2.673548764 | 1.73E−07 | 6.78E−06 | caveolin 3 | Plasma Membrane | enzyme |
| Slc38a3 | −2.654180586 | 6.41E−05 | 0.001092134 | solute carrier family 38, member 3 | Plasma Membrane | transporter |
| Tmem8c | −2.65326667 | 8.29E−06 | 0.000193267 | transmembrane protein 8C | Plasma Membrane | other |
| Klhl41 | −2.642347539 | 2.57E−07 | 9.39E−06 | kelch-like family member 41 | Cytoplasm | other |
| Des | −2.619769533 | 8.19E−12 | 1.11E−09 | desmin | Cytoplasm | other |
| Ldb3 | −2.619385875 | 7.34E−06 | 0.000173688 | LIM domain binding 3 | Cytoplasm | transporter |
| Sbk2 | −2.606775291 | 8.68E−05 | 0.001420753 | SH3 domain binding kinase family, member 2 | Other | other |
| Popdc2 | −2.58927308 | 2.98E−06 | 8.02E−05 | popeye domain containing 2 | Other | other |
| Snca | −2.588807158 | 4.55E−06 | 0.000115237 | synuclein, alpha (non A4 component of amyloid precursor) | Cytoplasm | other |
| Ogn | −2.586436671 | 3.77E−10 | 3.37E−08 | osteoglycin | Extracellular Space | growth factor |
| Lmod2 | −2.574611571 | 7.58E−07 | 2.43E−05 | leiomodin 2 (cardiac) | Other | other |
| Lepr | −2.568144399 | 1.03E−08 | 5.96E−07 | leptin receptor | Plasma Membrane | transmembrane receptor |
| Lrrc30 | −2.564534101 | 0.000103946 | 0.001655518 | leucine rich repeat containing 30 | Other | other |
| Tuba8 | −2.563554458 | 0.000319672 | 0.004213331 | tubulin, alpha 8 | Cytoplasm | other |
| Tceal5 | −2.557601315 | 5.74E−05 | 0.000995638 | transcription elongation factor A (SII)-like 5 | Other | other |
| Myot | −2.538095094 | 1.07E−05 | 0.000242622 | myotilin | Cytoplasm | other |
| Ndnf | −2.537156126 | 6.13E−10 | 5.28E−08 | neuron-derived neurotrophic factor | Extracellular Space | other |
| Ch25h | −2.531462006 | 3.17E−12 | 4.77E−10 | cholesterol 25-hydroxylase | Cytoplasm | enzyme |
| Lrtm1 | −2.531422723 | 0.000304181 | 0.004044222 | leucine-rich repeats and transmembrane domains 1 | Other | other |
| Yipf7 | −2.520519196 | 3.17E−06 | 8.47E−05 | Yip1 domain family, member 7 | Other | other |
| Rsad2 | −2.52017011 | 3.91E−08 | 1.88E−06 | radical S-adenosyl methionine domain containing 2 | Cytoplasm | enzyme |
| Myl1 | −2.508451421 | 8.20E−05 | 0.001356344 | myosin, light chain 1, alkali; skeletal, fast | Cytoplasm | other |
| Gm10767 | −2.507994364 | 1.62E−05 | 0.000344605 | predicted gene 10767 | Other | other |
| Col9a3 | −2.503274415 | 0.00020731 | 0.002966738 | collagen, type IX, alpha 3 | Extracellular Space | other |
| Pdlim3 | −2.502660067 | 9.22E−09 | 5.50E−07 | PDZ and LIM domain 3 | Plasma Membrane | other |
| Tnnc2 | −2.502251052 | 2.88E−05 | 0.000568941 | troponin C type 2 (fast) | Cytoplasm | other |
| Myom2 | −2.481140713 | 6.30E−07 | 2.07E−05 | myomesin 2 | Cytoplasm | other |
| Ccl4 | −2.473254523 | 1.56E−09 | 1.18E−07 | chemokine (C-C motif) ligand 4 | Extracellular Space | cytokine |
| Fgfr4 | −2.467767258 | 5.43E−05 | 0.000952702 | fibroblast growth factor receptor 4 | Plasma Membrane | kinase |
| Hand2 | −2.466208146 | 5.90E−05 | 0.001018934 | heart and neural crest derivatives expressed 2 | Nucleus | transcription regulator |
| Ppargc1a | −2.461171212 | 2.96E−05 | 0.000580045 | peroxisome proliferator-activated receptor gamma, coactivator 1 alpha | Nucleus | transcription regulator |
| Asb12 | −2.455387214 | 9.25E−05 | 0.001503012 | ankyrin repeat and SOCS box containing 12 | Nucleus | transcription regulator |
| Klhl40 | −2.453997338 | 1.87E−08 | 9.68E−07 | kelch-like family member 40 | Other | other |
| Hspa1l | −2.448496231 | 7.22E−10 | 6.10E−08 | heat shock 70 kDa protein 1-like | Cytoplasm | other |
| Srl | −2.437036897 | 2.82E−06 | 7.69E−05 | sarcalumenin | Cytoplasm | other |
| Fndc5 | −2.434034744 | 6.89E−06 | 0.000164402 | fibronectin type III domain containing 5 | Other | other |

| Gene | logFC | PValue | FDR | Entrez Gene Name | Location | Type(s) |
|---|---|---|---|---|---|---|
| Tnnt3 | −2.43394736 | 4.26E−05 | 0.000786196 | troponin T type 3 (skeletal, fast) | Cytoplasm | other |
| Greb1 | −2.426503014 | 1.19E−08 | 6.75E−07 | growth regulation by estrogen in breast cancer 1 | Cytoplasm | other |
| I830012O16Rik | −2.419437095 | 0.000180549 | 0.002630558 | #N/A | #N/A | #N/A |
| Sox11 | −2.416593585 | 3.33E−09 | 2.34E−07 | SRY (sex determining region Y)-box 11 | Nucleus | transcription regulator |
| Nrcam | −2.409994027 | 1.07E−05 | 0.000242622 | neuronal cell adhesion molecule | Plasma Membrane | other |
| Foxl1 | −2.40842338 | 5.02E−06 | 0.000124633 | forkhead box L1 | Nucleus | transcription regulator |
| Foxc1 | −2.3807345 | 1.25E−19 | 1.14E−16 | forkhead box C1 | Nucleus | transcription regulator |
| Tuba4a | −2.367985915 | 4.07E−07 | 1.41E−05 | tubulin, alpha 4a | Cytoplasm | other |
| Tcap | −2.362652632 | 7.01E−07 | 2.27E−05 | titin-cap | Cytoplasm | other |
| B430306N03Rik | −2.351177563 | 4.46E−07 | 1.51E−05 | RIKEN cDNA B430306N03 gene | Other | other |
| Cap2 | −2.351093169 | 7.43E−08 | 3.31E−06 | CAP, adenylate cyclase-associated protein, 2 (yeast) | Plasma Membrane | other |
| Ucp3 | −2.345743121 | 3.11E−05 | 0.00060655 | uncoupling protein 3 (mitochondrial, proton carrier) | Cytoplasm | transporter |
| Dmrta2 | −2.338686972 | 1.16E−06 | 3.53E−05 | DMRT-like family A2 | Nucleus | transcription regulator |
| Fgfr3 | −2.337098522 | 2.07E−11 | 2.60E−09 | fibroblast growth factor receptor 3 | Plasma Membrane | kinase |
| Mapt | −2.331242707 | 2.08E−08 | 1.06E−06 | microtubule-associated protein tau | Plasma Membrane | other |
| Fgfr2 | −2.32142915 | 2.02E−05 | 0.000418907 | fibroblast growth factor receptor 2 | Plasma Membrane | kinase |
| Hhatl | −2.311519505 | 2.06E−05 | 0.000424294 | hedgehog acyltransferase-like | Cytoplasm | enzyme |
| Jsrp1 | −2.307700559 | 7.35E−08 | 3.30E−06 | junctional sarcoplasmic reticulum protein 1 | Cytoplasm | other |
| Ppm1e | −2.302246505 | 7.68E−07 | 2.45E−05 | protein phosphatase, Mg2+/Mn2+ dependent, 1E | Nucleus | phosphatase |
| Flnc | −2.296173473 | 1.55E−07 | 6.21E−06 | filamin C, gamma | Cytoplasm | other |
| Smad9 | −2.295442355 | 7.21E−06 | 0.000171229 | SMAD family member 9 | Nucleus | transcription regulator |
| Alpk3 | −2.286390928 | 7.03E−07 | 2.27E−05 | alpha-kinase 3 | Nucleus | kinase |
| Npr3 | −2.28173834 | 5.37E−07 | 1.79E−05 | natriuretic peptide receptor 3 | Plasma Membrane | G-protein coupled receptor |
| Fras1 | −2.279123226 | 1.29E−07 | 5.32E−06 | Fraser extracellular matrix complex subunit 1 | Extracellular Space | other |
| Cmpk2 | −2.278794093 | 6.99E−06 | 0.000166661 | cytidine monophosphate (UMP-CMP) kinase 2, mitochondrial | Cytoplasm | kinase |
| Rbp7 | −2.276049923 | 1.43E−10 | 1.38E−08 | retinol binding protein 7, cellular | Cytoplasm | other |
| Popdc3 | −2.270239846 | 1.86E−07 | 7.13E−06 | popeye domain containing 3 | Other | other |
| Dusp26 | −2.262773674 | 1.97E−05 | 0.000409563 | dual specificity phosphatase 26 (putative) | Cytoplasm | enzyme |
| Slc28a2 | −2.26166738 | 3.16E−06 | 8.47E−05 | solute carrier family 28 (concentrative nucleoside transporter), member 2 | Plasma Membrane | transporter |
| Smyd1 | −2.257820234 | 1.29E−05 | 0.000287231 | SET and MYND domain containing 1 | Nucleus | transcription regulator |
| Tbx1 | −2.253565715 | 3.52E−09 | 2.42E−07 | T-box 1 | Nucleus | transcription regulator |
| Tnni2 | −2.250955521 | 0.000114204 | 0.001787671 | troponin I type 2 (skeletal, fast) | Cytoplasm | enzyme |
| Ccl3 | −2.249366721 | 9.28E−05 | 0.001506348 | chemokine (C-C motif) ligand 3-like 3 | Extracellular Space | cytokine |
| Slc16a4 | −2.247378871 | 7.91E−05 | 0.0013143 | solute carrier family 16, member 4 | Plasma Membrane | transporter |
| 3425401B19Rik | −2.245394181 | 7.12E−06 | 0.000169305 | chromosome 10 open reading frame 71 | Other | other |

| Gene | logFC | PValue | FDR | Entrez Gene Name | Location | Type(s) |
|---|---|---|---|---|---|---|
| Lrtm2 | −2.237129762 | 0.000265996 | 0.003635462 | leucine-rich repeats and transmembrane domains 2 | Other | other |
| Sult1a1 | −2.236886147 | 3.44E−06 | 9.05E−05 | sulfotransferase family 1A, phenol-preferring, member 1 | Cytoplasm | enzyme |
| Nrap | −2.225366834 | 3.52E−06 | 9.21E−05 | nebulin-related anchoring protein | Cytoplasm | other |
| Cacna1s | −2.216075785 | 1.08E−05 | 0.000245159 | calcium channel, voltage-dependent, L type, alpha 1S subunit | Plasma Membrane | ion channel |
| Mum1l1 | −2.213497637 | 0.000179172 | 0.002616065 | melanoma associated antigen (mutated) 1-like 1 | Cytoplasm | other |
| Hk3 | −2.213406939 | 2.77E−12 | 4.31E−10 | hexokinase 3 (white cell) | Cytoplasm | kinase |
| Camk2b | −2.209496356 | 6.55E−09 | 3.98E−07 | calcium/calmodulin-dependent protein kinase II beta | Cytoplasm | kinase |
| Lamc3 | −2.208122416 | 5.95E−05 | 0.001026687 | laminin, gamma 3 | Extracellular Space | other |
| Wnt10b | −2.205958028 | 2.75E−06 | 7.53E−05 | wingless-type MMTV integration site family, member 10B | Extracellular Space | other |
| Fam107a | −2.204108844 | 0.000258693 | 0.003553395 | family with sequence similarity 107, member A | Nucleus | other |
| 2310002L09Rik | −2.194169008 | 5.30E−05 | 0.000933799 | RIKEN cDNA 2310002L09 gene | Cytoplasm | other |
| Meis1 | −2.193357038 | 1.42E−08 | 7.72E−07 | Meis homeobox 1 | Nucleus | transcription regulator |
| Trdn | −2.192261248 | 4.81E−06 | 0.000120606 | triadin | Cytoplasm | other |
| Mlip | −2.187237572 | 3.41E−06 | 8.99E−05 | muscular LMNA-interacting protein | Nucleus | other |
| Sh3bgr | −2.183033333 | 0.000248973 | 0.003433665 | SH3-binding domain glutamic acid-rich protein | Cytoplasm | other |
| Prkag3 | −2.181939396 | 0.0001064 | 0.001682844 | protein kinase, AMP-activated, gamma 3 non-catalytic subunit | Cytoplasm | other |
| Cacng1 | −2.168663866 | 1.05E−06 | 3.25E−05 | calcium channel, voltage-dependent, gamma subunit 1 | Plasma Membrane | ion channel |
| Sypl2 | −2.167562914 | 0.000345737 | 0.004491952 | synaptophysin-like 2 | Other | other |
| Hspb1 | −2.159559855 | 4.85E−08 | 2.26E−06 | heat shock 27 kDa protein 1 | Cytoplasm | other |
| Dusp27 | −2.133894504 | 4.49E−09 | 2.91E−07 | dual specificity phosphatase 27 (putative) | Other | phosphatase |
| Notum | −2.119495301 | 6.47E−06 | 0.000156084 | notum pectinacetylesterase homolog (*Drosophila*) | Extracellular Space | other |
| Pdk4 | −2.119339262 | 9.60E−08 | 4.04E−06 | pyruvate dehydrogenase kinase, isozyme 4 | Cytoplasm | kinase |
| Myo18b | −2.119301176 | 1.98E−06 | 5.66E−05 | myosin XVIIIB | Cytoplasm | other |
| Trim72 | −2.115143227 | 1.68E−07 | 6.67E−06 | tripartite motif containing 72, E3 ubiquitin protein ligase | Cytoplasm | enzyme |
| 1500017E21Rik | −2.111456775 | 0.00022252 | 0.003148182 | RIKEN cDNA 1500017E21 gene | Other | other |
| Cnih2 | −2.099012367 | 9.24E−06 | 0.000213856 | cornichon family AMPA receptor auxiliary protein 2 | Extracellular Space | other |
| Mustn1 | −2.092811522 | 1.30E−06 | 3.91E−05 | musculoskeletal, embryonic nuclear protein 1 | Nucleus | other |
| Rbm20 | −2.092417242 | 1.29E−05 | 0.000287162 | RNA binding motif protein 20 | Nucleus | other |
| Casq1 | −2.090786079 | 0.000388851 | 0.004925805 | calsequestrin 1 (fast-twitch, skeletal muscle) | Cytoplasm | other |
| H19 | −2.08747205 | 7.92E−13 | 1.39E−10 | H19, imprinted maternally expressed transcript (non-protein coding) | Cytoplasm | other |

| Gene | logFC | PValue | FDR | Entrez Gene Name | Location | Type(s) |
|---|---|---|---|---|---|---|
| Tlr7 | −2.071501831 | 8.33E−08 | 3.64E−06 | toll-like receptor 7 | Plasma Membrane | transmembrane receptor |
| Kcnc3 | −2.069589796 | 1.37E−06 | 4.09E−05 | potassium channel, voltage gated Shaw related subfamily C, member 3 | Plasma Membrane | ion channel |
| Twist1 | −2.066523744 | 1.16E−16 | 5.49E−14 | twist family bHLH transcription factor 1 | Nucleus | transcription regulator |
| Galnt3 | −2.060068511 | 4.79E−05 | 0.000861365 | polypeptide N-acetylgalactosaminyltransferase 3 | Cytoplasm | enzyme |
| Aldoart2 | −2.056238854 | 0.000286733 | 0.003853432 | aldolase 1 A, retrogene 2 | Other | enzyme |
| Bves | −2.052626225 | 1.58E−05 | 0.00033814 | blood vessel epicardial substance | Plasma Membrane | other |
| Myf6 | −2.041661831 | 0.000242965 | 0.0033727 | myogenic factor 6 (herculin) | Nucleus | transcription regulator |
| Sgms2 | −2.041025291 | 2.31E−05 | 0.000467309 | sphingomyelin synthase 2 | Plasma Membrane | enzyme |
| Mrc1 | −2.038914921 | 2.65E−15 | 1.04E−12 | mannose receptor, C type 1 | Plasma Membrane | transmembrane receptor |
| Slc8a3 | −2.036140803 | 1.48E−06 | 4.37E−05 | solute carrier family 8 (sodium/calcium exchanger), member 3 | Plasma Membrane | transporter |
| Mx1 | −2.032963249 | 4.78E−05 | 0.000859613 | MX dynamin-like GTPase 1 | Nucleus | enzyme |
| Dlx5 | −2.013607351 | 9.59E−05 | 0.00154859 | distal-less homeobox 5 | Nucleus | transcription regulator |
| Cd180 | −1.999988899 | 3.23E−09 | 2.28E−07 | CD180 molecule | Plasma Membrane | other |
| Hspb2 | −1.999144835 | 2.17E−06 | 6.09E−05 | heat shock 27 kDa protein 2 | Cytoplasm | other |
| Penk | −1.992073589 | 5.76E−05 | 0.000997614 | proenkephalin | Extracellular Space | other |
| Phospho1 | −1.974838655 | 3.91E−05 | 0.000737067 | phosphatase, orphan 1 | Extracellular Space | enzyme |
| Colq | −1.971439149 | 2.18E−05 | 0.000441925 | collagen-like tail subunit (single strand of homotrimer) of asymmetric acetylcholinesterase | Extracellular Space | other |
| Myom1 | −1.964431143 | 8.37E−05 | 0.001377131 | myomesin 1 | Cytoplasm | other |
| Eef1a2 | −1.963924398 | 6.39E−06 | 0.00015481 | eukaryotic translation elongation factor 1 alpha 2 | Cytoplasm | translation regulator |
| Ovol1 | −1.96297186 | 3.25E−05 | 0.000631034 | ovo-like zinc finger 1 | Nucleus | transcription regulator |
| Lrrc2 | −1.962718812 | 3.67E−06 | 9.57E−05 | leucine rich repeat containing 2 | Other | other |
| Ccl12 | −1.960416694 | 4.35E−09 | 2.83E−07 | chemokine (C-C motif) ligand 2 | Extracellular Space | cytokine |
| Otud1 | −1.9582093 | 1.43E−08 | 7.74E−07 | OTU deubiquitinase 1 | Other | peptidase |
| Lonrf3 | −1.955839816 | 6.45E−09 | 3.96E−07 | LON peptidase N-terminal domain and ring finger 3 | Other | other |
| Bai1 | −1.955724654 | 0.000100996 | 0.001616059 | #N/A | #N/A | #N/A |
| Hoxc9 | −1.955660858 | 1.01E−12 | 1.72E−10 | homeobox C9 | Nucleus | transcription regulator |
| Arpp21 | −1.945185646 | 0.000233277 | 0.003266598 | cAMP-regulated phosphoprotein, 21 kDa | Cytoplasm | other |
| Obscn | −1.939029162 | 0.000206389 | 0.002959758 | obscurin, cytoskeletal calmodulin and titin-interacting RhoGEF | Cytoplasm | kinase |
| Trem2 | −1.936446063 | 4.42E−08 | 2.09E−06 | triggering receptor expressed on myeloid cells 2 | Plasma Membrane | transmembrane receptor |
| Tpm1 | −1.933315987 | 6.35E−05 | 0.001083589 | tropomyosin 1, alpha | Plasma Membrane | other |
| Mb | −1.927240981 | 4.29E−10 | 3.79E−08 | myoglobin | Cytoplasm | transporter |
| Coro6 | −1.923052355 | 9.30E−05 | 0.001506695 | coronin 6 | Extracellular Space | other |
| Satb2 | −1.922158855 | 0.000113421 | 0.001777453 | SATB homeobox 2 | Nucleus | transcription regulator |
| Dlgap3 | −1.921373713 | 0.00034172 | 0.00444821 | discs, large (Drosophila) homolog-associated protein 3 | Cytoplasm | other |

| Gene | logFC | PValue | FDR | Entrez Gene Name | Location | Type(s) |
| --- | --- | --- | --- | --- | --- | --- |
| Ptn | −1.91531434 | 0.000166962 | 0.002471403 | pleiotrophin | Extracellular Space | growth factor |
| Bmp5 | −1.905399922 | 3.70E−05 | 0.000700196 | bone morphogenetic protein 5 | Extracellular Space | growth factor |
| Ttn | −1.901348241 | 0.000364585 | 0.004670309 | titin | Cytoplasm | kinase |
| Art1 | −1.901283303 | 1.60E−05 | 0.000340711 | ADP-ribosyltransferase 1 | Plasma Membrane | enzyme |
| Sybu | −1.900896598 | 7.80E−06 | 0.000182995 | syntabulin (syntaxin-interacting) | Other | other |
| Tex15 | −1.900378417 | 1.57E−05 | 0.000337967 | testis expressed 15 | Extracellular Space | other |
| Wnt5a | 1.906940595 | 1.25E−07 | 5.19E−06 | wingless-type MMTV integration site family, member 5A | Extracellular Space | cytokine |
| Ero1l | 1.910974733 | 1.72E−11 | 2.18E−09 | endoplasmic reticulum oxidoreductase alpha | Cytoplasm | enzyme |
| Cyp7b1 | 1.913128075 | 6.13E−05 | 0.001053765 | cytochrome P450, family 7, subfamily B, polypeptide 1 | Cytoplasm | enzyme |
| Timp1 | 1.914391071 | 1.11E−09 | 8.91E−08 | TIMP metallopeptidase inhibitor 1 | Extracellular Space | cytokine |
| Bhlhe22 | 1.920077447 | 0.00024332 | 0.0033727 | basic helix-loop-helix family, member e22 | Nucleus | transcription regulator |
| Clca5 | 1.922252646 | 0.000128997 | 0.001980076 | #N/A | #N/A | #N/A |
| Nos2 | 1.93449052 | 9.69E−06 | 0.000223586 | nitric oxide synthase 2, inducible | Cytoplasm | enzyme |
| Sdc1 | 1.934765043 | 1.90E−12 | 3.13E−10 | syndecan 1 | Plasma Membrane | enzyme |
| Ccl11 | 1.935685485 | 1.01E−05 | 0.00023188 | chemokine (C-C motif) ligand 11 | Extracellular Space | cytokine |
| Sfrp2 | 1.937570432 | 0.00010539 | 0.001670733 | secreted frizzled-related protein 2 | Plasma Membrane | transmembrane receptor |
| Adora2b | 1.937719318 | 1.43E−06 | 4.25E−05 | adenosine A2b receptor | Plasma Membrane | G-protein coupled receptor |
| C1rb | 1.948311191 | 6.64E−06 | 0.000159392 | complement component 1, r subcomponent | Extracellular Space | peptidase |
| Cadm3 | 1.954868801 | 1.65E−06 | 4.81E−05 | cell adhesion molecule 3 | Plasma Membrane | other |
| Gcnt4 | 1.959146422 | 5.60E−05 | 0.000974542 | glucosaminyl (N-acetyl) transferase 4, core 2 | Cytoplasm | enzyme |
| AA467197 | 1.95975912 | 0.000134462 | 0.002053093 | chromosome 15 open reading frame 48 | Nucleus | other |
| Adamts5 | 1.96550313 | 1.70E−12 | 2.84E−10 | ADAM metallopeptidase with thrombospondin type 1 motif, 5 | Extracellular Space | peptidase |
| Il6 | 1.96970782 | 3.32E−05 | 0.000642426 | interleukin 6 | Extracellular Space | cytokine |
| Acp5 | 1.97208448 | 1.73E−05 | 0.000365845 | acid phosphatase 5, tartrate resistant | Cytoplasm | phosphatase |
| Plac8 | 1.972654229 | 1.03E−06 | 3.18E−05 | placenta-specific 8 | Nucleus | other |
| Hic1 | 1.977666371 | 2.86E−10 | 2.64E−08 | hypermethylated in cancer 1 | Nucleus | transcription regulator |
| Il18rap | 1.988047069 | 1.49E−05 | 0.000324778 | interleukin 18 receptor accessory protein | Plasma Membrane | transmembrane receptor |
| Prss46 | 2.005016082 | 0.000152543 | 0.002288306 | protease, serine, 46 | Other | peptidase |
| Csgalnact1 | 2.006832892 | 2.07E−12 | 3.33E−10 | chondroitin sulfate N-acetylgalactosaminyltransferase 1 | Cytoplasm | enzyme |
| Phlda2 | 2.012095452 | 0.000118738 | 0.001848071 | pleckstrin homology-like domain, family A, member 2 | Cytoplasm | other |
| Barx2 | 2.013964382 | 1.83E−06 | 5.25E−05 | BARX homeobox 2 | Nucleus | transcription regulator |
| Kctd11 | 2.020123243 | 8.08E−12 | 1.11E−09 | potassium channel tetramerization domain containing 11 | Cytoplasm | other |
| Hilpda | 2.022779424 | 7.35E−08 | 3.30E−06 | hypoxia inducible lipid droplet-associated | Cytoplasm | other |
| Klhdc8a | 2.029163571 | 7.64E−06 | 0.000180115 | kelch domain containing 8A | Other | other |
| Crabp2 | 2.041000695 | 3.54E−05 | 0.000676149 | cellular retinoic acid binding protein 2 | Cytoplasm | transporter |

-continued

| Gene | logFC | PValue | FDR | Entrez Gene Name | Location | Type(s) |
|---|---|---|---|---|---|---|
| Medag | 2.044971831 | 1.99E−12 | 3.24E−10 | mesenteric estrogen-dependent adipogenesis | Cytoplasm | other |
| Napsa | 2.050808167 | 6.69E−08 | 3.03E−06 | napsin A aspartic peptidase | Extracellular Space | peptidase |
| Col23a1 | 2.074615476 | 6.01E−09 | 3.72E−07 | collagen, type XXIII, alpha 1 | Plasma Membrane | other |
| Wnt2b | 2.077564459 | 1.78E−05 | 0.000373778 | wingless-type MMTV integration site family, member 2B | Extracellular Space | other |
| Lgi3 | 2.083185898 | 0.000201013 | 0.002897856 | leucine-rich repeat LGI family, member 3 | Extracellular Space | other |
| Il33 | 2.084646455 | 5.04E−11 | 5.30E−09 | interleukin 33 | Extracellular Space | cytokine |
| H2-Ab1 | 2.087468297 | 1.75E−09 | 1.30E−07 | major histocompatibility complex, class II, DQ beta 1 | Plasma Membrane | other |
| 4930502E18Rik | 2.087590606 | 5.50E−05 | 0.000961458 | RIKEN cDNA 4930502E18 gene | Other | other |
| Osr1 | 2.114093041 | 1.84E−08 | 9.56E−07 | odd-skipped related transcription factor 1 | Nucleus | other |
| Serping1 | 2.116258617 | 1.60E−13 | 3.43E−11 | serpin peptidase inhibitor, clade G (C1 inhibitor), member 1 | Extracellular Space | other |
| P2ry10 | 2.117660014 | 6.16E−05 | 0.001055499 | purinergic receptor P2Y, G-protein coupled, 10 | Plasma Membrane | G-protein coupled receptor |
| Ddit4 | 2.120727355 | 1.04E−15 | 4.32E−13 | DNA-damage-inducible transcript 4 | Cytoplasm | other |
| Tmeff2 | 2.123849758 | 0.000286592 | 0.003853432 | transmembrane protein with EGF-like and two follistatin-like domains 2 | Cytoplasm | other |
| Pthlh | 2.12599575 | 3.81E−05 | 0.000719195 | parathyroid hormone-like hormone | Extracellular Space | other |
| Pla1a | 2.128297502 | 3.15E−12 | 4.77E−10 | phospholipase A1 member A | Extracellular Space | enzyme |
| Cwc22 | 2.131128484 | 0.000289077 | 0.003873516 | CWC22 spliceosome-associated protein | Nucleus | other |
| Adamts4 | 2.131910626 | 9.89E−12 | 1.30E−09 | ADAM metallopeptidase with thrombospondin type 1 motif, 4 | Extracellular Space | peptidase |
| Ocstamp | 2.133707622 | 0.000285909 | 0.003849919 | osteoclast stimulatory transmembrane protein | Other | other |
| Avpr1a | 2.135058799 | 3.05E−08 | 1.49E−06 | arginine vasopressin receptor 1A | Plasma Membrane | G-protein coupled receptor |
| Sphk1 | 2.137577627 | 5.04E−10 | 4.42E−08 | sphingosine kinase 1 | Cytoplasm | kinase |
| Alox12 | 2.147703459 | 7.02E−05 | 0.001179092 | arachidonate 12-lipoxygenase | Cytoplasm | enzyme |
| Cd74 | 2.154265386 | 8.23E−10 | 6.87E−08 | CD74 molecule, major histocompatibility complex, class II invariant chain | Plasma Membrane | transmembrane receptor |
| Ier3 | 2.156413161 | 6.99E−10 | 5.94E−08 | immediate early response 3 | Cytoplasm | other |
| Niacr1 | 2.161017459 | 4.17E−06 | 0.000107108 | #N/A | #N/A | #N/A |
| Galnt16 | 2.163332213 | 1.33E−11 | 1.70E−09 | polypeptide N-acetylgalactosaminyltransferase 16 | Cytoplasm | enzyme |
| Fam83f | 2.163464457 | 9.66E−05 | 0.001557314 | family with sequence similarity 83, member F | Other | other |
| Phyhipl | 2.166920709 | 0.000352603 | 0.004552696 | phytanoyl-CoA 2-hydroxylase interacting protein-like | Cytoplasm | other |
| H2-Aa | 2.16974298 | 3.79E−09 | 2.53E−07 | major histocompatibility complex, class II, DQ alpha 1 | Plasma Membrane | transmembrane receptor |
| Il1rl1 | 2.175512643 | 4.51E−06 | 0.000114652 | interleukin 1 receptor-like 1 | Plasma Membrane | transmembrane receptor |
| Dpt | 2.180012546 | 2.29E−13 | 4.74E−11 | dermatopontin | Extracellular Space | other |

-continued

| Gene | logFC | PValue | FDR | Entrez Gene Name | Location | Type(s) |
|---|---|---|---|---|---|---|
| Kcnj15 | 2.180673205 | 1.37E−08 | 7.48E−07 | potassium channel, inwardly rectifying subfamily J, member 15 | Plasma Membrane | ion channel |
| Rnd1 | 2.181967661 | 9.57E−09 | 5.64E−07 | Rho family GTPase 1 | Cytoplasm | enzyme |
| Gpr114 | 2.189646297 | 1.94E−07 | 7.41E−06 | #N/A | #N/A | #N/A |
| Ccbp2 | 2.193904635 | 2.20E−07 | 8.27E−06 | #N/A | #N/A | #N/A |
| Elfn1 | 2.199467366 | 4.19E−05 | 0.000776232 | extracellular leucine-rich repeat and fibronectin type III domain containing 1 | Plasma Membrane | other |
| Cxadr | 2.20082858 | 0.000332993 | 0.004351168 | coxsackie virus and adenovirus receptor | Plasma Membrane | transmembrane receptor |
| Mcpt4 | 2.206254485 | 0.000169343 | 0.002496531 | mast cell protease 4 | Other | peptidase |
| Stac2 | 2.212366039 | 9.24E−09 | 5.50E−07 | SH3 and cysteine rich domain 2 | Other | other |
| Cxcr7 | 2.216406879 | 4.59E−14 | 1.16E−11 | #N/A | #N/A | #N/A |
| Foxd1 | 2.217141687 | 2.09E−05 | 0.000427216 | forkhead box D1 | Nucleus | transcription regulator |
| Cd209f | 2.232430603 | 0.000140148 | 0.002118637 | CD209f antigen | Other | other |
| Crabp1 | 2.235053806 | 0.000377869 | 0.004813427 | cellular retinoic acid binding protein 1 | Cytoplasm | transporter |
| Rtn4rl2 | 2.236586861 | 9.06E−08 | 3.91E−06 | reticulon 4 receptor-like 2 | Plasma Membrane | other |
| Slc39a14 | 2.238458836 | 2.66E−14 | 7.14E−12 | solute carrier family 39 (zinc transporter), member 14 | Plasma Membrane | transporter |
| Ifnlr1 | 2.242774024 | 1.94E−05 | 0.000403681 | interferon, lambda receptor 1 | Plasma Membrane | transmembrane receptor |
| 5730416F02Rik | 2.253801229 | 5.43E−06 | 0.00013307 | capping protein (actin filament), gelsolin-like pseudogene | Other | other |
| Trpm6 | 2.25769376 | 2.03E−07 | 7.73E−06 | transient receptor potential cation channel, subfamily M, member 6 | Plasma Membrane | kinase |
| Gfra1 | 2.258361982 | 1.82E−06 | 5.23E−05 | GDNF family receptor alpha 1 | Plasma Membrane | transmembrane receptor |
| Egln3 | 2.26022722 | 4.82E−15 | 1.69E−12 | egl-9 family hypoxia-inducible factor 3 | Cytoplasm | enzyme |
| S100a9 | 2.261077077 | 0.000236631 | 0.003306796 | S100 calcium binding protein A9 | Cytoplasm | other |
| Fbln2 | 2.261656935 | 3.57E−10 | 3.21E−08 | fibulin 2 | Extracellular Space | other |
| Tnfsf11 | 2.262220766 | 0.000168565 | 0.002489291 | tumor necrosis factor (ligand) superfamily, member 11 | Extracellular Space | cytokine |
| S1pr3 | 2.26806489 | 8.22E−08 | 3.62E−06 | sphingosine-1-phosphate receptor 3 | Plasma Membrane | G-protein coupled receptor |
| Acsbg1 | 2.27206321 | 2.08E−05 | 0.000425956 | acyl-CoA synthetase bubblegum family member 1 | Cytoplasm | enzyme |
| Kcne3 | 2.28228483 | 7.11E−11 | 7.32E−09 | potassium channel, voltage gated subfamily E regulatory beta subunit 3 | Plasma Membrane | ion channel |
| Lmx1a | 2.286295067 | 8.74E−05 | 0.001429283 | LIM homeobox transcription factor 1, alpha | Nucleus | transcription regulator |
| Sfrp1 | 2.286645932 | 0.000382833 | 0.004863077 | secreted frizzled-related protein 1 | Plasma Membrane | transmembrane receptor |
| Aqp2 | 2.294873359 | 3.68E−05 | 0.000699026 | aquaporin 2 (collecting duct) | Plasma Membrane | transporter |
| 1810033B17Rik | 2.303750907 | 1.76E−05 | 0.000371982 | #N/A | #N/A | #N/A |
| Tmem178 | 2.30838751 | 8.85E−06 | 0.000205126 | transmembrane protein 178A | Other | other |
| Figf | 2.324615912 | 3.70E−09 | 2.48E−07 | c-fos induced growth factor (vascular endothelial growth factor D) | Extracellular Space | growth factor |
| Slc6a2 | 2.327386448 | 5.24E−05 | 0.000926129 | solute carrier family 6 (neurotransmitter transporter), member 2 | Plasma Membrane | transporter |

-continued

| Gene | logFC | PValue | FDR | Entrez Gene Name | Location | Type(s) |
|---|---|---|---|---|---|---|
| Gpr123 | 2.333408054 | 2.32E-07 | 8.66E-06 | #N/A | #N/A | #N/A |
| Ces2g | 2.337823509 | 2.07E-05 | 0.000424294 | carboxylesterase 2G | Other | enzyme |
| Treml4 | 2.356184647 | 7.19E-05 | 0.00120497 | triggering receptor expressed on myeloid cells-like 4 | Other | other |
| Doc2b | 2.356263534 | 0.000143893 | 0.002170448 | double C2-like domains, beta | Cytoplasm | transporter |
| Lbp | 2.35803444 | 5.08E-13 | 9.65E-11 | lipopolysaccharide binding protein | Plasma Membrane | transporter |
| Ifi205 | 2.360747496 | 5.29E-14 | 1.32E-11 | interferon, gamma-inducible protein 16 | Nucleus | transcription regulator |
| Rgs9 | 2.360817111 | 6.48E-05 | 0.001101485 | regulator of G-protein signaling 9 | Cytoplasm | enzyme |
| Arsi | 2.371268625 | 2.16E-08 | 1.09E-06 | arylsulfatase family, member I | Extracellular Space | enzyme |
| Ciita | 2.373772401 | 6.36E-07 | 2.08E-05 | class II, major histocompatibility complex, transactivator | Nucleus | transcription regulator |
| Dusp4 | 2.379388346 | 2.36E-06 | 6.57E-05 | dual specificity phosphatase 4 | Nucleus | phosphatase |
| Rorb | 2.38089784 | 0.000295309 | 0.003937748 | RAR-related orphan receptor B | Nucleus | ligand-dependent nuclear receptor |
| Sbsn | 2.383926086 | 1.80E-05 | 0.000377684 | suprabasin | Cytoplasm | other |
| Cdh1 | 2.392769181 | 3.51E-08 | 1.69E-06 | cadherin 1, type 1 | Plasma Membrane | other |
| Fgr | 2.395997722 | 1.73E-17 | 9.84E-15 | FGR proto-oncogene, Src family tyrosine kinase | Nucleus | kinase |
| Kcnip1 | 2.401474217 | 1.95E-05 | 0.000405805 | Kv channel interacting protein 1 | Plasma Membrane | ion channel |
| Ak4 | 2.401846699 | 5.33E-08 | 2.46E-06 | adenylate kinase 4 | Cytoplasm | kinase |
| A630023A22Rik | 2.414937431 | 7.63E-05 | 0.001272883 | RIKEN cDNA A630023A22 gene | Other | other |
| Has1 | 2.417424502 | 1.62E-08 | 8.57E-07 | hyaluronan synthase 1 | Plasma Membrane | enzyme |
| Sdk1 | 2.424720594 | 1.24E-08 | 6.91E-07 | sidekick cell adhesion molecule 1 | Plasma Membrane | other |
| Gjb5 | 2.429127176 | 6.04E-06 | 0.000146855 | gap junction protein, beta 5, 31.1 kDa | Plasma Membrane | transporter |
| 5730559C18Rik | 2.434932765 | 5.17E-05 | 0.000919826 | chromosome 1 open reading frame 106 | Other | other |
| Adm | 2.437796473 | 3.10E-09 | 2.21E-07 | adrenomedullin | Extracellular Space | other |
| Hmga2 | 2.445141593 | 1.35E-05 | 0.000297813 | high mobility group AT-hook 2 | Nucleus | enzyme |
| Itgax | 2.449058631 | 3.26E-16 | 1.49E-13 | integrin, alpha X (complement component 3 receptor 4 subunit) | Plasma Membrane | transmembrane receptor |
| Itln1 | 2.454578666 | 3.52E-07 | 1.24E-05 | intelectin 1 (galactofuranose binding) | Plasma Membrane | other |
| Ifitm1 | 2.454902535 | 1.49E-13 | 3.24E-11 | interferon induced transmembrane protein 1 | Other | other |
| Sh2d5 | 2.457966113 | 5.17E-13 | 9.68E-11 | SH2 domain containing 5 | Plasma Membrane | other |
| Ndufa4l2 | 2.461273301 | 4.04E-12 | 5.88E-10 | NADH dehydrogenase (ubiquinone) 1 alpha subcomplex, 4-like 2 | Other | enzyme |
| Ffar2 | 2.472209214 | 0.000226332 | 0.003185641 | free fatty acid receptor 2 | Plasma Membrane | G-protein coupled receptor |
| Scd1 | 2.488851454 | 3.66E-07 | 1.28E-05 | stearoyl-CoA desaturase (delta-9-desaturase) | Cytoplasm | enzyme |
| Mmp9 | 2.499142569 | 4.69E-05 | 0.000845283 | matrix metallopeptidase 9 | Extracellular Space | peptidase |
| Cxcl1 | 2.51537654 | 3.67E-05 | 0.000696707 | chemokine (C—X—C motif) ligand 2 | Extracellular Space | cytokine |
| Nrn1 | 2.520515557 | 2.96E-06 | 8.01E-05 | neuritin 1 | Cytoplasm | other |
| Inhbb | 2.523010814 | 5.62E-13 | 1.04E-10 | inhibin, beta B | Extracellular Space | growth factor |
| Col28a1 | 2.531182459 | 9.55E-07 | 2.97E-05 | collagen, type XXVIII, alpha 1 | Extracellular Space | other |

| Gene | logFC | PValue | FDR | Entrez Gene Name | Location | Type(s) |
|---|---|---|---|---|---|---|
| Dnmt3l | 2.532511137 | 0.000269506 | 0.003668764 | DNA (cytosine-5-)-methyltransferase 3-like | Nucleus | transcription regulator |
| Fcrla | 2.535289213 | 0.000140017 | 0.002118637 | Fc receptor-like A | Plasma Membrane | other |
| Cxcl14 | 2.538668396 | 1.33E−09 | 1.04E−07 | chemokine (C—X—C motif) ligand 14 | Extracellular Space | cytokine |
| Pi16 | 2.545417685 | 9.68E−08 | 4.06E−06 | peptidase inhibitor 16 | Extracellular Space | other |
| C4b | 2.554327389 | 3.52E−09 | 2.42E−07 | complement component 4B (Chido blood group) | Extracellular Space | other |
| Gzmc | 2.586719596 | 2.23E−06 | 6.24E−05 | granzyme C | Cytoplasm | peptidase |
| Car9 | 2.588221576 | 5.94E−09 | 3.70E−07 | carbonic anhydrase IX | Nucleus | enzyme |
| H2-Eb1 | 2.589361992 | 4.28E−11 | 4.72E−09 | major histocompatibility complex, class II, DR beta 5 | Plasma Membrane | transmembrane receptor |
| Cpa3 | 2.592224708 | 0.000349947 | 0.004527105 | carboxypeptidase A3 (mast cell) | Extracellular Space | peptidase |
| Rhov | 2.597158136 | 3.97E−05 | 0.000744269 | ras homolog family member V | Plasma Membrane | enzyme |
| Smoc1 | 2.609276659 | 1.13E−17 | 7.01E−15 | SPARC related modular calcium binding 1 | Extracellular Space | other |
| Cd244 | 2.610625963 | 2.48E−09 | 1.82E−07 | CD244 molecule, natural killer cell receptor 2B4 | Plasma Membrane | transmembrane receptor |
| Serpina3h | 2.626086546 | 9.48E−16 | 4.05E−13 | serine (or cysteine) peptidase inhibitor, clade A, member 3H | Extracellular Space | other |
| Dpp6 | 2.627269895 | 3.28E−06 | 8.69E−05 | dipeptidyl-peptidase 6 | Plasma Membrane | other |
| Tmem95 | 2.630604846 | 3.26E−06 | 8.64E−05 | transmembrane protein 95 | Other | other |
| Rgs16 | 2.641503944 | 7.07E−14 | 1.61E−11 | regulator of G-protein signaling 16 | Cytoplasm | other |
| Mmp12 | 2.661387138 | 8.47E−12 | 1.14E−09 | matrix metallopeptidase 12 | Extracellular Space | peptidase |
| Ttyh1 | 2.666310269 | 1.17E−08 | 6.67E−07 | tweety family member 1 | Plasma Membrane | ion channel |
| Tmem125 | 2.684592738 | 0.00020899 | 0.002984538 | transmembrane protein 125 | Other | other |
| Pcsk5 | 2.688181091 | 2.88E−12 | 4.42E−10 | proprotein convertase subtilisin/kexin type 5 | Extracellular Space | peptidase |
| Slc2a1 | 2.701076956 | 2.95E−13 | 5.94E−11 | solute carrier family 2 (facilitated glucose transporter), member 1 | Plasma Membrane | transporter |
| Frmd5 | 2.704255771 | 7.70E−05 | 0.001282835 | FERM domain containing 5 | Other | other |
| Col5a3 | 2.706994884 | 9.13E−22 | 9.61E−19 | collagen, type V, alpha 3 | Extracellular Space | other |
| Dmkn | 2.711140688 | 0.00034439 | 0.004478701 | dermokine | Extracellular Space | other |
| Lrrc15 | 2.71712803 | 3.40E−12 | 5.06E−10 | leucine rich repeat containing 15 | Plasma Membrane | other |
| C3 | 2.726900819 | 2.87E−10 | 2.64E−08 | complement component 3 | Extracellular Space | peptidase |
| Nt5e | 2.732947213 | 7.62E−12 | 1.05E−09 | 5'-nucleotidase, ecto (CD73) | Plasma Membrane | phosphatase |
| Serpind1 | 2.762623986 | 9.29E−07 | 2.91E−05 | serpin peptidase inhibitor, clade D (heparin cofactor), member 1 | Extracellular Space | other |
| Unc13a | 2.772685031 | 1.69E−09 | 1.27E−07 | unc-13 homolog A (C. elegans) | Plasma Membrane | other |
| Tpsb2 | 2.780651006 | 8.40E−08 | 3.65E−06 | tryptase alpha/beta 1 | Extracellular Space | peptidase |
| Inhba | 2.795338332 | 3.18E−08 | 1.54E−06 | inhibin, beta A | Extracellular Space | growth factor |
| C4a | 2.798731104 | 2.61E−10 | 2.44E−08 | complement component 4B (Chido blood group) | Extracellular Space | other |
| Slc2a3 | 2.810697868 | 2.17E−13 | 4.56E−11 | solute carrier family 2 (facilitated glucose transporter), member 3 | Plasma Membrane | transporter |

| Gene | logFC | PValue | FDR | Entrez Gene Name | Location | Type(s) |
|---|---|---|---|---|---|---|
| Wt1 | 2.82046663 | 0.000169678 | 0.002498782 | Wilms tumor 1 | Nucleus | transcription regulator |
| 1300002K09Rik | 2.834274508 | 7.10E−07 | 2.29E−05 | #N/A | #N/A | #N/A |
| Vat1l | 2.842318796 | 6.74E−05 | 0.001138678 | vesicle amine transport 1-like | Other | enzyme |
| Il1b | 2.842564699 | 3.03E−24 | 3.76E−21 | interleukin 1, beta | Extracellular Space | cytokine |
| Gjb3 | 2.850664786 | 2.13E−06 | 6.01E−05 | gap junction protein, beta 3, 31 kDa | Plasma Membrane | transporter |
| Sfrp4 | 2.873431041 | 5.56E−14 | 1.35E−11 | secreted frizzled-related protein 4 | Plasma Membrane | transmembrane receptor |
| Osbp2 | 2.894267579 | 8.23E−11 | 8.28E−09 | oxysterol binding protein 2 | Cytoplasm | other |
| Serpina3i | 2.896733041 | 3.59E−11 | 4.13E−09 | serine (or cysteine) peptidase inhibitor, clade A, member 3G | Other | other |
| Ccbe1 | 2.899591596 | 1.80E−14 | 5.13E−12 | collagen and calcium binding EGF domains 1 | Extracellular Space | other |
| Dnase1l3 | 2.914095612 | 4.71E−11 | 5.03E−09 | deoxyribonuclease I-like 3 | Nucleus | enzyme |
| Prg4 | 2.920652095 | 1.48E−13 | 3.24E−11 | proteoglycan 4 (megakaryocyte stimulating factor, articular superficial zone protein) | Extracellular Space | other |
| Serpine1 | 2.943112329 | 2.65E−13 | 5.41E−11 | serpin peptidase inhibitor, clade E (nexin, plasminogen activator inhibitor type 1), member 1 | Extracellular Space | other |
| Nfasc | 2.955386081 | 4.40E−11 | 4.81E−09 | neurofascin | Plasma Membrane | other |
| Tnfsf8 | 2.958098025 | 7.42E−08 | 3.31E−06 | tumor necrosis factor (ligand) superfamily, member 8 | Plasma Membrane | cytokine |
| Adra2a | 2.963089237 | 3.96E−36 | 1.36E−32 | adrenoceptor alpha 2A | Plasma Membrane | G-protein coupled receptor |
| Syt5 | 2.967862699 | 1.03E−09 | 8.32E−08 | synaptotagmin V | Cytoplasm | transporter |
| Erv3 | 2.976253995 | 1.57E−05 | 0.000337967 | endogenous retroviral sequence 3 | Other | other |
| Lgi2 | 2.980280668 | 7.82E−07 | 2.49E−05 | leucine-rich repeat LGI family, member 2 | Extracellular Space | other |
| Adcy5 | 2.989745548 | 1.35E−15 | 5.42E−13 | adenylate cyclase 5 | Plasma Membrane | enzyme |
| Lcn2 | 3.00569291 | 4.88E−09 | 3.09E−07 | lipocalin 2 | Extracellular Space | transporter |
| Syt17 | 3.012074261 | 1.31E−06 | 3.93E−05 | synaptotagmin XVII | Plasma Membrane | other |
| Efemp1 | 3.013217113 | 2.56E−07 | 9.39E−06 | EGF containing fibulin-like extracellular matrix protein 1 | Extracellular Space | enzyme |
| Fam5c | 3.02276903 | 1.82E−07 | 7.05E−06 | #N/A | #N/A | #N/A |
| Sorcs1 | 3.045355688 | 1.60E−05 | 0.000340968 | sortilin-related VPS10 domain containing receptor 1 | Plasma Membrane | transporter |
| Adamts15 | 3.054035878 | 7.61E−15 | 2.54E−12 | ADAM metallopeptidase with thrombospondin type 1 motif, 15 | Extracellular Space | peptidase |
| Clec2e | 3.07635781 | 6.84E−06 | 0.000163535 | C-type lectin domain family 2, member h | Plasma Membrane | transmembrane receptor |
| Chl1 | 3.084606232 | 5.81E−07 | 1.92E−05 | cell adhesion molecule L1-like | Plasma Membrane | other |
| Mmrn1 | 3.110168932 | 0.000104343 | 0.001656047 | multimerin 1 | Extracellular Space | other |
| Gpr35 | 3.118726492 | 3.52E−19 | 2.84E−16 | G protein-coupled receptor 35 | Plasma Membrane | G-protein coupled receptor |
| Rarres2 | 3.147276259 | 1.10E−09 | 8.87E−08 | retinoic acid receptor responder (tazarotene induced) 2 | Plasma Membrane | transmembrane receptor |
| Pgf | 3.150550679 | 8.07E−17 | 4.09E−14 | placental growth factor | Extracellular Space | growth factor |
| Serpina3f | 3.155375641 | 5.61E−14 | 1.35E−11 | serine (or cysteine) peptidase inhibitor, clade A, member 3G | Other | other |

-continued

| Gene | logFC | PValue | FDR | Entrez Gene Name | Location | Type(s) |
|---|---|---|---|---|---|---|
| Il1r2 | 3.155818097 | 9.76E−15 | 3.11E−12 | interleukin 1 receptor, type II | Plasma Membrane | transmembrane receptor |
| Il13ra2 | 3.208712372 | 4.27E−05 | 0.000786196 | interleukin 13 receptor, alpha 2 | Plasma Membrane | transmembrane receptor |
| Nxph4 | 3.212429551 | 1.20E−08 | 6.76E−07 | neurexophilin 4 | Extracellular Space | other |
| Slit1 | 3.221521866 | 8.08E−08 | 3.56E−06 | slit guidance ligand 1 | Extracellular Space | other |
| Col10a1 | 3.255299689 | 8.78E−08 | 3.80E−06 | collagen, type X, alpha 1 | Extracellular Space | other |
| Grem1 | 3.306998841 | 4.81E−09 | 3.07E−07 | gremlin 1, DAN family BMP antagonist | Extracellular Space | other |
| Rpl21 | 3.319158494 | 0.000321595 | 0.004226455 | ribosomal protein L21 | Cytoplasm | other |
| Ly6k | 3.330210263 | 1.32E−05 | 0.000292565 | lymphocyte antigen 6 complex, locus K | Nucleus | other |
| Pcsk9 | 3.343662872 | 1.11E−05 | 0.000249753 | proprotein convertase subtilisin/kexin type 9 | Extracellular Space | peptidase |
| Dbx2 | 3.374124712 | 8.16E−10 | 6.85E−08 | developing brain homeobox 2 | Nucleus | transcription regulator |
| B3galt5 | 3.42887914 | 3.17E−06 | 8.47E−05 | UDP-Gal:betaGlcNAc beta 1,3-galactosyltransferase, polypeptide 5 | Cytoplasm | enzyme |
| Il11 | 3.446479515 | 1.36E−08 | 7.48E−07 | interleukin 11 | Extracellular Space | cytokine |
| Htr1b | 3.47009247 | 2.52E−14 | 6.90E−12 | 5-hydroxytryptamine (serotonin) receptor 1B, G protein-coupled | Plasma Membrane | G-protein coupled receptor |
| Cxcl13 | 3.554799387 | 3.92E−05 | 0.000737235 | chemokine (C—X—C motif) ligand 13 | Extracellular Space | cytokine |
| 9330182L06Rik | 3.599154487 | 3.76E−06 | 9.79E−05 | KIAA1324-like | Other | other |
| Cd207 | 3.698500979 | 6.80E−11 | 7.05E−09 | CD207 molecule, langerin | Plasma Membrane | other |
| Serpina3n | 3.699329372 | 1.12E−13 | 2.51E−11 | serpin peptidase inhibitor, clade A (alpha-1 antiproteinase, antitrypsin), member 3 | Extracellular Space | other |
| Tmem132e | 3.706736426 | 9.24E−08 | 3.94E−06 | transmembrane protein 132E | Other | other |
| Serpina3m | 3.722226604 | 5.48E−18 | 3.57E−15 | serpin peptidase inhibitor, clade A (alpha-1 antiproteinase, antitrypsin), member 3 | Extracellular Space | other |
| Kcnmb1 | 3.771552594 | 2.30E−08 | 1.15E−06 | potassium channel subfamily M regulatory beta subunit 1 | Plasma Membrane | ion channel |
| Gpr141 | 3.898353543 | 1.01E−10 | 9.98E−09 | G protein-coupled receptor 141 | Plasma Membrane | G-protein coupled receptor |
| Arg1 | 3.924911517 | 2.76E−08 | 1.37E−06 | arginase 1 | Cytoplasm | enzyme |
| Tpsab1 | 3.958781996 | 9.04E−15 | 2.94E−12 | tryptase alpha/beta 1 | Nucleus | peptidase |
| Ereg | 3.993604416 | 9.00E−07 | 2.82E−05 | epiregulin | Extracellular Space | growth factor |
| Mmp13 | 4.025132705 | 3.95E−15 | 1.42E−12 | matrix metallopeptidase 13 | Extracellular Space | peptidase |
| Tnfrsf9 | 4.100043244 | 1.10E−24 | 1.67E−21 | tumor necrosis factor receptor superfamily, member 9 | Plasma Membrane | transmembrane receptor |
| Slc7a11 | 4.123064166 | 1.29E−17 | 7.68E−15 | solute carrier family 7 (anionic amino acid transporter light chain, xc-system), member 11 | Plasma Membrane | transporter |
| Akr1c18 | 4.133960273 | 1.07E−11 | 1.40E−09 | aldo-keto reductase family 1, member C3 | Cytoplasm | enzyme |
| Mgarp | 4.215853911 | 3.91E−11 | 4.38E−09 | mitochondria-localized glutamic acid-rich protein | Cytoplasm | other |
| Serpina3k | 4.258478095 | 6.90E−13 | 1.26E−10 | serpin peptidase inhibitor, clade A (alpha-1 antiproteinase, antitrypsin), member 3 | Extracellular Space | other |
| Ccl20 | 4.325657841 | 1.88E−10 | 1.80E−08 | chemokine (C-C motif) ligand 20 | Extracellular Space | cytokine |

-continued

| Gene | logFC | PValue | FDR | Entrez Gene Name | Location | Type(s) |
|---|---|---|---|---|---|---|
| Cfi | 4.589933583 | 1.17E−09 | 9.20E−08 | complement factor I | Extracellular Space | peptidase |
| Reg3g | 4.66412117 | 1.46E−12 | 2.47E−10 | regenerating islet-derived 3 gamma | Extracellular Space | other |
| Krt19 | 4.779241895 | 1.21E−05 | 0.000271903 | keratin 19, type I | Cytoplasm | other |
| Ptprn | 4.824685996 | 6.13E−22 | 6.98E−19 | protein tyrosine phosphatase, receptor type, N | Plasma Membrane | phosphatase |
| A2m | 4.936644365 | 1.29E−07 | 5.33E−06 | alpha-2-macroglobulin | Extracellular Space | transporter |
| Saa3 | 4.938190554 | 6.34E−08 | 2.88E−06 | serum amyloid A 3 | Extracellular Space | other |
| Gzme | 5.281856145 | 6.57E−14 | 1.52E−11 | granzyme H (cathepsin G-like 2, protein h-CCPX) | Cytoplasm | peptidase |
| Mmp3 | 5.447660714 | 4.84E−28 | 8.28E−25 | matrix metallopeptidase 3 | Extracellular Space | peptidase |
| Prokr2 | 5.903313554 | 2.25E−14 | 6.29E−12 | prokineticin receptor 2 | Plasma Membrane | G-protein coupled receptor |
| Fgf23 | 6.223273913 | 4.42E−14 | 1.14E−11 | fibroblast growth factor 23 | Extracellular Space | growth factor |
| Mcpt2 | 6.857304981 | 4.93E−30 | 1.12E−26 | mast cell protease 2 | Extracellular Space | peptidase |
| Gzmd | 7.248393542 | 7.17E−13 | 1.29E−10 | granzyme H (cathepsin G-like 2, protein h-CCPX) | Cytoplasm | peptidase |
| Cldn10 | 7.636808366 | 5.34E−09 | 3.35E−07 | claudin 10 | Plasma Membrane | other |
| Mmp10 | 7.64543229 | 2.07E−24 | 2.84E−21 | matrix metallopeptidase 10 | Extracellular Space | peptidase |
| Gm9992 | 7.648664919 | 4.61E−08 | 2.16E−06 | unc-93 homolog A (*C. elegans*) | Plasma Membrane | other |
| Mcpt8 | 8.11716942 | 5.31E−12 | 7.57E−10 | mast cell protease 8 | Cytoplasm | other |
| Reg1 | 10.74685846 | 8.53E−19 | 6.49E−16 | regenerating islet-derived 1 alpha | Extracellular Space | growth factor |
| Mcpt1 | 11.25382227 | 2.86E−47 | 3.92E−43 | mast cell protease 1 | Other | peptidase |

Various aspects of the disclosure have been described. These and other aspects are within the scope of the following claims.

What is claimed is:

1. A method comprising:
   xenografting tissue from a donor organism of a second species on to a host organism of a first species;
   obtaining a plurality of exosomes from a sample of bodily fluid derived from the host organism, wherein the plurality of exosomes comprises a plurality of molecules of messenger ribonucleic acid (mRNA);
   identifying, for substantially each molecule of the plurality of molecules of mRNA, a corresponding RNA sequence;
   generating a combined dataset of RNA sequence reads by aligning each RNA sequence to a combined reference genome, wherein aligning each RNA sequence to the combined reference genome includes comparing a genomic location of each corresponding RNA sequence with a genomic location of a gene sequence of the combined reference genome, wherein the combined reference genome includes gene sequences from at least a portion of a first genome derived from the first species and at least a portion of a second genome derived from the second species, wherein the combined reference genome indicates an origin species of each corresponding gene sequence, and wherein the combined dataset of RNA sequence reads includes RNA sequence reads from both the first species and the second species;
   filtering non-unique RNA sequence reads from the combined dataset by identifying species-specific RNA sequences exclusive to either the first species or the second species, wherein identifying species-specific RNA sequences includes determining, for each corresponding RNA sequence, whether the RNA sequence is substantially aligned with exactly one corresponding gene sequence of the combined reference genome;
   differentiating an origin species of each species-specific RNA sequence in the filtered combined dataset by determining whether the corresponding RNA sequence is aligned to a gene sequence of the combined reference genome associated with the first genome of the first species or the second genome of the second species;
   quantifying an abundance level of each species-specific RNA sequence in the sample by determining an approximate number of times that each species-specific RNA sequence occurs in the filtered combined dataset; and
   determining, based on the abundance level of species-specific RNA sequences associated with at least one of the first species or the second species in the sample of bodily fluid either increasing over a period of time or exceeding a predetermined threshold, that the tissue derived from the donor organism contains a biomarker indicative of at least one of:
   a disease status,
   a response of the host organism to the tissue derived from the donor organism, or
   a response of the tissue derived from the donor organism to transplantation within the host organism.

2. The method of claim 1, wherein the one or more gene sequences comprises at least one of one or more coding sequences or one or more regulatory sequences.

3. The method of claim 1, further comprising determining one or more characteristics of each species-specific RNA sequence, wherein the one or more characteristics include a gene name of the corresponding gene sequence.

4. The method of claim 1, further comprising:
generating the combined reference genome; and
identifying, for each of the one or more gene sequences, a corresponding location within the combined reference genome, wherein the corresponding location indicates the origin species of the corresponding gene sequence.

5. The method of claim 1, further comprising:
for each species-specific RNA sequence, determining that the exactly one corresponding gene sequence is associated with a predetermined cluster of gene sequences.

6. The method of claim 5, wherein the predetermined cluster of gene sequences comprises a group of genes sharing one or more functional characteristics.

7. The method of claim 6, wherein the one or more functional characteristics comprises one or more biological processes or canonical pathways.

8. The method of claim 7, wherein the one or more biological processes or functional characteristics comprise one or more of transcriptional regulation, intracellular signaling, intercellular signaling, cell apoptosis, biomolecule metabolism, biomolecule synthesis, RNA processing, or macromolecule assembly.

9. The method of claim 1, wherein the biomarker indicative of the disease status comprises a nucleic acid sequence associated with a disease.

10. The method of claim 1, wherein the disease status comprises at least one of:
the presence or absence of a disease state, one or more characteristics of an existing disease state,
a likelihood of a future progression of an existing disease state, or
one or more characteristics of a predicted future progression of an existing disease state.

11. The method of claim 1, further comprising determining, based on determining that the tissue derived from the donor organism contains the biomarker indicative of the disease status, a therapy to be administered to at least one of the host organism or the donor organism.

12. The method of claim 11, further comprising administering the determined therapy to the at least one of the host organism or the donor organism.

13. The method of claim 1, wherein the response of the host organism to the tissue derived from the donor organism corresponds to one of acceptance or rejection of the tissue derived from the donor organism by the host organism.

14. The method of claim 1, wherein obtaining the plurality of exosomes from the sample of bodily fluid derived from the host organism comprises:
obtaining a sample of blood;
isolating, from the sample of blood, a volume of blood serum; and
isolating, from the volume of blood serum, the plurality of exosomes.

15. The method of claim 1, further comprising:
isolating, from the plurality of exosomes, the plurality of molecules of RNA;
purifying the molecules of RNA;
performing a reverse-transcriptase polymerase chain reaction using the molecules of RNA to produce a plurality of molecules of complementary deoxyribonucleic acid (cDNA), wherein each molecule of the plurality of molecules of cDNA corresponds to one of the plurality of molecules of RNA;
performing a polymerase chain reaction to amplify the molecules of cDNA;
transcribing substantially each of the molecules of cDNA into RNA; and
determining the nucleic acid sequence of substantially each of the molecules of RNA.

16. The method of claim 1, wherein the first species comprises one of a rodent species or a non-human primate species.

17. The method of claim 1, wherein the second species comprises one of a canine, feline, porcine, or human species.

18. The method of claim 1, further comprising determining that the tissue derived from the donor organism contains the biomarker indicative of at least one of:
a disease status based on abundance levels of species-specific RNA sequences associated with the second species,
a response of the host organism to the tissue derived from the donor organism based on abundance levels of species-specific RNA sequences associated with the first species, or
a response of tissue derived from the donor organism to transplantation within the host organism based on abundance levels of species-specific RNA sequences associated with the second species.

19. A method comprising:
identifying, by processing circuitry, a corresponding RNA sequence for substantially each molecule of a plurality of molecules of messenger ribonucleic acid (mRNA), wherein a plurality of exosomes from a sample of bodily fluid derived from a host organism of a first species comprises the plurality of molecules of mRNA, and wherein the host organism comprises xenografted tissue derived from a donor organism of a second species;
generating, by the processing circuitry, a combined dataset of RNA sequence reads by aligning each RNA sequence to a combined reference genome, wherein aligning each RNA sequence to the combined reference genome includes comparing a genomic location of each corresponding RNA sequence with a genomic location of a gene sequence of the combined reference genome, wherein the combined reference genome includes gene sequences from at least a portion of a first genome derived from the first species and at least a portion of a second genome derived from the second species, wherein the combined reference genome indicates an origin species of each corresponding gene sequence, and wherein the combined dataset of RNA sequence reads includes RNA sequence reads from both the first species and the second species;
filtering, by the processing circuitry, non-unique RNA sequence reads from the combined dataset by identifying species-specific RNA sequences exclusive to either the first species or the second species, wherein identifying species-specific RNA sequences includes determining, for each corresponding RNA sequence, whether the RNA sequence is substantially aligned with exactly one corresponding gene sequence of the combined reference genome;
differentiating, by the processing circuitry, an origin species of each species-specific RNA sequence in the filtered combined dataset by determining whether the corresponding RNA sequence is aligned to a gene sequence of the combined reference genome associated with the first genome of the first species or the second genome of the second species;

quantifying, by the processing circuitry, an abundance level of each species-specific RNA sequence in the sample by determining an approximate number of times that each species-specific RNA sequence occurs in the filtered combined dataset; and determining, by the processing circuitry and based on the abundance level of species-specific RNA sequences associated with at least one of the first species or the second species in the sample of bodily fluid either increasing over a period of time or exceeding a predetermined threshold, that the tissue derived from the donor organism contains a biomarker indicative of at least one of:
a disease status,
a response of the host organism to the tissue derived from the donor organism, or
a response of the tissue derived from the donor organism to transplantation within the host organism.

20. The method of claim 19, further comprising:
generating the combined reference genome; and
identifying, for each of the one or more gene sequences, a corresponding location within the combined reference genome, wherein the corresponding location indicates the origin species of the corresponding gene sequence.

21. The method of claim 19, further comprising:
for each species-specific RNA sequence, determining that the exactly one corresponding gene sequence is associated with a predetermined cluster of gene sequences.

22. The method of claim 21, wherein the predetermined cluster of gene sequences comprises a group of genes sharing one or more functional characteristics.

23. The method of claim 19, wherein the biomarker indicative of the disease status comprises a nucleic acid sequence associated with a disease.

24. The method of claim 19, wherein the disease status comprises at least one of:
the presence or absence of a disease state, one or more characteristics of an existing disease state,
a likelihood of a future progression of an existing disease state, or
one or more characteristics of a predicted future progression of an existing disease state.

25. The method of claim 19, further comprising determining, based on determining that the tissue derived from the donor organism contains the biomarker indicative of the disease status, a therapy to be administered to at least one of the host organism or the donor organism.

26. The method of claim 19, wherein the response of the host organism to the tissue derived from the donor organism corresponds to one of acceptance or rejection of the tissue derived from the donor organism by the host organism.

27. A system comprising:
a reservoir configured to receive a sample of bodily fluid; and
processing circuitry configured to:
identify a corresponding RNA sequence for substantially each molecule of a plurality of molecules of messenger ribonucleic acid (mRNA), wherein a plurality of exosomes from the sample of bodily fluid is derived from a host organism of a first species and comprises the plurality of molecules of RNA, and wherein the first organism comprises xenografted tissue derived from a donor organism of a second species;

generate a combined dataset of RNA sequence reads by aligning each RNA sequence to a combined reference genome, wherein aligning each RNA sequence to the combined reference genome includes comparing a genomic location of each corresponding RNA sequence with a genomic location of a gene sequence of the combined reference genome, wherein the combined reference genome includes gene sequences from at least a portion of a first genome derived from the first species and at least a portion of a second genome derived from the second species, wherein the combined reference genome indicates an origin species of each corresponding gene sequence, and wherein the combined dataset of RNA sequence reads includes RNA sequence reads from both the first species and the second species;

filter non-unique RNA sequence reads from the combined dataset by identifying species-specific RNA sequences exclusive to either the first species or the second species, wherein identifying species-specific RNA sequences includes determining, for each corresponding RNA sequence, whether the RNA sequence is substantially aligned with exactly one corresponding gene sequence of the combined reference genome;

differentiate an origin species of each species-specific RNA sequence in the filtered combined dataset by determining whether the corresponding RNA sequence is aligned to a gene sequence of the combined reference genome associated with the first genome of the first species or the second genome of the second species;

quantify an abundance level of each species-specific RNA sequence in the sample by determining an approximate number of times that each species-specific RNA sequence occurs in the filtered combined dataset; and determine, based on the abundance level of species-specific RNA sequences associated with at least one of the first species or the second species in the sample of bodily fluid either increasing over a period of time or exceeding a predetermined threshold, that the tissue derived from the donor organism contains a biomarker indicative of at least one of:
a disease status,
a response of the host organism to the tissue derived from the donor organism, or
a response of tissue derived from the donor organism to transplantation within the host organism.

28. The system of claim 27, wherein the processing circuitry is further configured to:
generate the combined reference genome; and
identify, for each of the one or more gene sequences, a corresponding location within the combined reference genome, wherein the corresponding location indicates the origin species of the corresponding gene sequence.

29. The system of claim 27, wherein the biomarker indicative of the disease status comprises a nucleic acid sequence associated with a disease.

30. The system of claim 27, wherein the response of the host organism to the tissue derived from the donor organism corresponds to one of acceptance or rejection of the tissue derived from the donor organism by the host organism.

\* \* \* \* \*